(12) United States Patent
Lavis et al.

(10) Patent No.: US 12,157,750 B2
(45) Date of Patent: *Dec. 3, 2024

(54) BRIGHT TARGETABLE RED $CA^{2+}$ INDICATORS

(71) Applicant: HOWARD HUGHES MEDICAL INSTITUTE, Chevy Chase, MD (US)

(72) Inventors: Luke D. Lavis, Ashburn, VA (US); Claire Deo, Heidelberg (DE)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/940,199

(22) Filed: Sep. 8, 2022

(65) Prior Publication Data

US 2023/0038702 A1 Feb. 9, 2023

Related U.S. Application Data

(63) Continuation of application No. 17/001,332, filed on Aug. 24, 2020, now Pat. No. 11,498,932.

(Continued)

(51) Int. Cl.
*C07F 7/08* (2006.01)
*C07D 405/04* (2006.01)
(Continued)

(52) U.S. Cl.
CPC .......... *C07F 7/0816* (2013.01); *C07D 405/04* (2013.01); *C07D 405/14* (2013.01); *G01N 21/78* (2013.01)

(58) Field of Classification Search
CPC .. C07D 405/04; C07D 405/14; C07D 493/08; C07F 7/0816
See application file for complete search history.

(56) References Cited

U.S. PATENT DOCUMENTS

2014/0349282 A1* 11/2014 Umezawa ............... C09B 57/00 435/7.1
2020/0087326 A1* 3/2020 Hanaoka ............... C07F 7/0807

FOREIGN PATENT DOCUMENTS

WO WO 2015-153813 * 10/2015

OTHER PUBLICATIONS

Deo et al. (J. Am. Chem. Soc. 2019, 141, 13734-13738).*
(Continued)

*Primary Examiner* — Valerie Rodriguez-Garcia
(74) *Attorney, Agent, or Firm* — Stites & Harbison, PLLC; Mandy Wilson Decker

(57) ABSTRACT

The presently-disclosed subject matter includes fluorescent indicators, including bright and targetable red Ca2+ indicators. The presently-disclosed subject matter also includes kits comprising the same as well as methods for using the same to detect a target substance. Fluorescent indicators of the presently-disclosed subject matter include a compound of the formula:

(Continued)

-continued

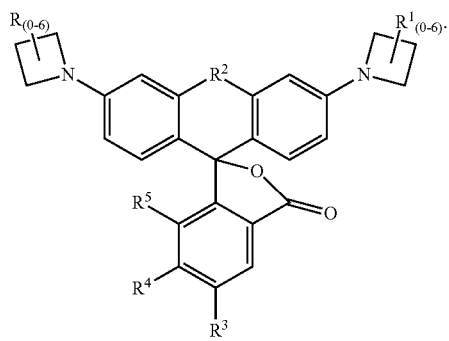

16 Claims, 12 Drawing Sheets

Related U.S. Application Data

(60) Provisional application No. 62/891,007, filed on Aug. 23, 2019.

(51) Int. Cl.
*C07D 405/14* (2006.01)
*G01N 21/78* (2006.01)

(56) References Cited

OTHER PUBLICATIONS

Numasawa, K., et al. A cytosolically localized far-red to near-infrared rhodamine-based fluorescent probe for calcium ions. Analyst, 2020, 145, 7736-7740.
Numasawa, K., et al. Supplementary Information. A cytosolically localized far-red to near-infrared rhodamine-based fluorescent probe for calcium ions, Sep. 23, 2020.

\* cited by examiner

1
Oregon Green BAPTA-1
$\Phi_{sat} = 0.70$, $\Delta F/F_0 = 14$

2
Calcium Orange
$\Phi_{sat} = 0.33$, $\Delta F/F_0 = 3$

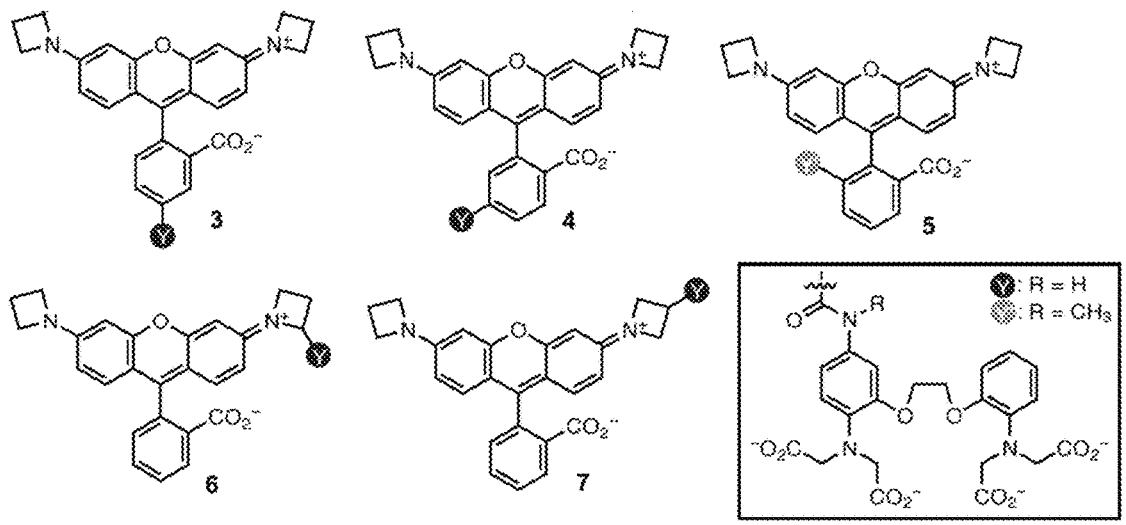
FIG. 2A
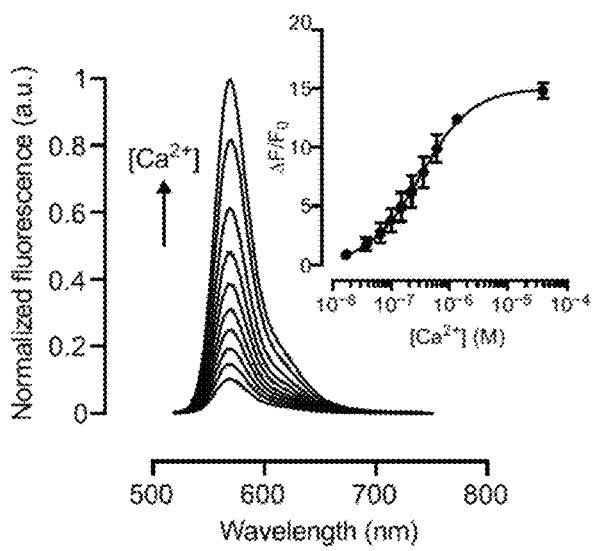
| Compound | $\Phi_{sat}$ | $\Delta F/F_0$ | $K_d$ (µM) |
|---|---|---|---|
| 1 | 0.70 | 14 | 0.170 |
| 2 | 0.33 | 3 | 0.185 |
| 3 | 0.69 | 2.3 | 0.19 |
| 4 | 0.78 | 4.6 | 0.35 |
| 5 | 0.18 | 14.0 | 0.57 |
| 6 | 0.45 | 27.7 | 0.27 |
| 7 | 0.75 | 15.0 | 0.31 |
FIG. 2B
FIG. 2C

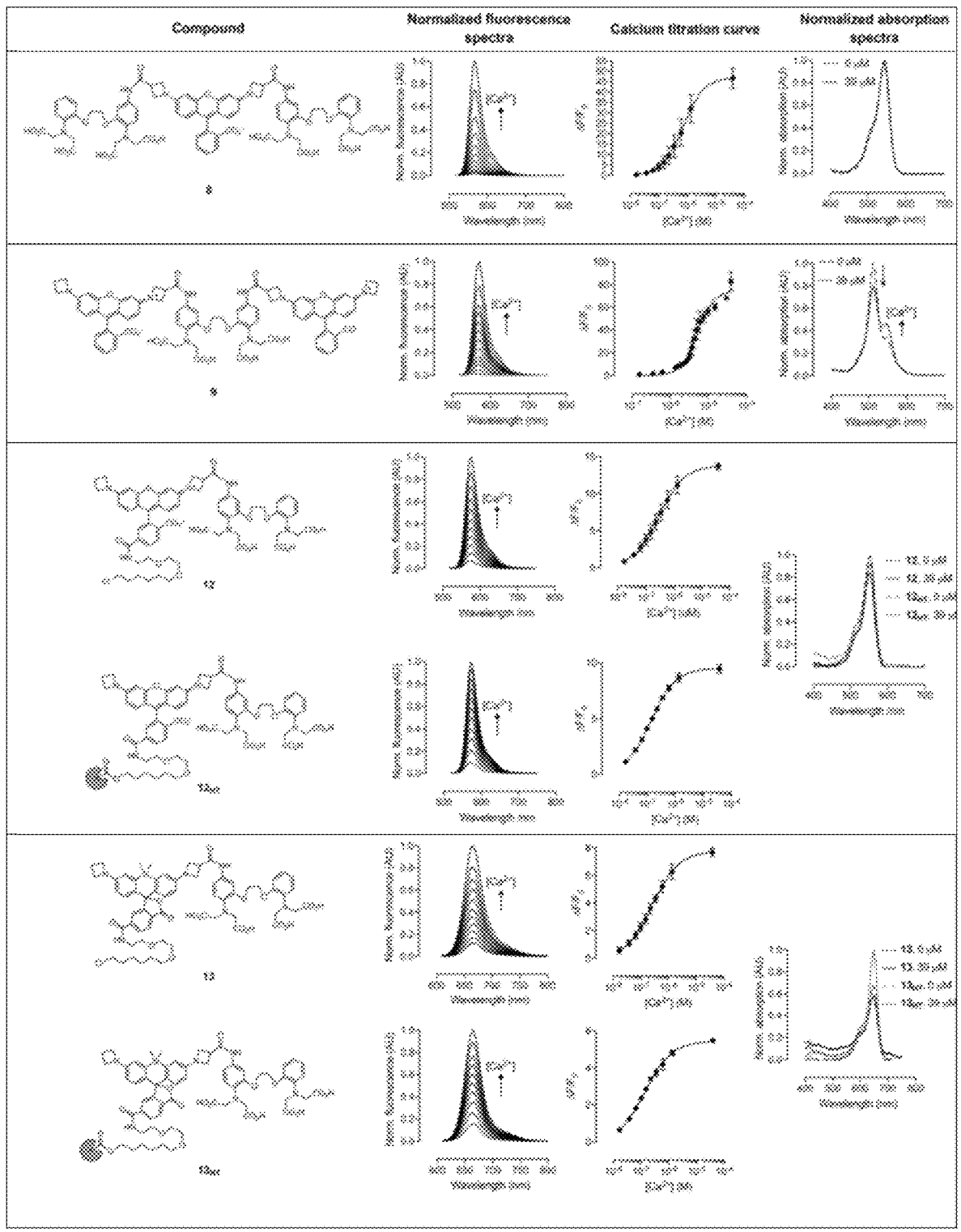
FIG. 9, Continued

BRIGHT TARGETABLE RED CA$^{2+}$ INDICATORS

RELATED APPLICATIONS

This application is a continuation of U.S. patent application Ser. No. 17/001,332 filed Aug. 20, 2020, which is now allowed, and claims priority from U.S. Provisional Application Ser. No. 62/891,007 filed Aug. 23, 2019, the entire disclosures of which are incorporated herein by this reference.

TECHNICAL FIELD

The presently-disclosed subject matter generally relates to fluorescent indicators. In particular, certain embodiments of the presently-disclosed subject matter relate to bright and targetable red Ca2+ indicators.

INTRODUCTION

The calcium ion is an important second messenger involved in the regulation of multiple cellular processes[1] and a fidelic proxy for neural activity.[2] Fluorescent Ca$^{2+}$ indicators enable functional 'calcium imaging' with high spatiotemporal resolution. Existing indicators fall into two classes based on either small molecule fluorophores or fluorescent proteins. Chemical indicators benefit from superior fluorescence properties, but have no inherent cell-type specificity.[3] Genetically encoded calcium indicators (GECIs) are eminently targetable and have revolutionized in vivo calcium imaging,[4-5] but this sensor type is limited by the suboptimal properties of fluorescent proteins, particularly in the far-red spectral region (>640 nm).[6-7]

A promising approach to combine the photophysical properties of synthetic indicators and the specificity of GECIs utilizes self-labeling tags to localize chemical dyes within a cell. Despite pioneering work using the Cys4-tag,[8] SNAP-tag,[9-10] and HaloTag,[11] the incorporation of a ligand moiety into an existing small-molecule indicator can be synthetically challenging and often compromises cellular performance.

Described herein is a unique approach to the design of small-molecule Ca$^{2+}$ indicators where the relative positions of the fluorophore and chelator motif are systematically explored. This 'isomeric tuning' uncovers a novel indicator configuration that is bright, sensitive, and compatible with the HaloTag labeling system. This design can be extended to far-red dyes, enabling measurement of Ca$^{2+}$ dynamics in the primary cilium.

Most synthetic Ca$^{2+}$ indicators utilize Roger Tsien's chelator: 1,2-bis(o-aminophenoxy)ethane-N,N,N',N'-tetraacetic acid (BAPTA) fused to a fluorophore; a classic example is Oregon Green BAPTA-1 (1, FIG. 1).[12-14] This compound exhibits an excitation maxima ($\lambda$ex) of 492 nm and fluorescence emission maxima ($\lambda$em) of 523 nm. In the Ca2+-free state, the fluorescence emission of 1 is quenched by photoinduced electron transfer (PeT) from the BAPTA moiety to the fluorophoric system. Ca2+ chelation alters the electronic structure of the BAPTA, resulting in reduced PeT quenching and increased fluorescence. Compound 1 shows a high fluorescence quantum yield at saturating Ca$^{2+}$ (($\Phi$sat=0.70) and excellent sensitivity with a change in fluorescence over baseline ($\Delta$F/F0) of 14; this molecule has been used broadly for calcium imaging in neurons and brain tissue.[15-16] The efficiency of PeT quenching is wavelength dependent,[17-18] however; the analogous red-shifted Calcium Orange (2; $\lambda$ex/$\lambda$em=549 nm/574 nm) based on tetramethylrhodamine (TMR) displays a lower sensitivity ($\Delta$F/F0=3) and fluorescence quantum yield (($\Phi$sat=0.33).[15]

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-subject matter includes compounds, comprising fluorescent indicators. In some embodiments, compounds of the presently-disclosed subject matter include bright and targetable red Ca2+ indicators. The presently-disclosed subject matter also includes kits comprising the same as well as methods for using the same to detect a target substance.

Embodiments of the presently-disclosed subject matter include exemplary compound according to the following formulae:

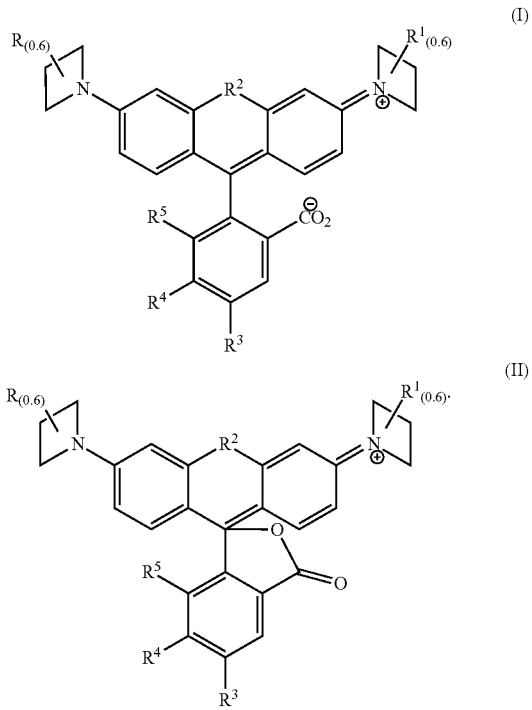

While structures are provided herein for illustrative purposes, those of ordinary skill in the art, with an understanding of zwitterions, will appreciate all the open and closed forms of the compounds disclosed herein upon review of this document.

In some embodiments of the presently-disclosed subject matter, R as set forth in formulae (I) and (II) is selected from the group consisting of halogen, H, OH, CN, O(alkyl), N(alkyl), amine, $NO_2$, CHO, COOH, COO(alkyl), $O(SO_2CF_3)$, and

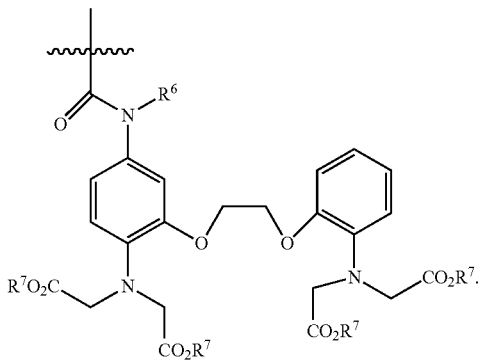

In some embodiments of the presently-disclosed subject matter, $R^1$ as set forth in formulae (I) and (II) is selected from the group consisting of halogen, H, OH, CN, O(alkyl), N(alkyl), amine, $NO_2$, CHO, COOH, COO(alkyl), $O(SO_2CF_3)$,

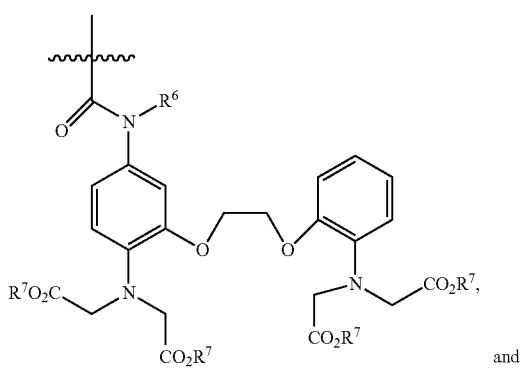

and

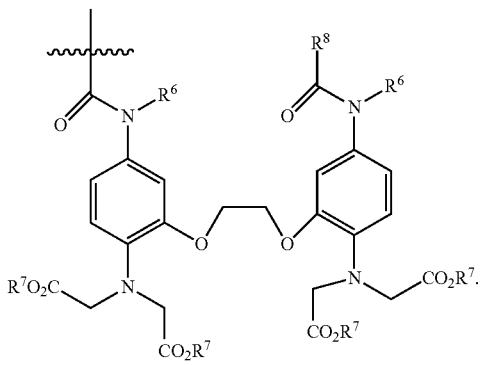

In some embodiments of the presently-disclosed subject matter, $R^2$ as set forth in formulae (I) and (II) is selected from the group consisting of O, $Si(CH_3)_2$, and $C(CH_3)_2$;

In some embodiments of the presently-disclosed subject matter, $R^3$ as set forth in formulae (I) and (II) is selected from the group consisting of H, $CO_2$t-Bu, $CO_2H$, and

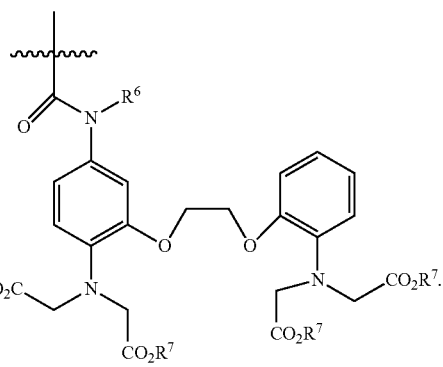

In some embodiments of the presently-disclosed subject matter, $R^4$ as set forth in formulae (I) and (II) is selected from the group consisting of H, $CO_2$t-Bu, $CO_2H$, a self-labeling protein tag ligand, and

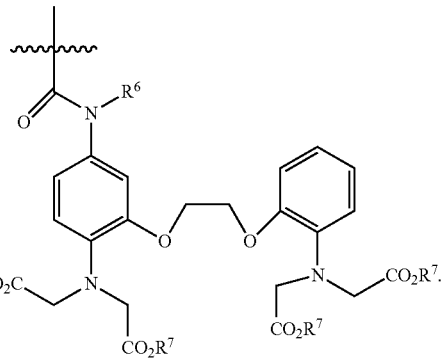

In some embodiments of the presently-disclosed subject matter, $R^5$ as set forth in formulae (I) and (II) is selected from the group consisting of H, $CO_2CH_3$, and

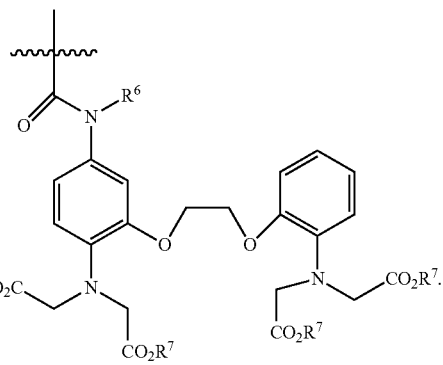

In some embodiments of the presently-disclosed subject matter, $R^6$ as set forth in formulae (I) and (II) is selected from the group consisting of H and $CH_3$ In some embodiments of the presently-disclosed subject matter, $R^7$ as set forth in formulae (I) and (II) is selected from the group consisting of H, acetoxymethyl (AM), or

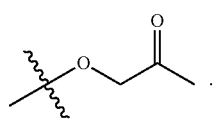 [SMILES: *OCC(C)=O]

In some embodiments of the presently-disclosed subject matter, $R^8$ as set forth in formulae (I) and (II) is selected from the group consisting of

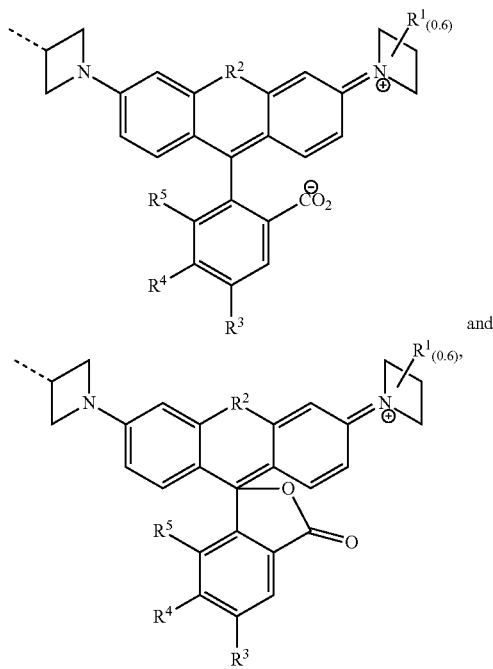

and wherein $R^1$, $R^2$, $R^3$, $R^4$, $R^5$, $R^6$, $R^7$, and $R^8$ are defined as described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A includes chemical structures of exemplary $JF_{549}$-based $Ca^{2+}$ indicators provided in accordance with the presently disclosed subject matter (Compounds 3-7).

FIG. 2B includes a table of photophysical properties and $Ca^{2+}$ binding for Compounds 3-7.

FIG. 2C includes a graph illustrating $Ca^{2+}$-dependent change in fluorescence and titration (inset) of Compound 7.

(FIG. 5C) GFP channel (FIG. 5D) JF549 channel (FIG. 5E) merge with overlay showing average response to 1 AP; scale bars: 50 μm.

DESCRIPTION OF EXEMPLARY EMBODIMENTS

Figure 1A:
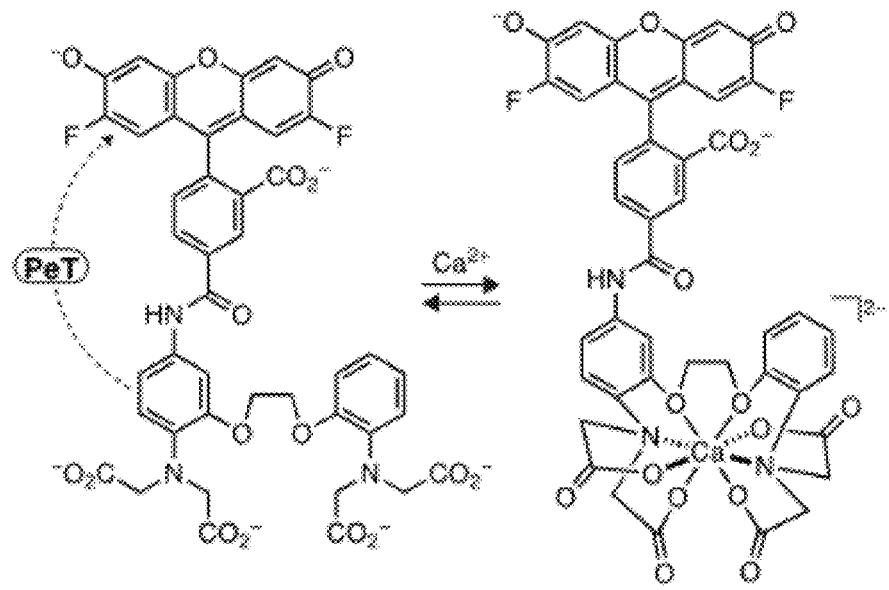
FIG. 1A includes the structure of Oregon Green BAPTA-1 (Compound 1).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-subject matter includes compounds, comprising fluorescent indicators. In some embodiments, compounds of the presently-disclosed subject matter include bright and targetable red Ca2+ indicators. The presently-disclosed subject matter also includes kits comprising the same as well as methods for using the same to detect a target substance.

Embodiments of the presently-disclosed subject matter include exemplary compound according to the following formulae:

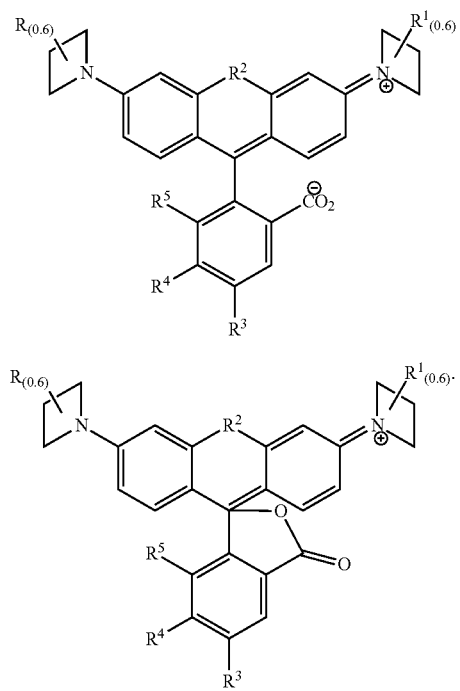

In some embodiments of the presently-disclosed subject matter, R as set forth in formulae (I) and (II) is selected from the group consisting of halogen, H, OH, CN, O(alkyl), N(alkyl), amine, $NO_2$, CHO, COOH, COO(alkyl), $O(SO_2CF_3)$, and

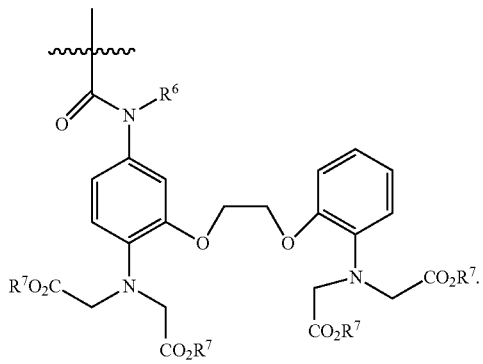

In some embodiments of the presently-disclosed subject matter, $R^1$ as set forth in formulae (I) and (II) is selected from the group consisting of halogen, H, OH, CN, O(alkyl), N(alkyl), amine, $NO_2$, CHO, COOH, COO(alkyl), $O(SO_2CF_3)$,

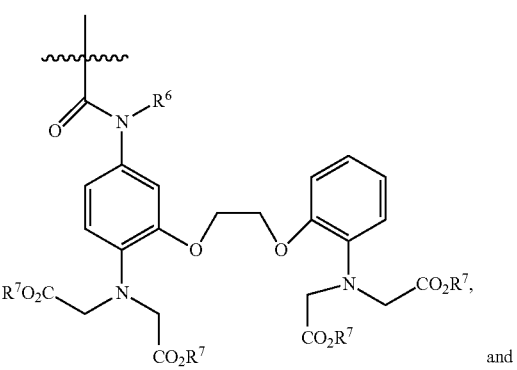

In some embodiments of the presently-disclosed subject matter, $R^2$ as set forth in formulae (I) and (II) is selected from the group consisting of O, $Si(CH_3)_2$, and $C(CH_3)_2$;

In some embodiments of the presently-disclosed subject matter, $R^3$ as set forth in formulae (I) and (II) is selected from the group consisting of H, $CO_2$t-Bu, $CO_2H$, and

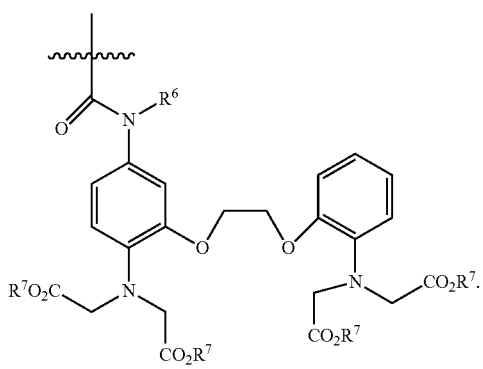

In some embodiments of the presently-disclosed subject matter, $R^4$ as set forth in formulae (I) and (II) is selected from the group consisting of H, $CO_2$t-Bu, $CO_2H$, a self-labeling protein tag ligand, and

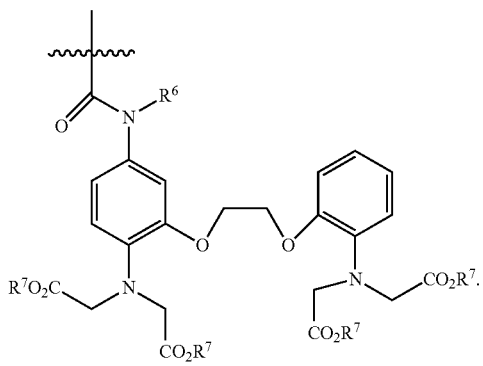

In some embodiments of the presently-disclosed subject matter, $R^5$ as set forth in formulae (I) and (II) is selected from the group consisting of H, $CO_2CH_3$, and

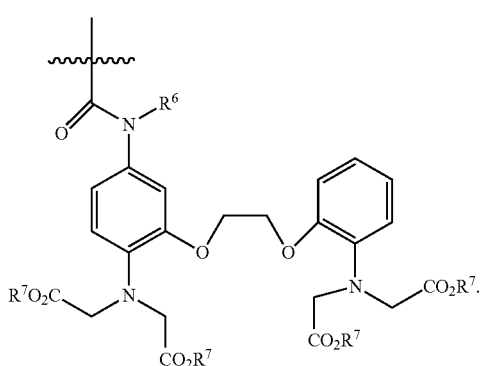

In some embodiments of the presently-disclosed subject matter, $R^6$ as set forth in formulae (I) and (II) is selected from the group consisting of H and $CH_3$ In some embodiments of the presently-disclosed subject matter, $R^7$ as set forth in formulae (I) and (II) is selected from the group consisting of H, acetoxymethyl (AM), or

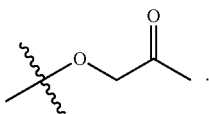 [SMILES: *OCC(C)=O]

In some embodiments of the presently-disclosed subject matter, $R^8$ as set forth in formulae (I) and (II) is selected from the group consisting of

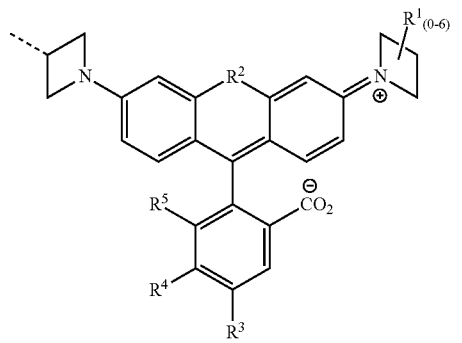

and

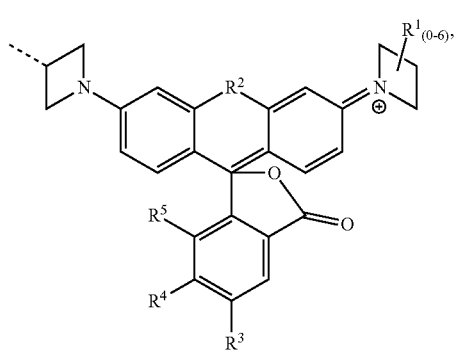

wherein $R^1$, $R^2$, $R^3$, $R^4$, $R^5$, $R^6$, $R^7$, and $R^8$ are defined as described herein.

In some embodiments of the compounds as described herein, not more than one of R, $R^3$, $R^4$, and $R^5$ is

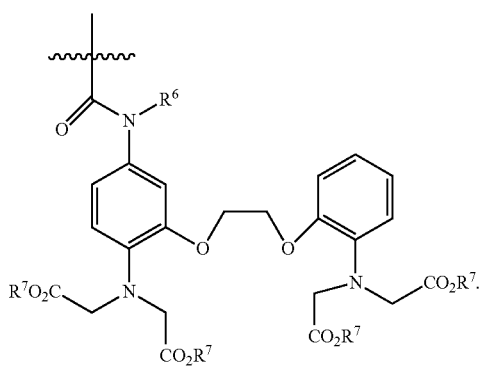

In some embodiments of the compounds as described herein, one of R, $R^3$, $R^4$, and $R^5$ is
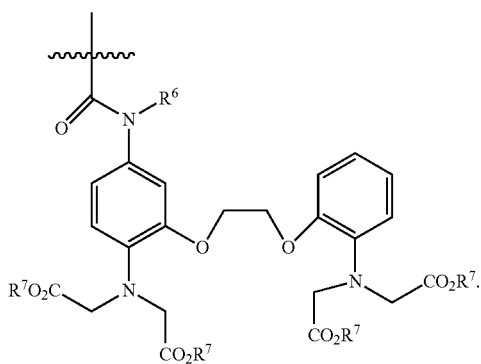
In some embodiments of the compounds as described herein R is H. In some embodiments of the compounds as described herein R is
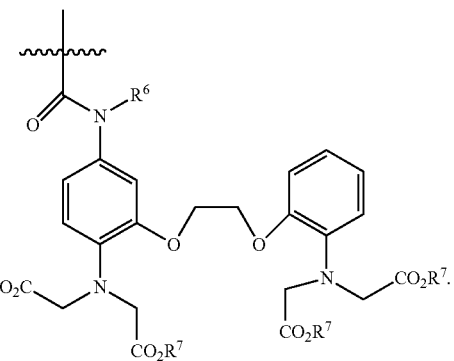
In some embodiments, the compound has a formula of, or a zwitterion, the group consisting of:
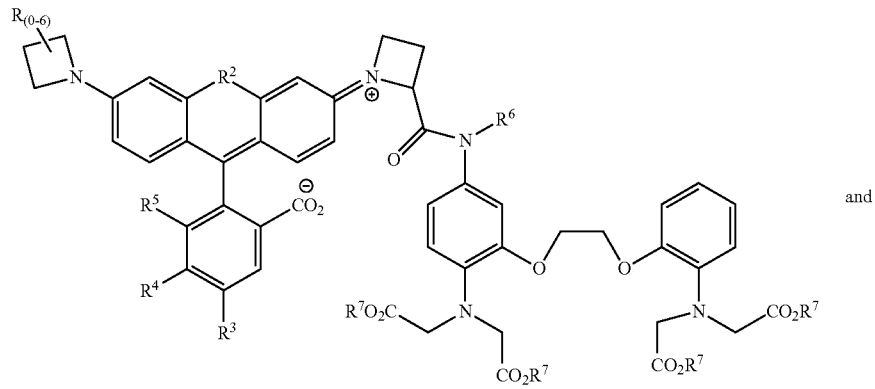
and
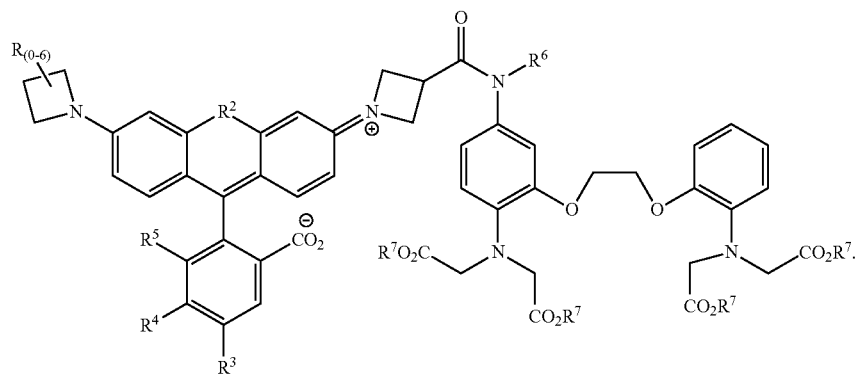

In some embodiments of the compounds as described herein $R^1$ is H. In some embodiments of the compounds as described herein $R^1$ is

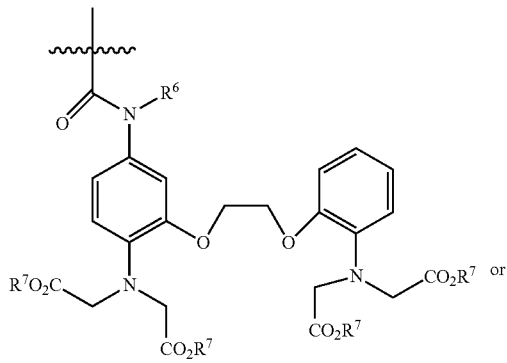

In some embodiments of the compounds as described herein $R^3$ is H. In some embodiments of the compounds as described herein $R^3$ is

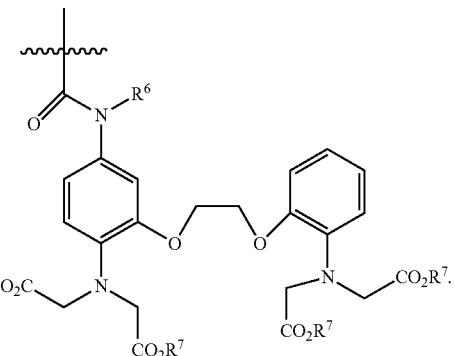

In some embodiments of the compounds as described herein $R^4$ is H. In some embodiments of the compounds as described herein $R^4$ is a self-labeling protein tag ligand. In some embodiments of the compounds as described herein the self-labeling protein tag ligand is

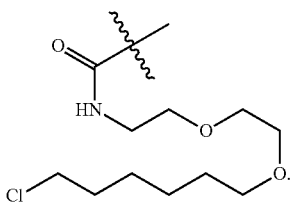 [SMILES: *C(=O)NCCOCCOCCCCCCCl]

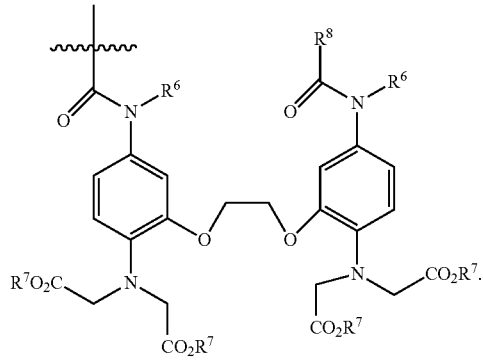

In some embodiments of the compounds as described herein $R^5$ is H. In some embodiments of the compounds as described herein $R^5$ is

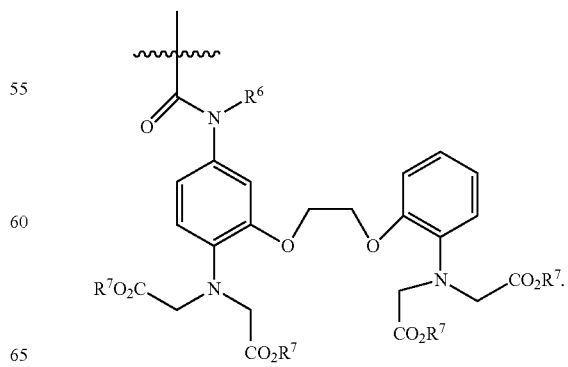

In some embodiments of the compounds as described herein $R^1$ is selected from the group consisting of COOH, COOCH$_3$, and O(SO$_2$CF$_3$).

In some embodiments of the compounds as described herein $R^2$ is Si(CH$_3$)$_2$. In some embodiments of the compounds as described herein $R^2$ is O.

Some embodiments of the compounds as described herein are selected from one of the following formulae:
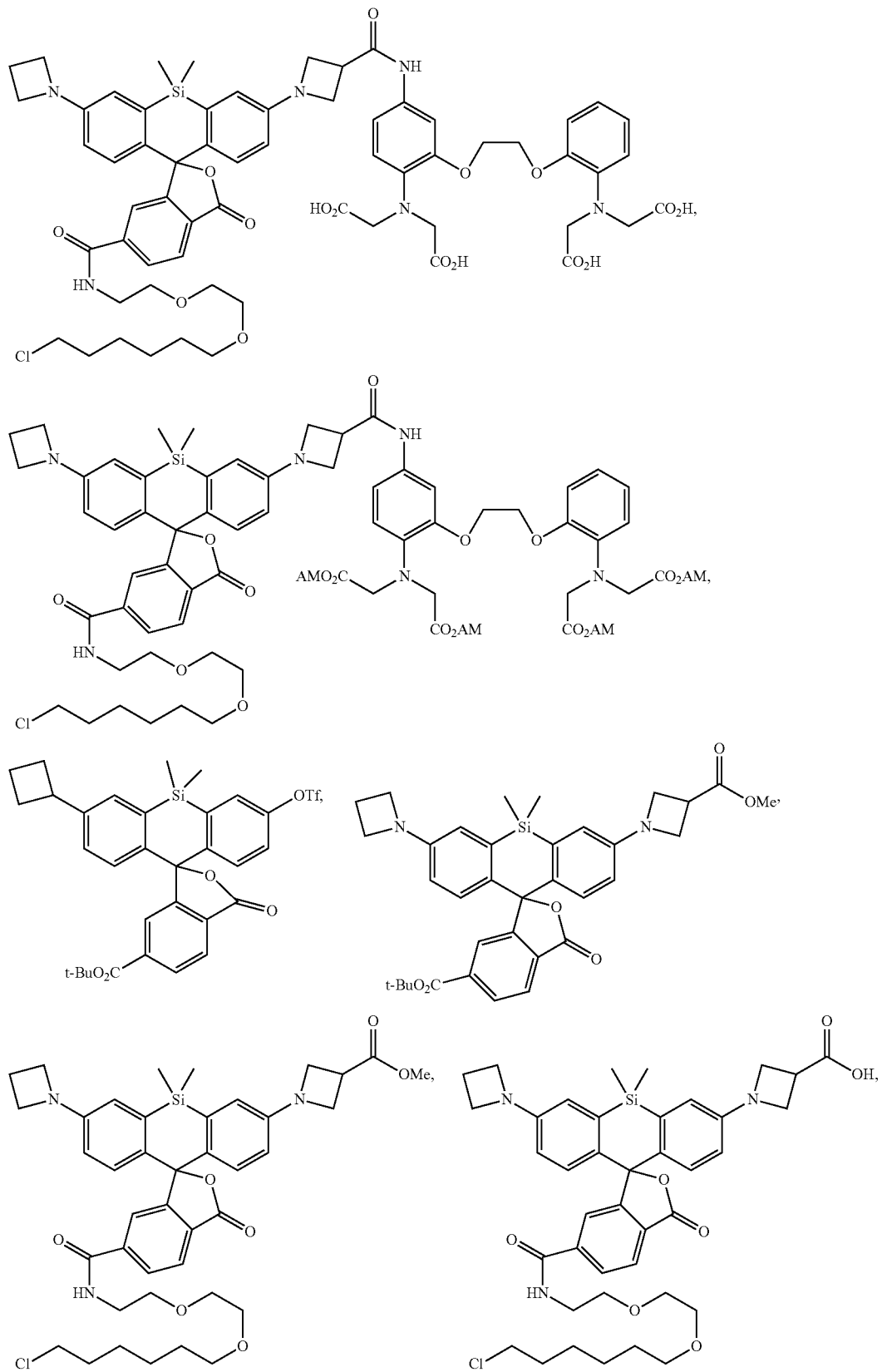

-continued
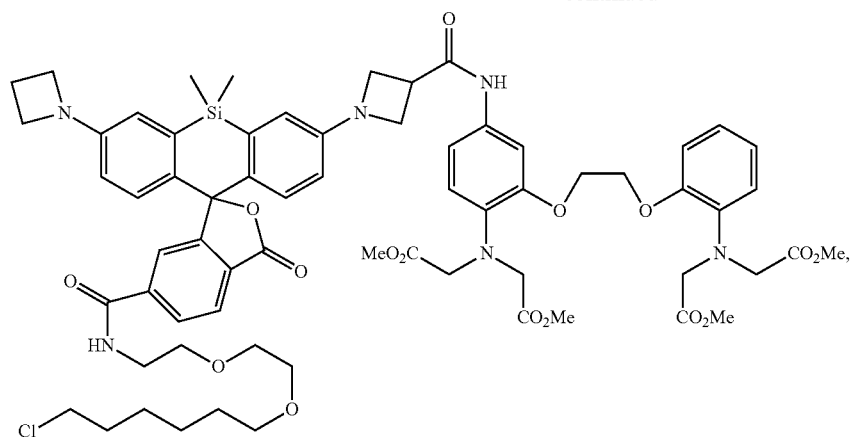 [SMILES: COC(=O)CN(CC(=O)OC)c1ccccc1OCCOc1cc(NC(=O)C2CN(c3ccc4c(c3)[Si](C)(C)c3cc(N5CCC5)ccc3C43OC(=O)c4ccc(C(=O)NCCOCCOCCCCCCCl)cc43)C2)ccc1N(CC(=O)OC)CC(=O)OC]
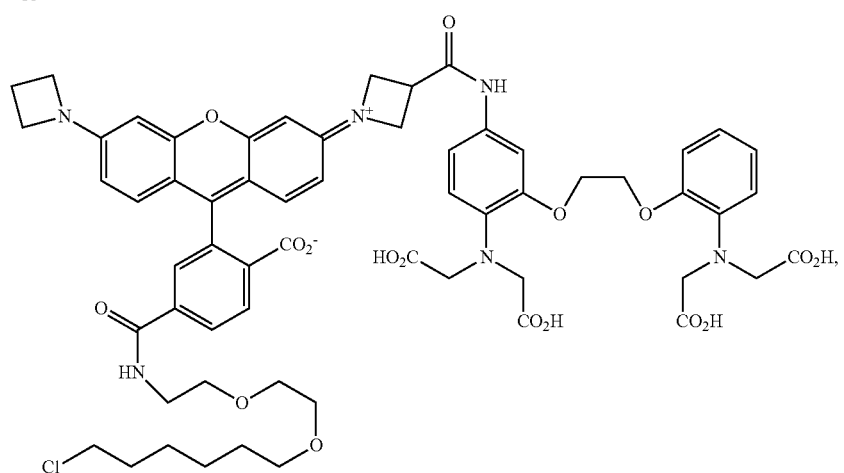
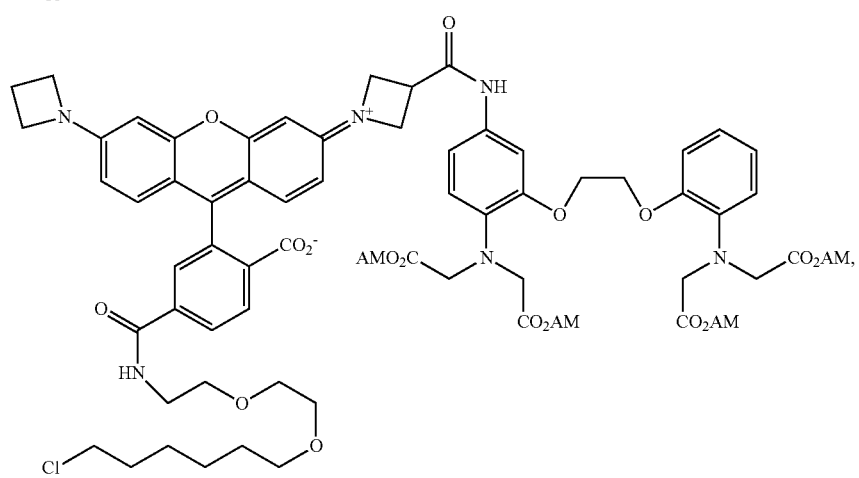
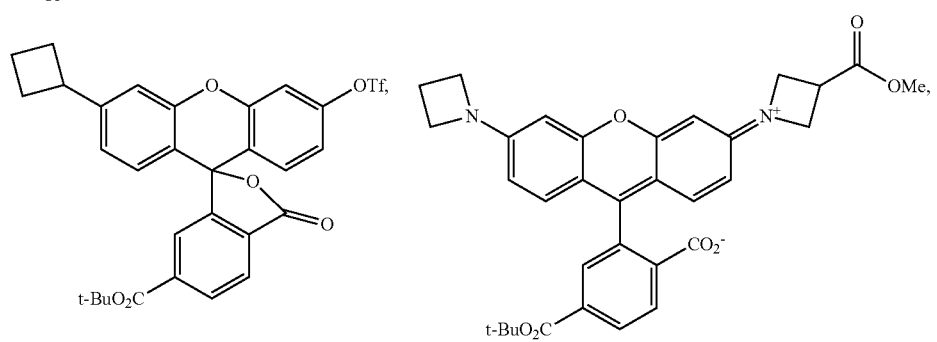

-continued
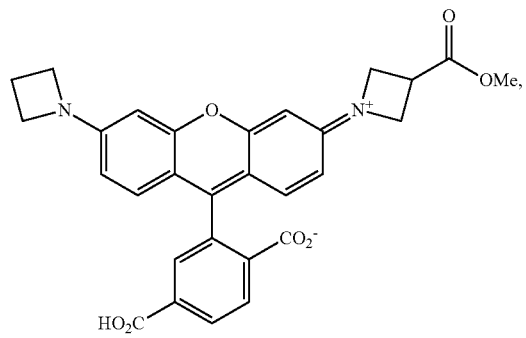
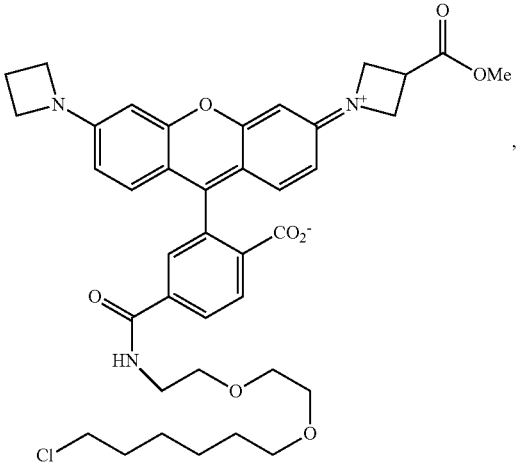
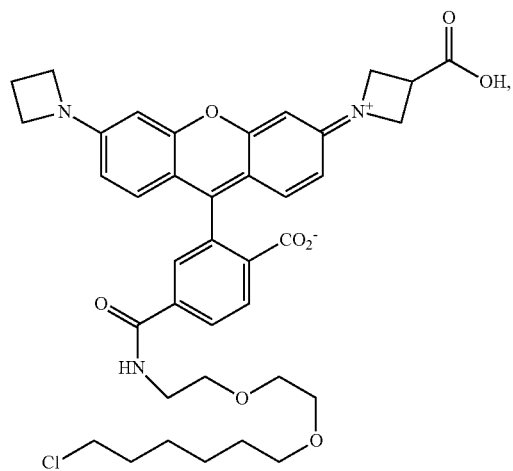
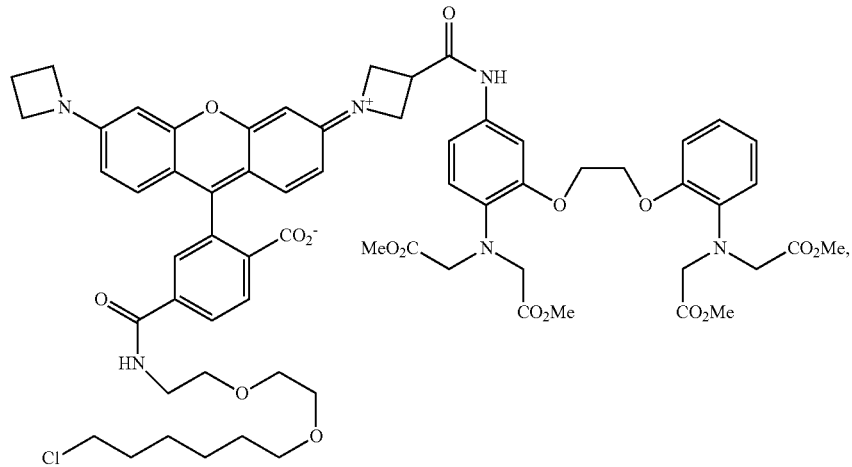
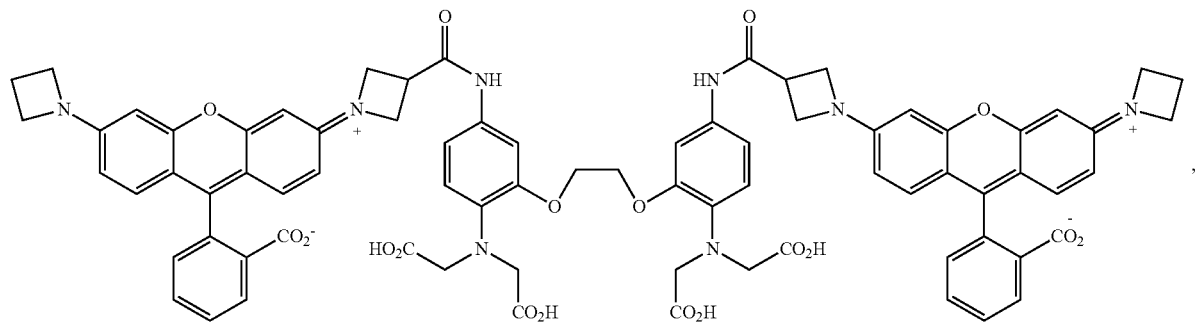

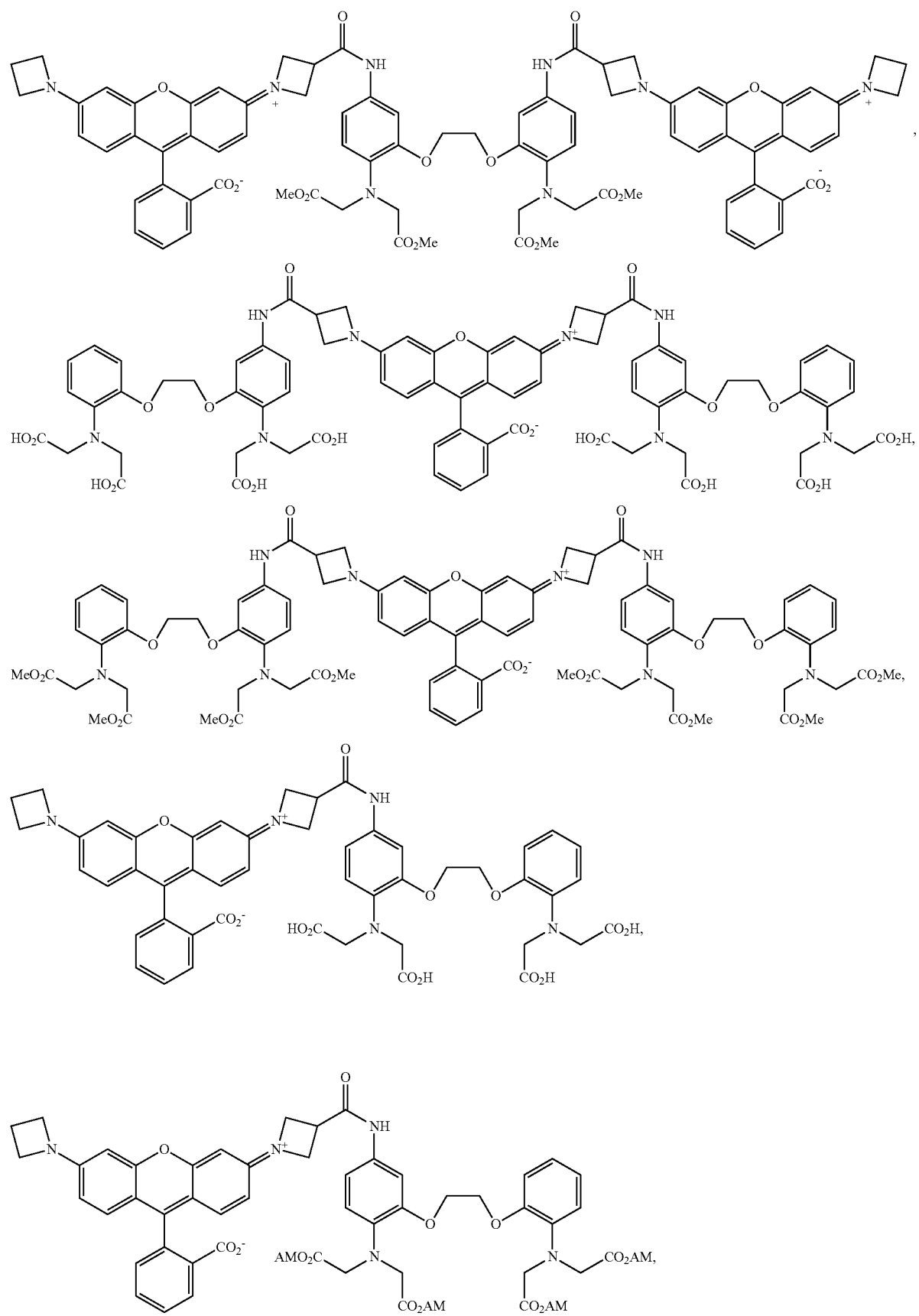

-continued
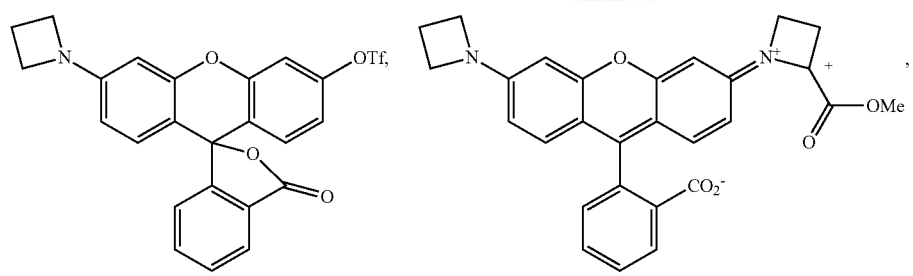
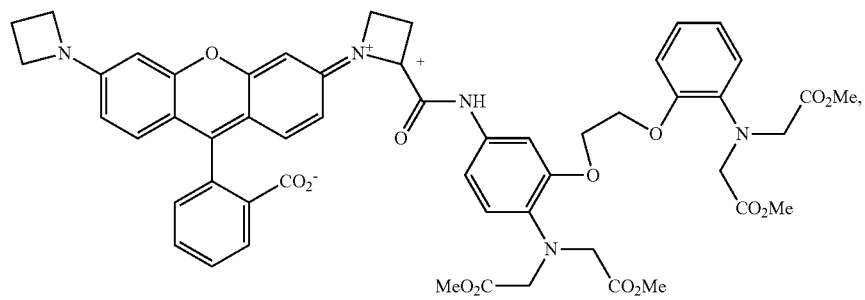
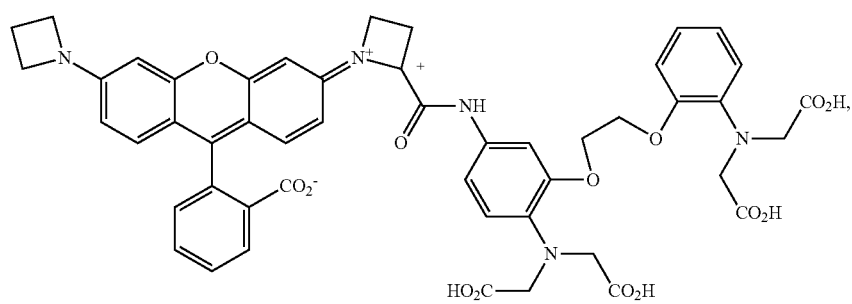
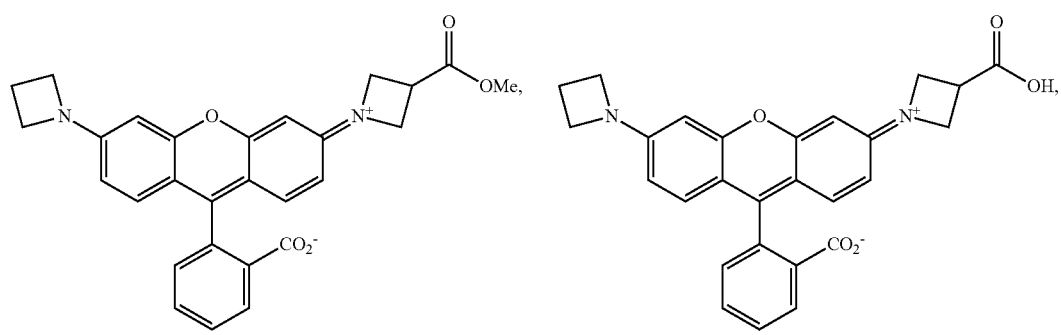
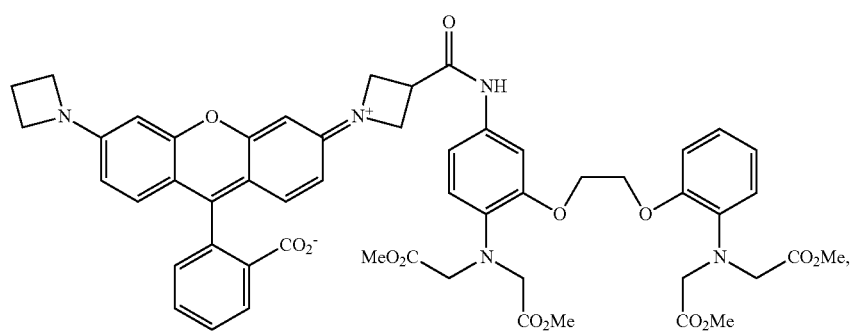

25 26
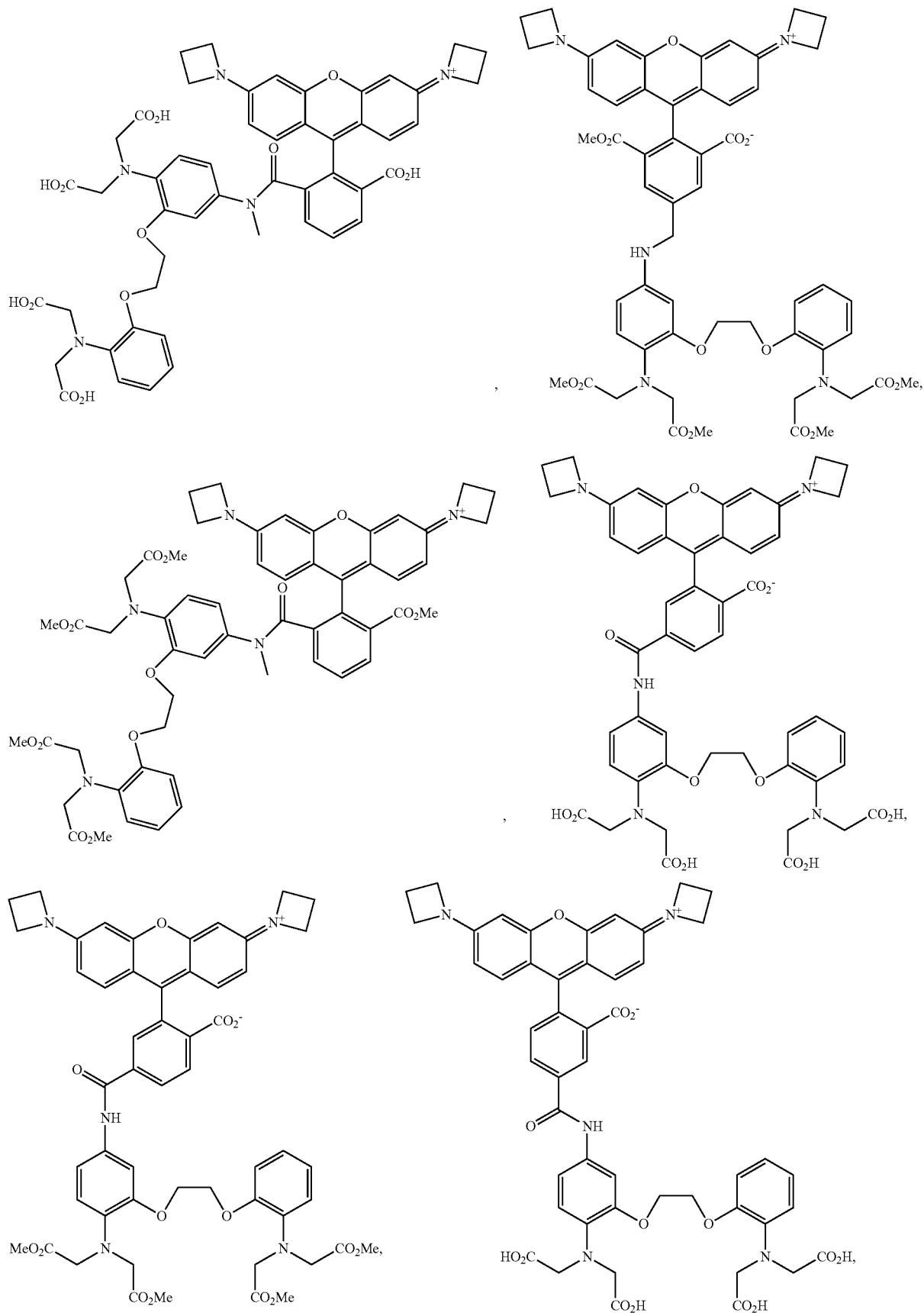

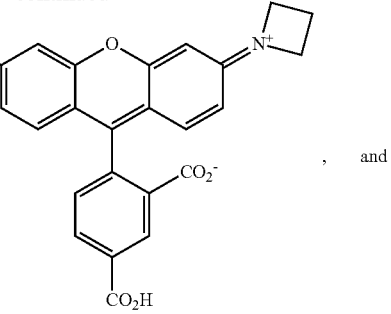

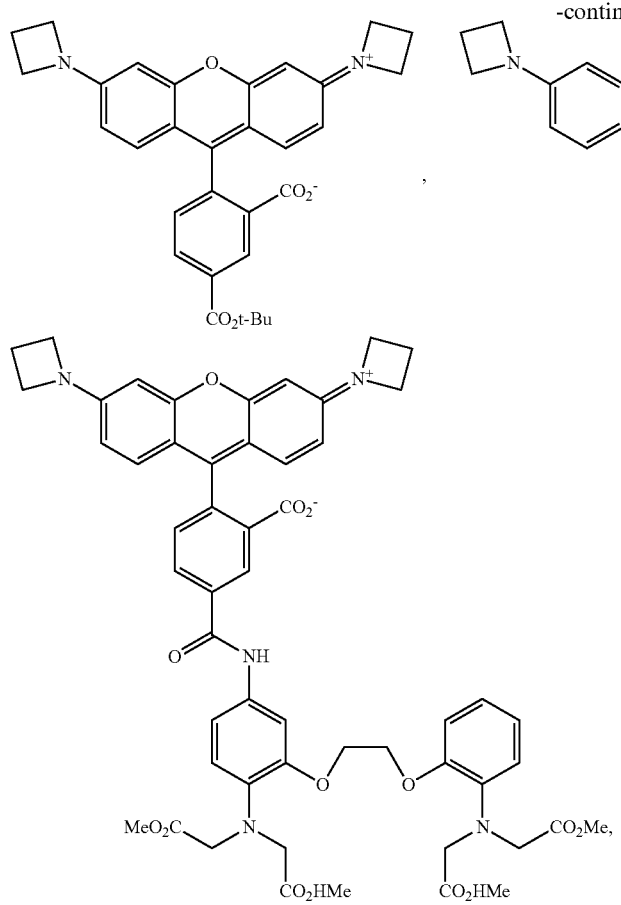

or a zwitterion thereof.

The presently-disclosed subject matter further includes a method of using the compounds described herein. In some embodiments the method comprises utilizing the compound as a reporter for enzyme activity, as a fluorescent tag, as a sensor for a target substance (an analyte), as an agent for imaging experiments, and/or as an imaging agent for super-resolution microscopy.

Some embodiments of the presently-disclosed subject matter include methods for detecting a target sample that comprise contacting a sample with a compound as disclosed herein.

Some embodiments of the presently-disclosed subject matter include methods for detecting a target sample that comprise contacting a sample with a compound as disclosed herein, exposing the sample to light; and detecting an emission, the emission light indicating the presence of calcium.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites, and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a compound" includes a plurality of such compounds, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "absorption wavelength" as used herein refers to the wavelength of light capable of being absorbed by a compound in order to excite the compound to emit a light. The light emitted from a compound that has been excited with an absorption light will have an "emission wavelength."

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "protein" means any polymer comprising any of the 20 protein amino acids, regardless of its size. Although "polypeptide" is often used in reference to relatively large proteins, and "peptide" is often used in reference to small proteins, usage of these terms in the art overlaps and varies. The term "protein" as used herein refers to peptides, polypeptides and proteins, unless otherwise noted.

The term "selectively bind" is used herein to refer to the property of an atom, moiety, and/or molecule preferentially being drawn to or binding a particular compound. In some instances the atom, moiety, and/or molecule selectively binds to a particular site on a compound, such as an active site on a protein molecule.

The term "detect" is used herein to refer to the act of viewing, imagining, indicating the presence of, measuring, and the like a target substance based on the light emitted from the present compounds. More specifically, in some instances the present compounds can be bound to a target substance, and, upon being exposed to an absorption light, will emit an emission light. The presence of an emission light can indicate the presence of a target substance, whereas the quantification of the light intensity can be used to measure the concentration of a target substance.

The term "target substance" refers to a substance that is selectively bound directly by the presently-disclosed compounds and/or indirectly by a molecule that is bound to the present compound. A target substances can include, but is not limited to, a protein, carbohydrates, polysaccharide, glycoprotein, hormone, receptor, antigen, antibody, virus, substrate, metabolite, inhibitor, drug, nutrient, growth factor, and the like. In some embodiments the target substance refers to an entire molecule, and in other embodiments the target substances refers to a site on a molecule, such as a binding site on a particular protein.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless stated otherwise, all chemical groups described herein include both unsubstituted and substituted varieties.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

Where substituent groups are specified by their conventional chemical formula written from left to right, they equally encompass the chemically identical substituents that would result from writing the structure from right to left. For instance, —$CH_2O$— also encompasses recite —$OCH_2$—.

It should be understood that the bond types and locations in the chemical structures provided herein may adapt depending on the substituents in the compound, even if not specifically recited. For instance, -X- where X can be either C or N can refer to, respectively, —$CH_2$— or —NH—, where the lone pair of electrons on N is not illustrated. Thus, even if not specifically illustrated, the chemical compounds described herein include any hydrogen atoms, lone pair of electrons, and the like necessary for completing a chemical structure.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also refer to both substituted or unsubstituted alkyls. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2, 3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3, 4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^1$ or —$OA^1$—$(OA^2)_a$—$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, haide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "ring" as used herein refers to a substituted or unsubstituted cycloalkyl, substituted or unsubstituted heterocycloalkyl, substituted or unsubstituted aryl, or substituted or unsubstituted heteroaryl. A ring includes fused ring moieties, referred to as a fused ring system wherein a ring may be fused to one or more rings selected from a substituted or unsubstituted cycloalkyl, substituted or unsubstituted heterocycloalkyl, substituted or unsubstituted aryl, and substituted or unsubstituted heteroaryl in any combination. The number of atoms in a ring is typically defined by the number of members in the ring. For example, a "5- to 8-membered ring" means there are 5 to 8 atoms in the encircling arrangement. A ring can optionally include a heteroatom. The term "ring" further includes a ring system comprising more than one "ring", wherein each "ring" is independently defined as above.

Some of the unsaturated structures described herein, such as ring structures including cycloalkyl and aryl, are illustrated with dashed bonds to signify the potential existence of a resonance structure. Structures having dashed bonds are intended to reflect every possible configuration of the structure, but does not necessarily imply that all possible structures are in existence. It should be understood that the types of bonds (e.g., single bond, double bond) in such structures will vary depending on the atoms in the structure as well as whether the structures are substituted with one or more additional atoms or moieties.

The term "aldehyde" as used herein is represented by a formula —C(O)H.

Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), N(alkyl)$_2$, and N(aryl)$_2$.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula —($A^1$O(O)C—$A^2$—C(O)O)$_a$— or —($A^1$O(O)C—$A^2$—OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "halide" or "halogen" refers to at least one of the halogens selected from fluorine, chlorine, bromine, and iodine.

The term "thiol" as used herein is represented by a formula —SH.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Example 1: JF-BAPTA

These examples include studies related to the development of an improved version of red-shifted Compound 2 compatible with cellular labeling strategies. To increase brightness, Janelia Fluor 549 ($JF_{549}$) was identified as a fluorophore scaffold in these studies. $JF_{549}$ exhibits a higher fluorescence quantum yield than TMR and has demonstrated utility in live-cell labeling,[19] but has not been used in sensor systems. To increase PeT quenching, the relative position of the fluorophore and the BAPTA moiety was altered. Although the PeT process is complex, the efficiency of this quenching depends partly on the distance between the electron donor and acceptor.[17-18] Thus, decreasing the distance between the BAPTA and xanthene fluorophore should increase the efficiency of PeT in the $Ca^{2+}$-free state, thereby decreasing $F_0$ and increasing $\Delta F/F_0$ of the indicator.[20]

Figure 1B:
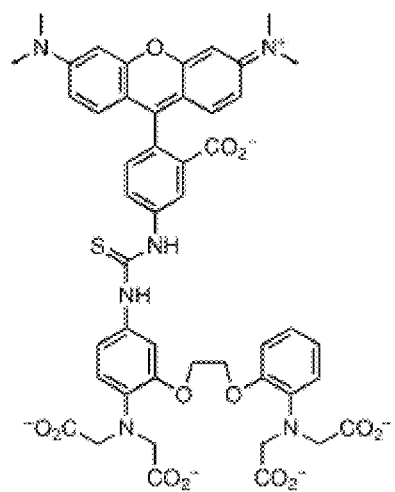
FIG. 1B includes the structure of Calcium Orange (Compound 2).
Figure 2D:
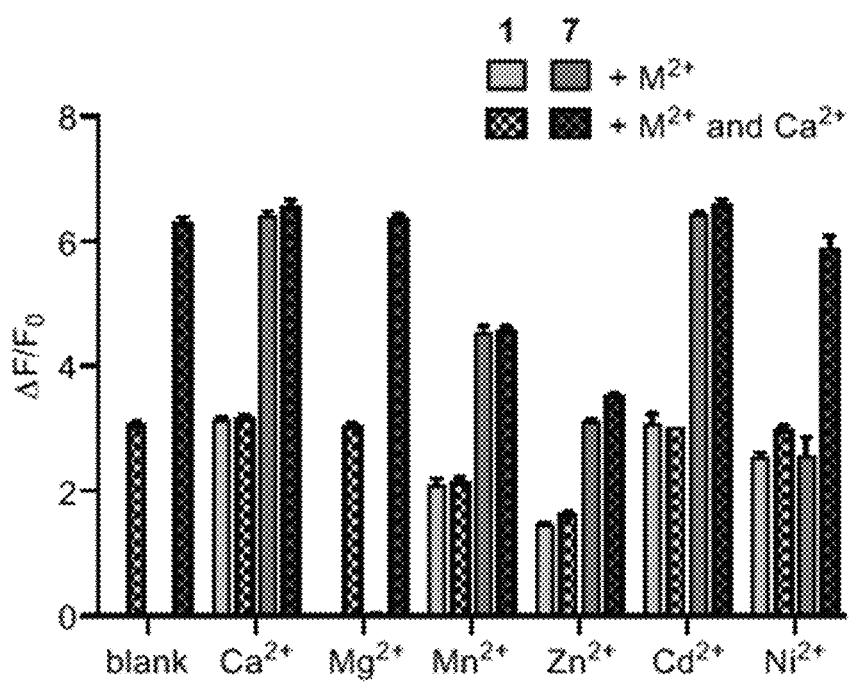
FIG. 2D is a graph illustrating the selectivity of 1 and 7 for $Ca^{2+}$ compared to other divalent cations. The $\Delta F/F_0$ of a 1 μM solution of 1 or 7 was measured under two conditions: (i) buffer (30 mM MOPS, 100 mM KCl, pH=7.2) containing 10 μM of EGTA to bind background free Ca2+ and 60 equivalents of a divalent cation (Ca2+, Mg2+, Mn2+, Zn2+, Cd2+, and Ni2+; solid bars); (ii) the same conditions with the further addition of 60 equivalents of Ca2+(patterned bars) to measure displacement. Error bars represent standard deviation, n=2; fluorescence emission was measured at 520 nm for 1 and 570 nm for 7.
Figure 9:
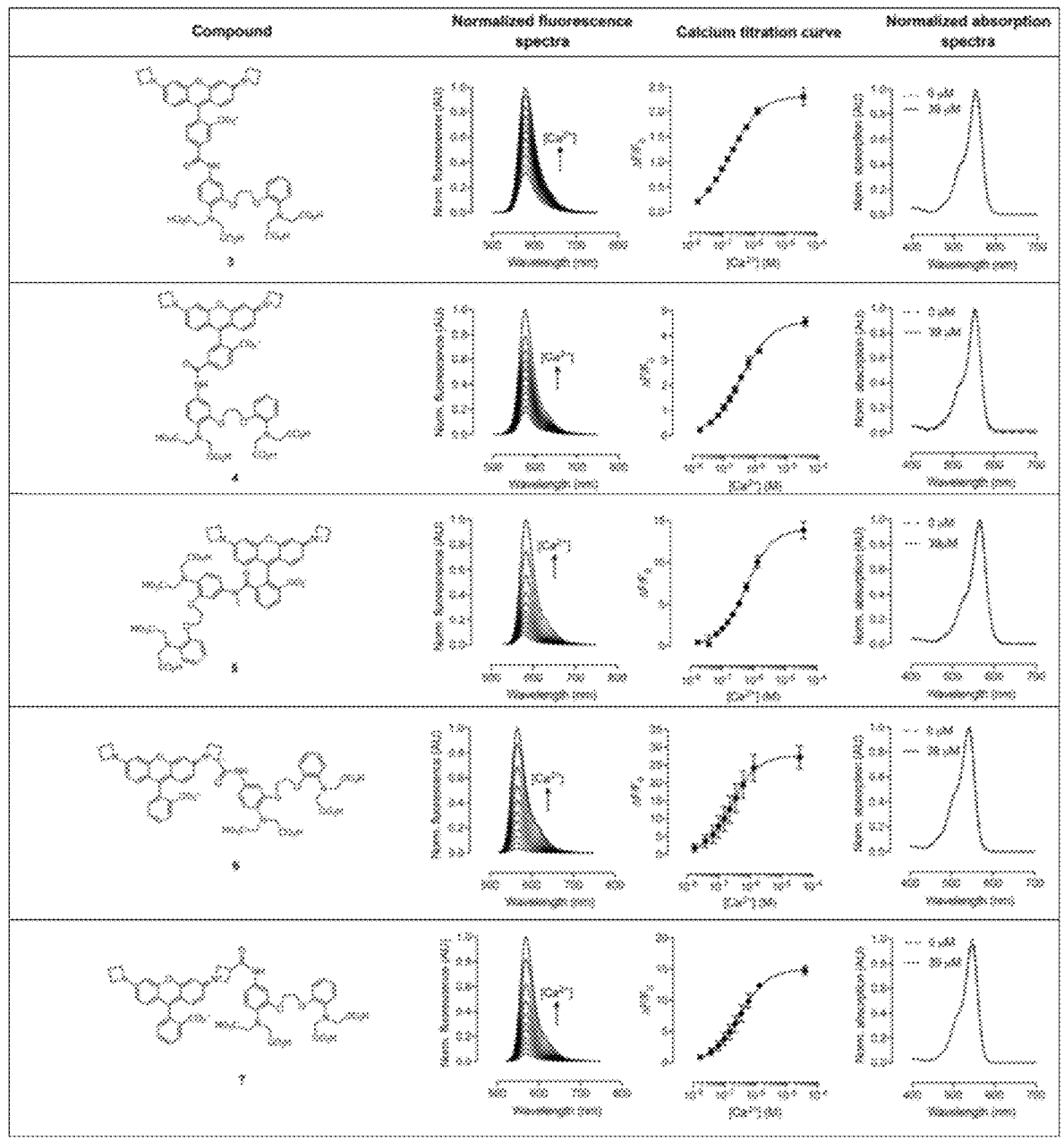
FIG. 9 includes a table showing fluorescence spectra, calcium titration curves and absorption spectra for all calcium indicators. Free calcium concentration in the buffers vary from 0 to 39 μM.

To test these hypotheses, BAPTA was attached to the 5-position of $JF_{549}$ to yield 3 (FIG. 2a); this is the direct analog of indicators 1 and 2. Compound 3 showed similar $Ca^{2+}$ sensitivity to 2 ($\Delta F/F_0$=2.3; $K_d$=190 nM, FIG. 2B, FIG. 2D, Table of FIG. 9) but a higher $\Phi_{sat}$=0.69, which confirmed that the high brightness of $JF_{549}$ is retained when this dye is incorporated into an $Ca^{2+}$ indicator. Next, a systematic isomeric tuning study was conducted, synthesizing compounds 4-7, which incorporate the BAPTA at different positions of the $JF_{549}$ molecule (FIG. 2a). Standard amide coupling conditions were used to attach the BAPTA moiety to various carboxy-$JF_{549}$ derivatives. For the 7-carboxy-$JF_{549}$ derivative 5, an N-methyl group was introduced on the BAPTA moiety to prevent formation of the nonfluorescent lactam. These compounds were characterized in vitro and all showed a fluorescence increase upon binding $Ca^{2+}$ (FIG. 1b, Table of FIG. 9, Table 1).

The spectral properties of these dyes were examined in detail. The isomeric tuning elicited only minor changes in $\lambda_{max}$ (542-565 nm) and $\lambda_{em}$ (566-583 nm). The structural modifications had substantial effects on $\Delta F/F_0$ and $\Phi_{sat}$, however; $\Delta F/F_0$ increased as the BAPTA-xanthene distance decreased and $\Phi_{sat}$ showed more complicated behavior. The 6-isomer 4 showed a 2-fold improvement in $\Delta F/F_0$ compared to 3, and a higher quantum yield ($\Phi_{sat}$=0.78), supporting the hypothesis that placing the BAPTA closer to the fluorophore could improve indicator performance. The sensitivity of 5 was even higher ($\Delta F/F_0$=14), but the quantum yield was substantially reduced ($\Phi_{sat}$=0.18). This result suggests that the close proximity of the BAPTA on the 7-position of the fluorophore increases PeT quenching even in the presence of saturating $Ca^{2+}$. A similar effect was observed for compound 6 ($\Delta F/F_0$=27.7, $\Phi_{sat}$=0.45), where the BAPTA is attached to the 2-position of the azetidine to give a diastereomeric mixture. Attaching the BAPTA at the 3-position of the azetidine to give 7 removed stereochemistry concerns and resulted in a satisfying compromise between brightness and sensitivity: $\Delta F/F_0$=15.0; $\Phi_{sat}$=0.75. These values are similar to compound 1 but with $\lambda_{ex}$ and $\lambda_{em}$ red-shifted by 50 nm. The properties of symmetrical structures were investigated based on either two BAPTA moieties (8) or two $JF_{549}$ fluorophores (9; Table of FIG. 9, Table 1). These compounds showed higher $\Delta F/F_0$ values but substantially lower affinity ($K_d$, >0.7 µM) making them less suitable for cytosolic $Ca^{2+}$ measurements.

TABLE 1

In vitro properties of all known calcium indicators 1-2 and novel compounds 3-9, 12, 12$_{HT}$, 13, and 13$_{HT}$

| Compound | Name | $\lambda_{max}/\lambda_{em}$ (nm) | $\phi_{sat}$ | $\Delta F/F_0$ | $K_d$ (µM) |
|---|---|---|---|---|---|
| 1 [15] | Oregon Green BAPTA | 492/523 | 0.70 | 14 | 0.170 |
| 2 [15] | Calcium Orange | 549/574 | 0.33 | 3 | 0.185 |
| 3 | | 554/579 | 0.69 | 2.3 | 0.19 |
| 4 | | 555/576 | 0.78 | 4.6 | 0.35 |

TABLE 1-continued

In vitro properties of all known calcium indicators 1-2 and
novel compounds 3-9, 12, $12_{HT}$, 13, and $13_{HT}$

| Compound | Name | $\lambda_{max}/\lambda_{em}$ (nm) | $\Phi_{sat}$ | $\Delta F/F_0$ | $K_d$ ($\mu M$) |
|---|---|---|---|---|---|
| 5 | | 565/583 | 0.18 | 14.0 | 0.57 |
| 6 | | 542/566 | 0.45 | 27.7 | 0.27 |
| 7 | $JF_{549}$-BAPTA | 546/569 | 0.75 | 15.0 | 0.31 |
| 8 | | 543/566 | 0.70 | 47.0 | 0.73 |
| 9 | | 512-549/570 | 0.20 | 75.0 | ~5 |
| 12 | $JF_{549}$-BAPTA-HaloTag ligand | 550/574 | 0.74 | 13.8 | 0.29 |
| $12^{HT}$ | | 553/573 | 0.78 | 9.5 | 0.13 |
| 13 | $JF_{646}$-BAPTA-HaloTag ligand | 646/666 | 0.58 | 7.8 | 0.28 |
| $13_{HT}$ | | 650/665 | 0.55 | 5.5 | 0.14 |

Example 2: JF-BAPTA-AM

Figure 3A:
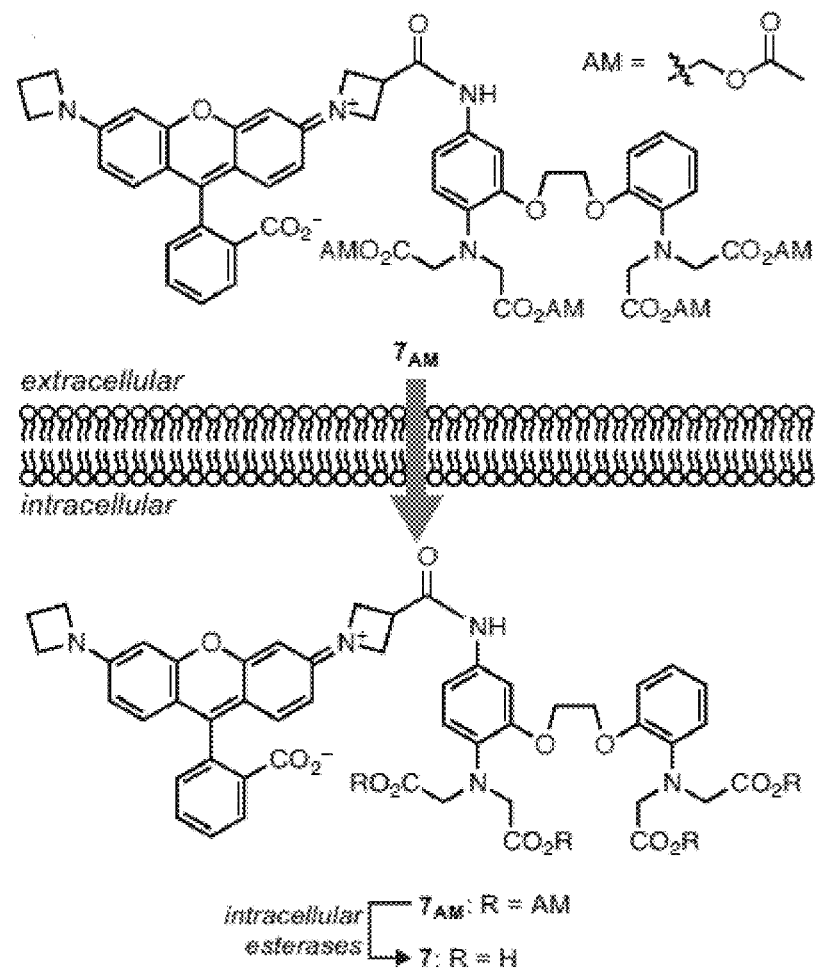
FIG. 3A includes schematic showing Compound $7_{AM}$ crossing the cell membrane followed by cleavage of the AM groups by esterases to yield Compound 7.
Figures 3B, 3C, 3D:
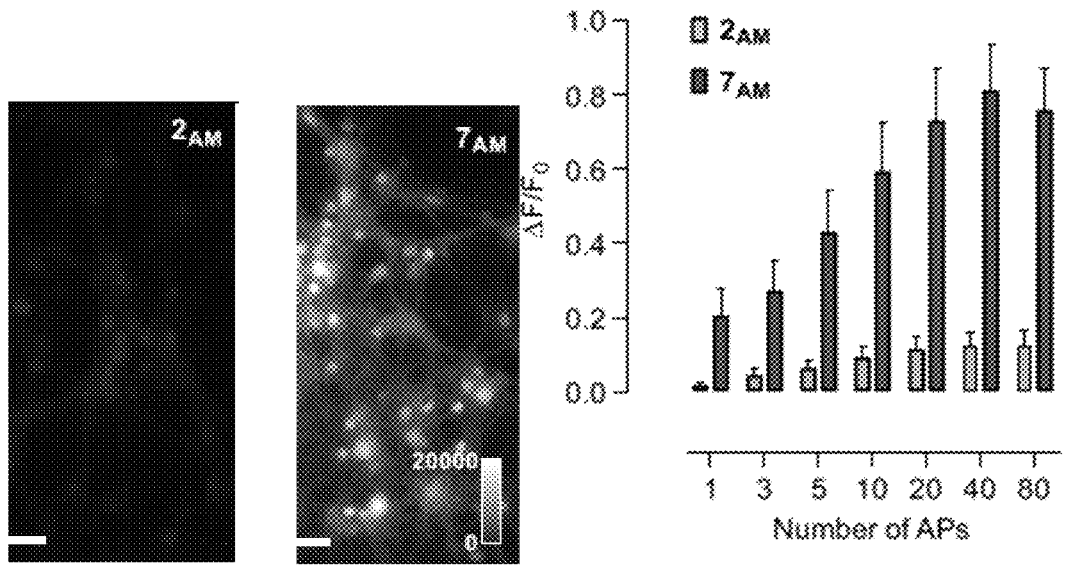
FIGS. 3B and 3C include representative wide-field fluorescence microscopy images of cultured hippocampal neurons loaded with Compound $2_{AM}$ (FIG. 3B) or $7_{AM}$ (FIG. 3C).
FIG. 3D includes a plot of $\Delta F/F_0$ of Compound $2_{AM}$ (gray) and $7_{AM}$ (red) vs. number of stimulated APs in cultured neurons.
Figure 4A:
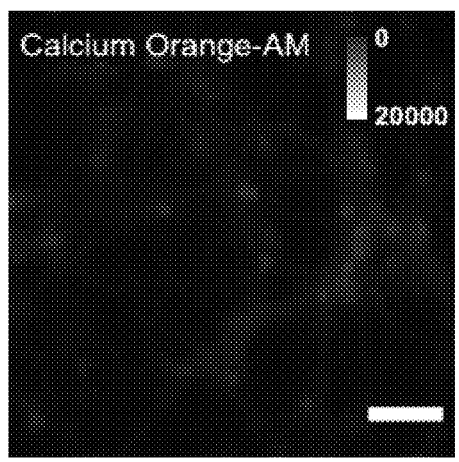
FIGS. 4A and 4B include images of cultured hippocampal neurons labeled with $2_{AM}$ (1 μM, 30 min) at different displays (0-20000 (FIG. 4A), and 0-3000 (FIG. 4B).
Figure 4B:
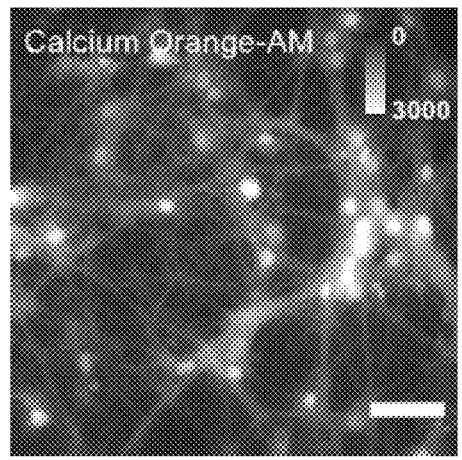
Figure 4C:
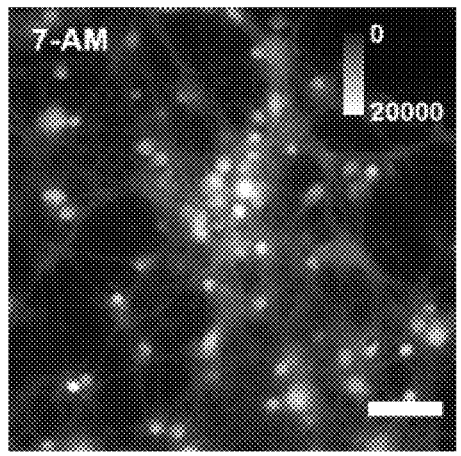
FIG. 4C includes an image of cultured hippocampal neurons labeled with $7_{AM}$ (1 M, 30 min) at 0-20000 display.
Figure 4D:
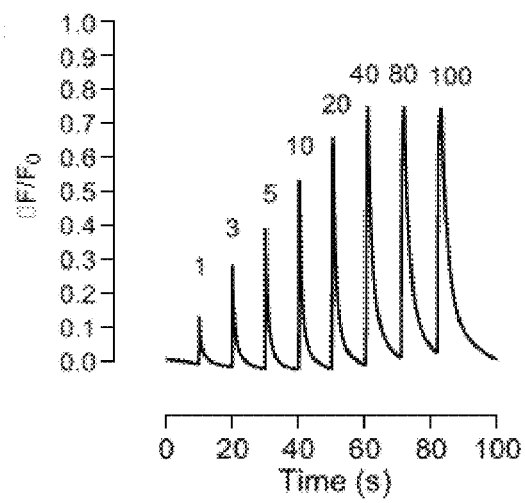
FIG. 4D includes a graph illustrating average fluorescence response of $7_{AM}$ in neurons (50 neurons, 3 wells) stimulated with 1,3, 5, 10, 20, 40, 80 and 100 APs.

Based on these results, compound 7 ($^1JF_{549}$-BAPTA$^1$) was selected and the cell-permeant tetra-acetoxymethyl (AM) ester derivative $7_{AM}$ was prepared. This compound enabled noninvasive loading of cultured hippocampal neurons, followed by cleavage of the AM groups by intracellular esterases to trap the molecule in the cell and recover the $Ca^{2+}$-responsive 7 (FIG. 3a). The performance of $7_{AM}$ was compared to the commercially available Calcium Orange AM ($2_{AM}$) in cultured primary neurons; both showed nuclear accumulation after 30 min incubation and washing by media exchange (FIG. 3b,c, FIG. 4). Fluorescence increase was quantified in response to calcium flux by electrically stimulating the neurons to induce discrete numbers of action potentials (APs).[21] Despite the undesirable nuclear localization, small changes in [$Ca^{2+}$] in cells loaded with $7_{AM}$ could be detected, demonstrating single AP sensitivity ($\Delta F/F_0 =0.20$), and saturating at 40 APs with a maximal $\Delta F/F_0=0.80$(FIG. 3d, FIG. 4c). In all, neurons loaded with $7_{AM}$ were 10× brighter with 10× higher $\Delta F/F_0$ compared to cells loaded with $2_{AM}$.

Example 3: JF-BAPTA-Tag

Figure 5A:
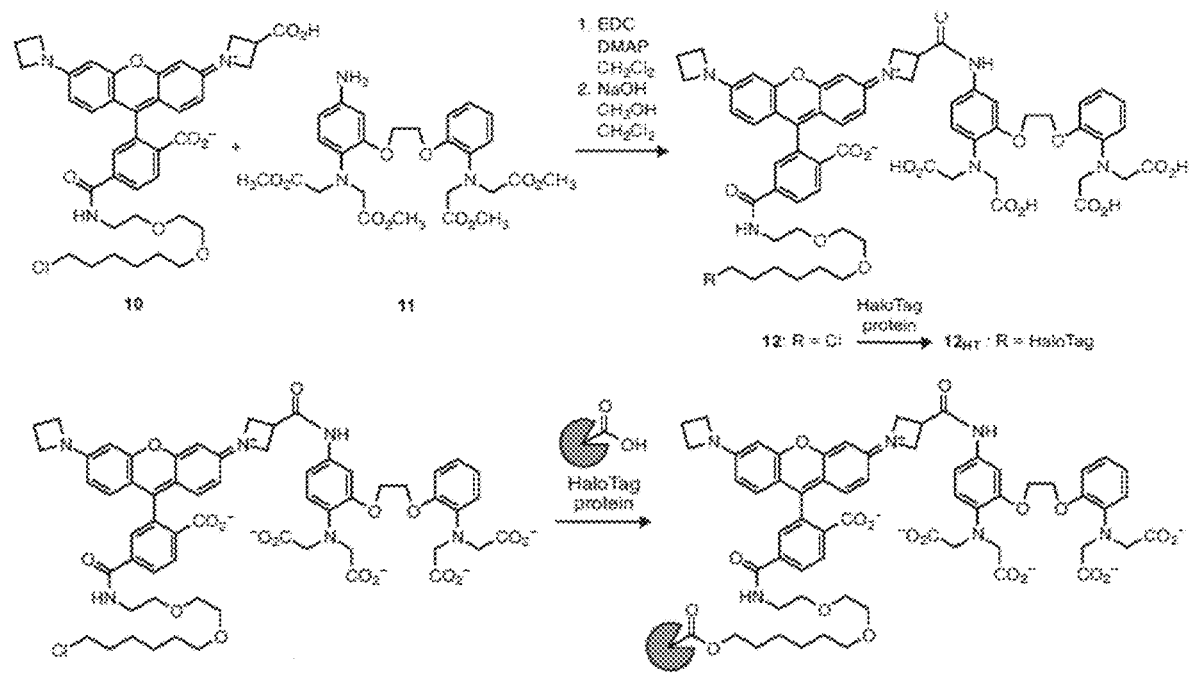
FIG. 5A includes the synthesis of ligand 12 and formation of 12HT HaloTag protein conjugate.
Figure 5B:
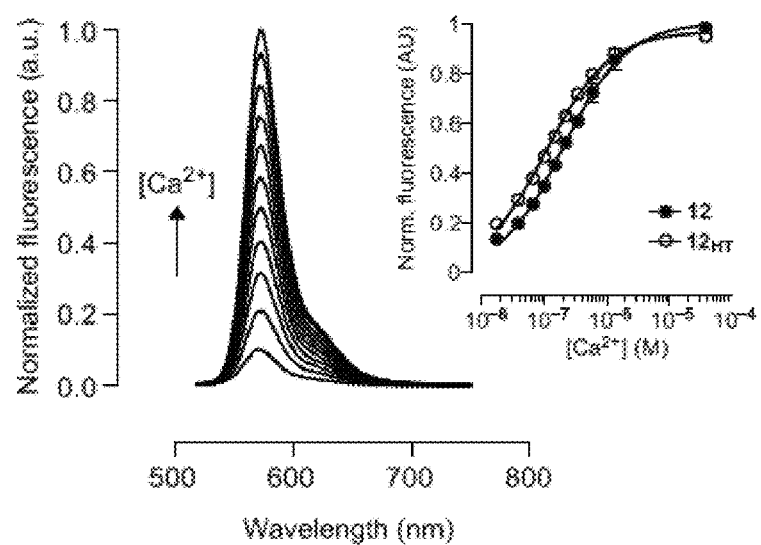
FIG. 5B includes a graph illustrating $Ca^{2+}$-dependent change in fluorescence emission of 12HT and $Ca^{2+}$ titrations of Compounds 12 and 12HT (inset).
Figure 5C:
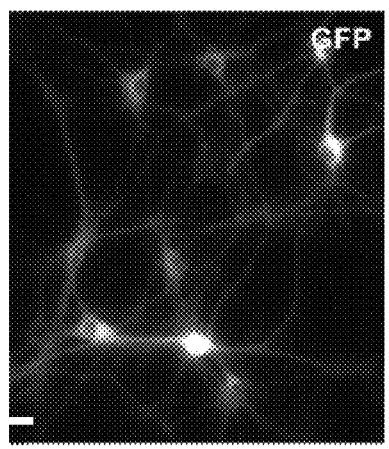
FIGS. 5C-5E include representative wide-field fluorescence images of cultured hippocampal neurons expressing NES-HaloTag-GFP labeled with 10AM.

A targetable version of this bright and sensitive $JF_{549}$-BAPTA was developed to extend its use in genetically defined cells. HaloTag is an enzyme engineered to bind rapidly, selectively, and irreversibly to a chloroalkane ligand.[22-23] Utilization of the azetidine ring in $JF_{549}$ as the attachment point for the BAPTA allowed incorporation of the HaloTag ligand at the optimal[23] 6-position on the pendant aromatic ring. The carboxy-containing $JF_{549}$-HaloTag ligand (10) and $H_2N$-BAPTA tetramethyl ester (11) were coupled, followed by saponification to yield $JF_{549}$-BAPTA-HaloTag ligand (12; FIG. 5a). The free HaloTag ligand showed comparable fluorescence properties to the parent compound ($\Delta F/F_0=14$, $\Phi_{sat}=0.74$) and binding to purified HaloTag protein to give $12_{HT}$ resulted in a slightly lower sensitivity ($\Delta F/F_0=9$) and unchanged $\Phi_{sat}$ (FIG. 5b).

Figure 5D:
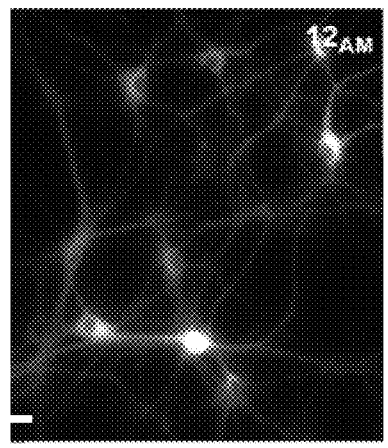
Figure 5E:
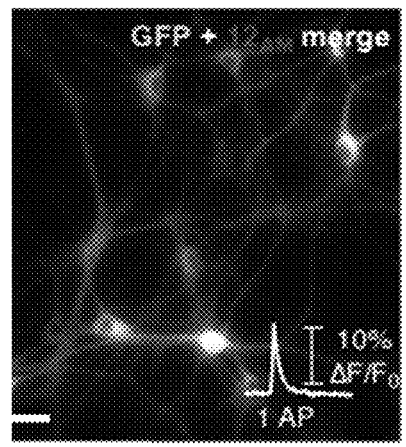
Figure 5F:
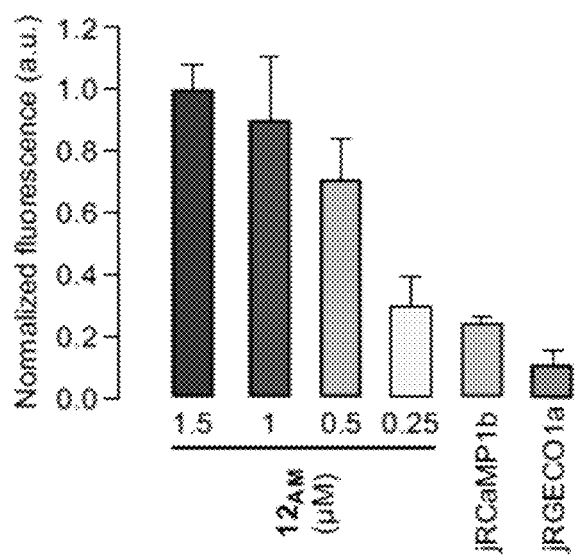
FIG. 5F includes a graph showing relative resting cellular fluorescence in neurons expressing NES-HaloTag-GFP loaded with different concentrations of 12AM compared to signal from neurons expressing NES-jRCaMP1b-GFP or NES-jRGECO1 a-GFP.
Figure 6A:
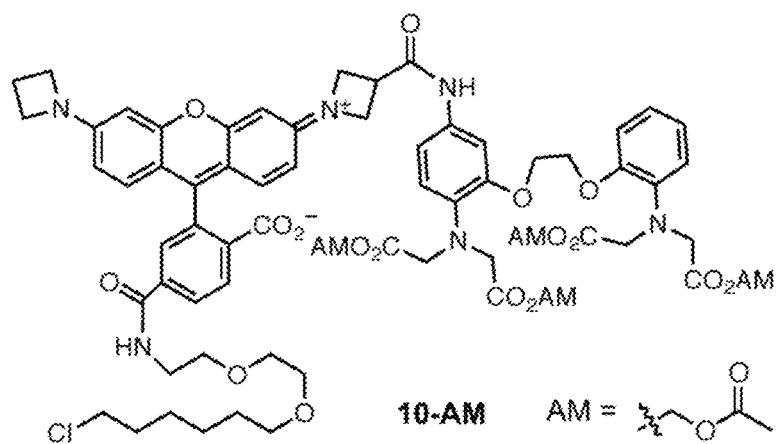
FIG. 6A includes the structure of cell-permeant ligand $12_{AM}$.
Figure 6B:
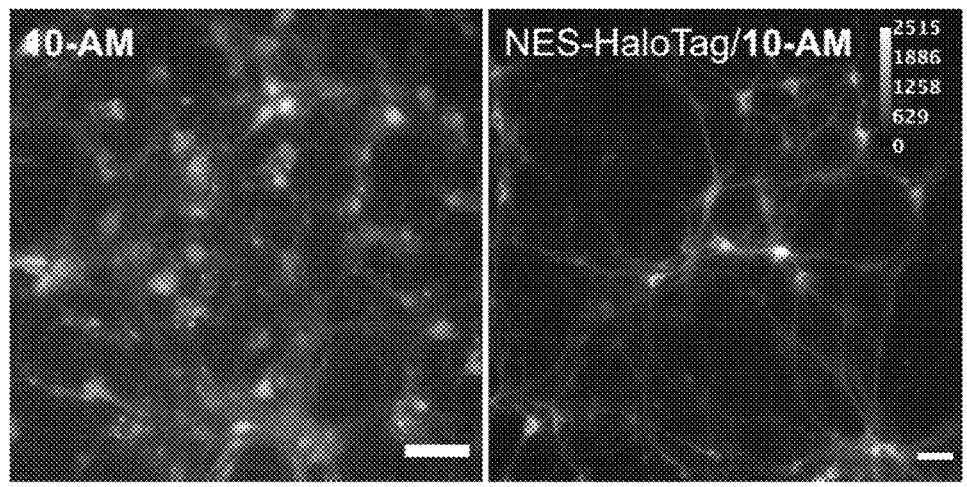
FIG. 6B includes images of cultured rat hippocampal neurons labeled with $12_{AM}$ (1 μM, 2 h) control and in neurons expressing NES-HaloTag-GFP.

The AM ester derivative was synthesized using the same synthetic strategy ($12_{AM}$; FIG. 6a) and tested this molecule in cells. In mock transfected cultured hippocampal neurons $12_{AM}$ showed a similar nuclear accumulation to the parent compound $7_{AM}$ (FIG. 6b). In cells expressing HaloTag-GFP fusion bearing a N-terminal nuclear exclusion sequence (NES), however, the sensor showed excellent colocalization with HaloTag with low background in the nucleus (FIG. 5d,e) with an optimal labeling concentration of 1 µM for 30 min (FIG. 5f). This demonstrates that 12 is a suitable HaloTag ligand and the HaloTag localization can overcome the inherent subcellular localization of this small-molecule in live-cell experiments. Compound $12_{AM}$ is a net-neutral, zwitterionic rhodamine, which does not show the inherent mitochondrial localization that has plagued many cationic rosamine-based $Ca^{2+}$ indicators.[11, 24]

Figure 5G:
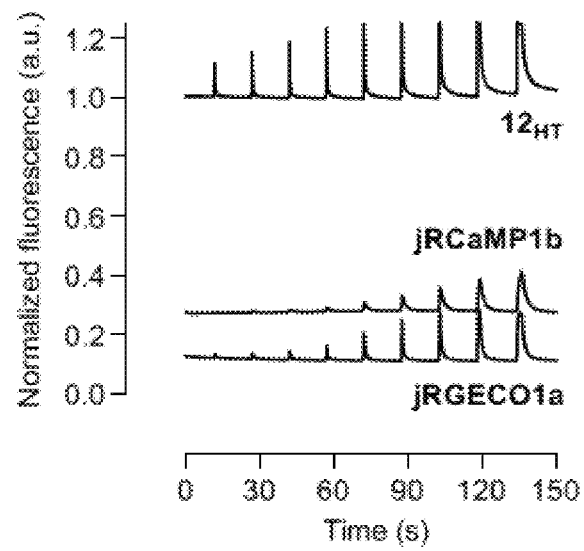
FIG. 5G is a graph illustrating the average normalized fluorescence signal in neurons expressing: HaloTag labeled with 12AM to give 12HT, jRCaMP1b, or jRGECO1a stimulated with 1, 2, 3, 5, 10, 20, 40, 80, and 160 APs; all traces were linearly corrected for photobleaching.
Figure 6C:
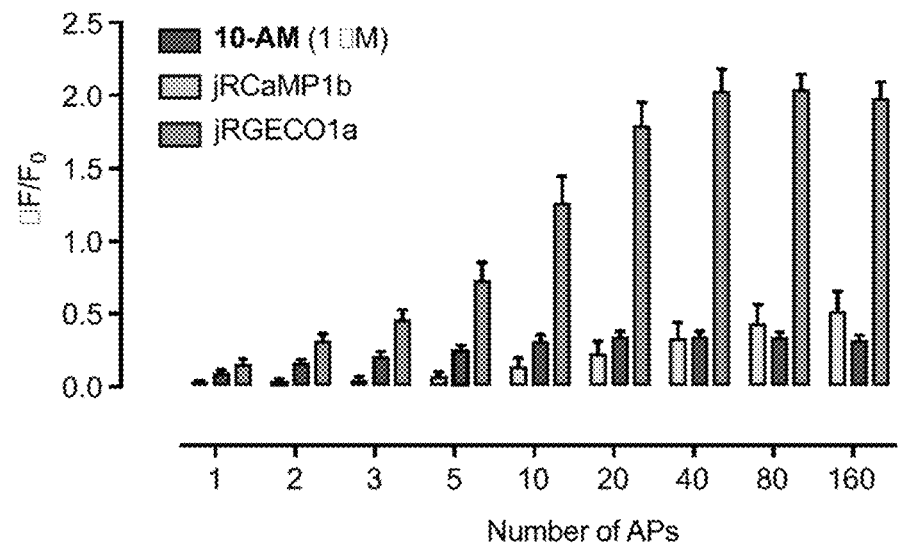
FIG. 6C includes a plot of $\Delta F/F_0$ of $12_{AM}$ (85 neurons, 3 wells), jRCaMP1b (74 neurons, 3 wells) and jRGECO1a (59 neurons, 3 wells) vs. number of stimulated APs.

The targeted sensor was compared to the red-shifted GECIs jRGECO1a and jRCaMP1b (FIG. 5f,g).[6] Like the HaloTag protein, these GECIs were expressed in cultured neurons with a NES and GFP fusion to normalize for protein expression levels. The baseline fluorescence of cells expressing NES-HaloTag-GFP labeled with $12_{AM}$ was 7.8-fold brighter than jRGECO1a and 3.6-fold brighter than jRCaMP1b under the same imaging conditions. The fluorescence response to evoked Aps was measured. HaloTag-bound 12 was able to detect single AP with $\Delta F/F_0=0.10$ and saturated at 20 APs, with a maximal $\Delta F/F_0=0.35$ (FIG. 5g). The superior brightness of $12_{HT}$ yields a higher signal at both resting calcium level and upon stimulation making it ideal for measurement of single APs. In contrast, jRGECO1a and jRCaMP1b exhibited better sensitivity at higher numbers of APs (FIG. 6c).

Figure 7A:
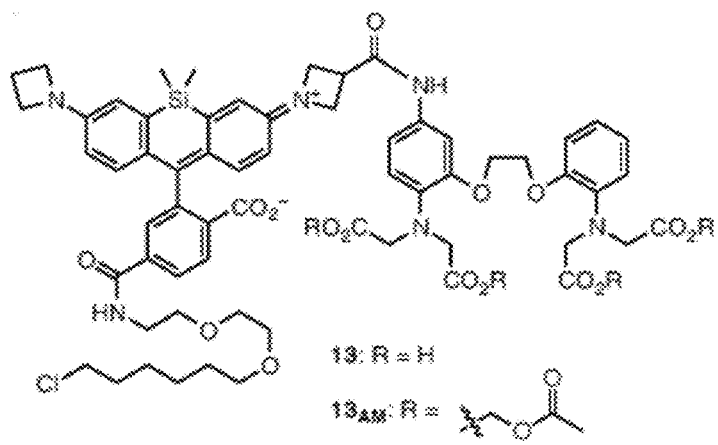
FIG. 7A includes the structures of Compounds 13 and 13AM.
Figure 7B:
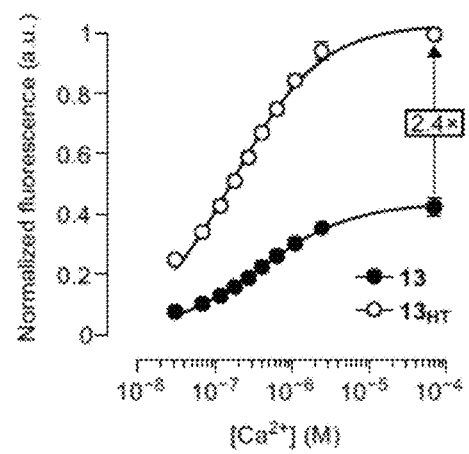
FIG. 7B includes calcium titrations of 13 and 13HT.
Figure 7C:
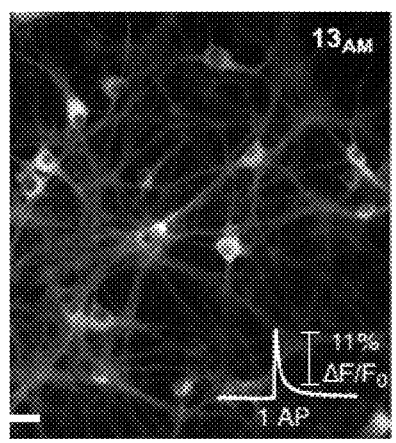
FIG. 7C includes a representative wide-field fluorescence image of cultured hippocampal neurons expressing NES-HaloTag-GFP labeled with 13AM (1 PM, 30 min) and average response to 1 AP (overlay); scale bar: 50 μm.

This approach was extended to a far-red targetable indicator, and transferred the design of 12 to the bright, red-shifted Si-rhodamine $JF_{646}$.[19] Si-rhodamines ligands are often fluorogenic upon binding to the HaloTag protein, which decreases background signal from unbound dye. $JF_{646}$-BAPTA-HaloTag ligand 13 was synthesized and calcium titrations were performed in the presence or absence of excess HaloTag protein in vitro (FIG. 7a,b). 13 was modestly fluorogenic, with a 2.4-fold increase in fluorescence upon binding to HaloTag in the presence of saturating [$Ca^{2+}$]. In cultured hippocampal neurons, the cell-permeant $13_{AM}$ showed excellent colocalization with NES-HaloTag-GFP and similar sensitivity to the $JF_{549}$ variant: $\Delta F/F_0=0.11$ for 1 AP (FIG. 7c, FIG. 8).

Figure 7D:
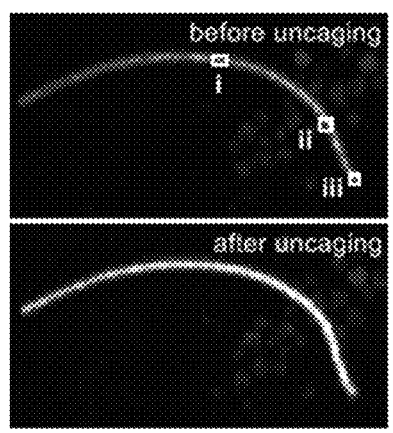
FIG. 7D includes maximum intensity projection images of primary cilium in hRPE1 cells expressing 5HT6-HaloTag labeled with 13AM before (top) and after (bottom) calcium uncaging; scale bars: 1 μm.
Figure 7E:
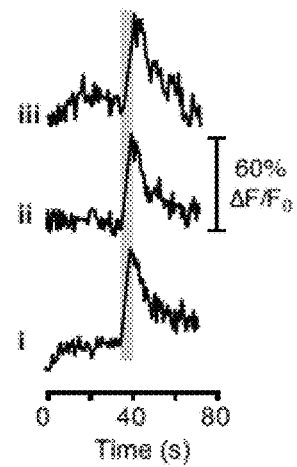
FIG. 7E includes fluorescence traces for the ROIs drawn in d; the gray bar indicates duration and timing of 405 nm light for $Ca^{2+}$ uncaging.
Figure 8A:
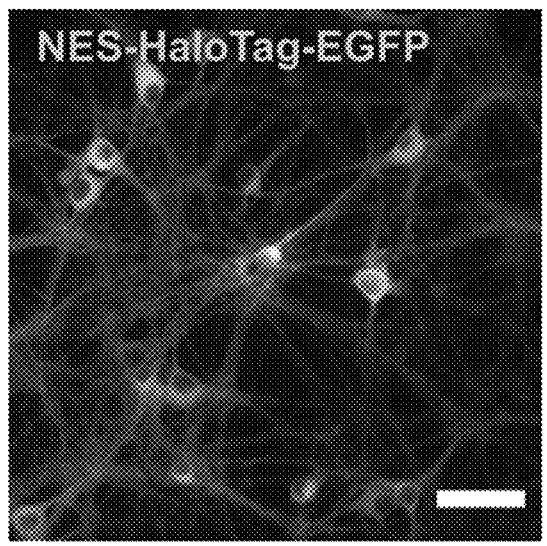
FIG. 8A-8C include images of cultured hippocampal neurons expressing NES-HaloTag-GFP labeled with $13_{AM}$ (1 μM, 2 h). GFP signal (FIG. 8A), $13_{AM}$ (FIG. 8B) and merge (FIG. 8C); scale bars: 50 μm.
Figure 8B:
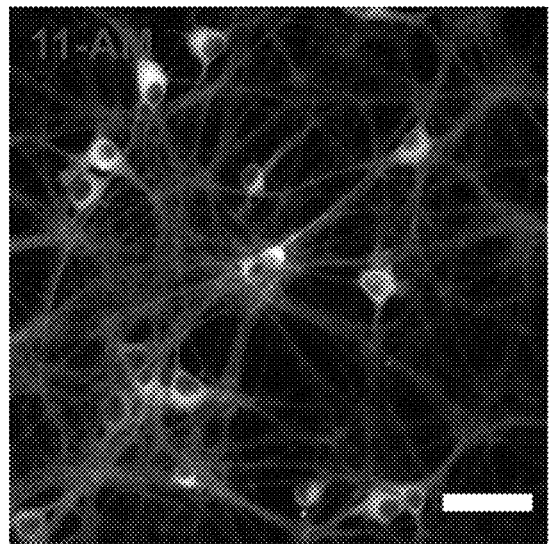
Figure 8C:
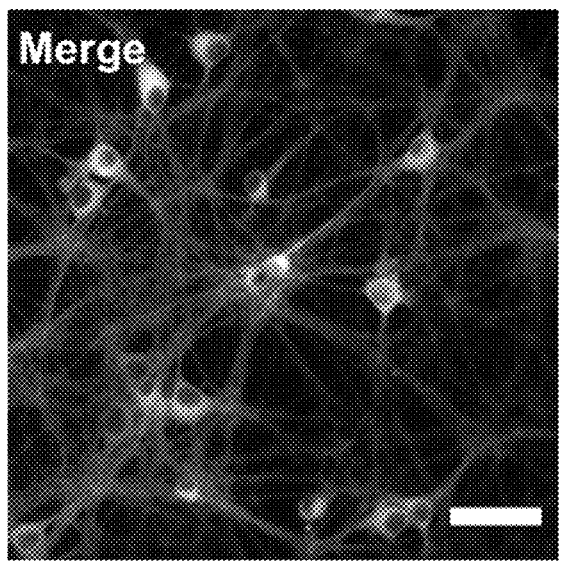
Figure 8D:
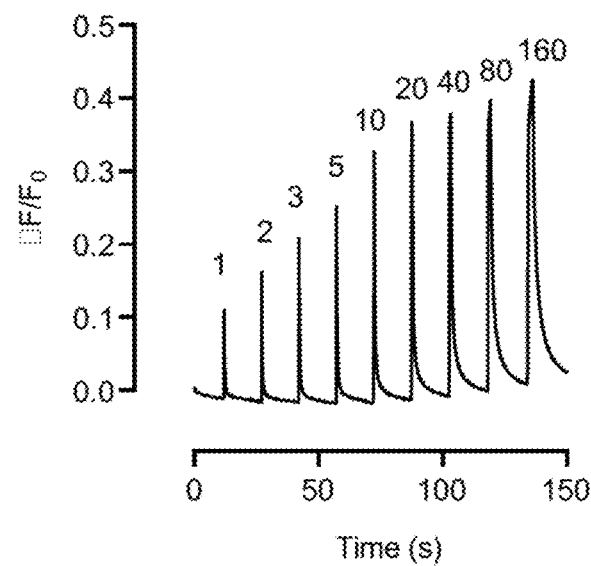
FIG. 8D includes a graph illustrating average response of $13_{AM}$ in neurons (84 neurons, 4 wells) stimulated with 1, 2, 3, 5, 10, 20, 40, 80 and 160 APs.

It was then investigated whether this bright, far-red sensor system could be used to monitor calcium fluctuations in small subcellular locations. The primary cilium, a small organelle present in nearly all eukaryotic cells and involved in diverse signaling pathways.[25] This small cellular region is contiguous with the cytosol making it difficult to load selectively using extant synthetic indicators. Calcium imaging in the cilium also requires a bright reporter due to its submicron diameter and small volume. A stable hRPE1 cell line was generated expressing HaloTag fused to 5-hydroxytryptamine receptor isoform 6 ($5HT_6$), which selectively targets the cilium. Loading with $13_{AM}$ resulted in bright, specific labeling of the primary cilium, confirming the labeling specificity (FIG. 7d). Calcium was uncaged at the base of the cilium with o-nitrophenyl-$EGTA_{AM}$ using brief illumination with 405 nm light.[26] The localized indicator allowed visualization of intra-ciliary $Ca^{2+}$ fluxes with large increases in fluorescence ($\Delta F/F_0=0.60$) across the entire cilium (FIG. 7d, e,).

Example 4: Synthesis

Commercial reagents were obtained from reputable suppliers and used as received. All solvents were purchased in septum-sealed bottles stored under an inert atmosphere. Reaction under inert atmosphere were sealed with septa through which an argon atmosphere was introduced. Reactions were conducted in round-bottomed flasks or septum-capped crimp-top vials containing Teflon-coated magnetic stir bars. Heating of reactions was accomplished with an aluminum reaction block on top of a stirring hotplate equipped with an electronic contact thermometer to maintain the indicated temperatures.

Reactions were monitored by thin layer chromatography (TLC) on precoated TLC glass plates (silica gel 60 $F_{254}$, 250 μm thickness) or by LC-MS (Phenomenex Kinetex 2.1 mm×30 mm 2.6 m C18 column; 5 to 10 μL injection; 5-98% MeCN/$H_2O$, linear gradient, with constant 0.1% v/v $HCO_2H$ additive; 6 min run; 0.5 mL/min flow; ESI; positive ion mode). TLC chromatograms were visualized by UV illumination or developed with ceric ammonium molybdate or KMnO4 stain. Reaction products were purified by flash chromatography on an automated purification system using pre-packed silica gel columns or by preparative HPLC (Phenomenex Gemini-NX 30×150 mm 5 μm C18 column). Analytical HPLC analysis was performed with an Agilent Eclipse XDB 4.6×150 mm 5 μm C18 column under the indicated conditions. High-resolution mass spectrometry was obtained from the High Resolution Mass Spectrometry Facility at the University of Iowa.

With reference to the Appendix, NMR spectra were recorded on a 400 MHz spectrometer. Deuterated solvents were used as purchased except $CDCl_3$ which was neutralized by passing on a short basic $Al_2O_3$ column prior to use for NMR spectra of BAPTA containing compounds. $^1H$ and $^{13}C$ chemical shifts (δ) were referenced to TMS or residual solvent peaks, and $^{19}F$ chemical shifts (δ) were referenced to $CFCl_3$. Data for $^1H$ NMR spectra are reported as follows: chemical shift (δ ppm), multiplicity (s=singlet, d=doublet, t=triplet, q=quartet, p=pentuplet, dd=doublet of doublets, dt=doublet of triplets, m=multiplet, br s=broad signal), coupling constant (Hz), integration. Data for $^{13}C$ NMR spectra are reported by chemical shift (δ ppm) with hydrogen multiplicity (C, CH, $CH_2$, $CH_3$) information obtained from DEPT spectra.

Example 5: Synthesis of Exemplary Compounds Including Compound 3

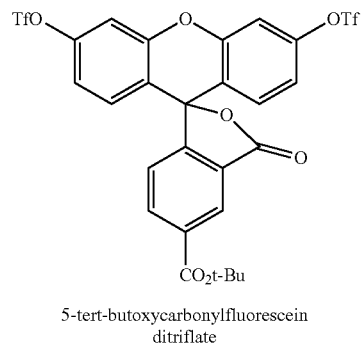

5-tert-butoxycarbonylfluorescein ditriflate

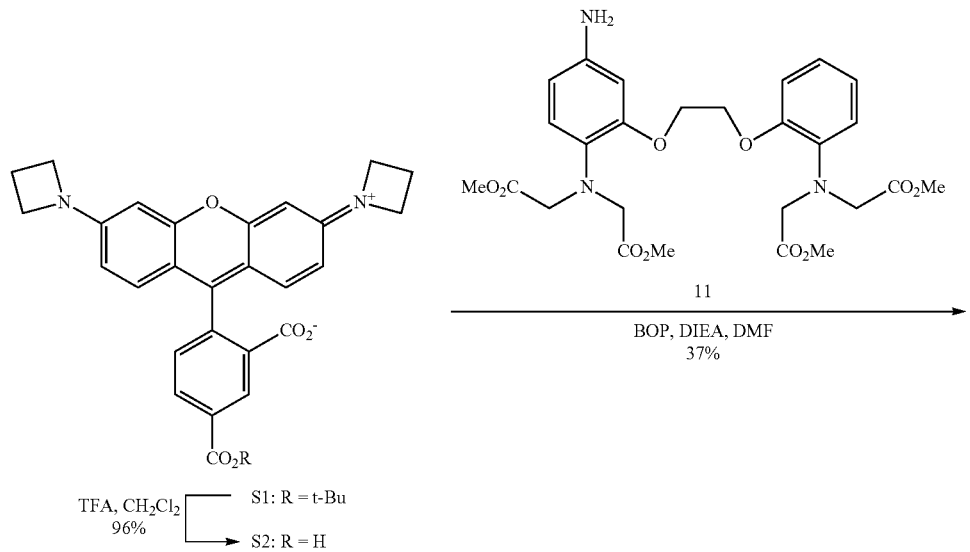

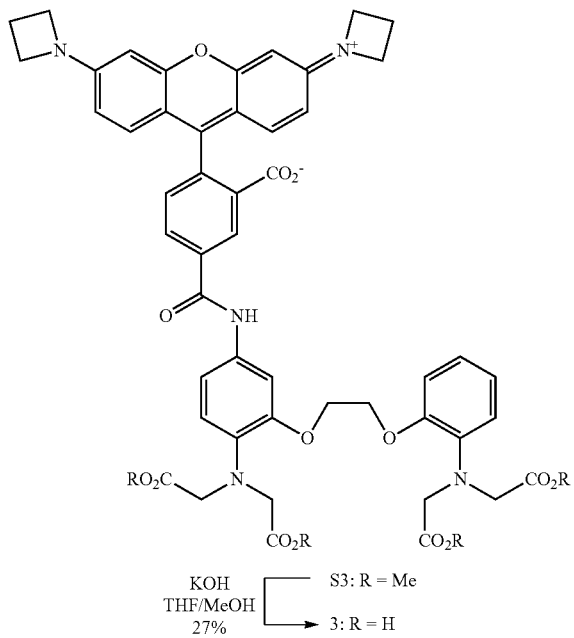

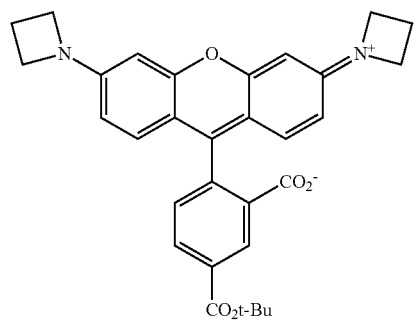

5-tert-butoxycarbonyl-JF$_{549}$ (S1): A vial was charged with 5-tert-butoxycarbonylfluorescein ditriflate[4] (350 mg, 0.502 mmol), Pd$_2$dba$_3$ (46 mg, 0.0502 mmol, 0.1 eq), XPhos (72 mg, 0.151 mmol, 0.3 eq), and Cs$_2$CO$_3$ (458 mg, 1.41 mmol, 2.8 eq). The vial was sealed under argon. Dioxane (4 mL) and then azetidine (82 μL, 1.21 mmol, 2.4 eq) were added. The reaction was stirred at 100° C. for 18 h. It was subsequently cooled to room temperature, diluted with MeOH, deposited onto Celite and concentrated to dryness. Purification by silica gel chromatography (0-10% MeOH (2 M NH$_3$)/CH$_2$Cl$_2$, linear gradient) provided S1 as a pink solid (138 mg, 54%). $^1$H NMR (CDCl$_3$, 400 MHz) δ 8.58 (t, J=1.1 Hz, 1H), 8.26 (dd, J=8.0, 1.5 Hz, 1H), 7.22-7.20 (m, 1H), 6.52 (d, J=8.6 Hz, 2H), 6.19 (d, J=2.3 Hz, 2H), 6.07 (dd, J=8.6, 2.3 Hz, 2H), 3.90 (t, J=7.3 Hz, 8H), 2.41-2.34 (m, 4H), 1.63 (s, 9H); $^{13}$C NMR (CDCl$_3$, 101 MHz) δ 169.1 (C), 164.5 (C), 156.9 (C), 153.7 (C), 152.8 (C), 135.7 (CH$_3$), 133.8 (C), 128.8 (CH$_3$), 127.9 (C), 126.4 (CH$_3$), 124.3 (CH$_3$), 107.8 (CH$_3$), 107.1 (C), 97.7 (CH$_3$), 82.3 (C), 52.2 (CH$_2$), 28.3 (CH$_3$), 16.8 (CH$_2$); HRMS (ESI) calcd for C$_{31}$H$_{31}$N$_2$O$_5$ [M+H]$^+$ 511.2233, found 511.2232.

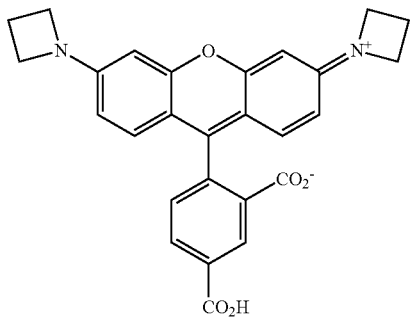

5-carboxy-JF$_{549}$ (52): S1 (110 mg, 0.215 mmol) was taken up in CH$_2$Cl$_2$ (4 mL) and trifluoroacetic acid (0.8 mL) was added. The reaction was stirred at room temperature for 4 h. Toluene (3 mL) was added, the reaction mixture was concentrated to dryness and then azeotroped with MeOH three times to provide S2 as a dark pink solid (117 mg, 96%, TFA salt). The material was used in the next step without further purification. $^1$H NMR (CD$_3$OD, 400 MHz) δ 8.90 (d, J=1.8 Hz, 1H), 8.42 (dd, J=7.9, 1.8 Hz, 1H), 7.51 (d, J=7.9 Hz, 1H), 7.05 (d, J=9.2 Hz, 2H), 6.60 (dd, J=9.2, 2.2 Hz, 2H), 6.53 (d, J=2.2 Hz, 2H), 4.30 (t, J=7.6 Hz, 8H), 2.56 (quint, J=7.6 Hz, 4H); $^{13}$C NMR (CD$_3$OD, 101 MHz) δ 167.9 (C), 167.2 (C), 160.3 (C), 158.8 (C), 158.1 (C), 139.6 (C), 134.5 (CH$_3$), 134.2 (C), 133.5 (CH$_3$), 132.8 (C), 132.1 (CH$_3$), 132.0 (CH$_3$), 114.6 (C), 113.6 (CH$_3$), 95.1 (CH$_3$), 52.9 (CH$_2$), 16.8 (CH$_2$); HRMS (ESI) calcd for C$_{27}$H$_{23}$N$_2$O$_5$ [M+H]$^+$ 455.1607, found 455.1606.

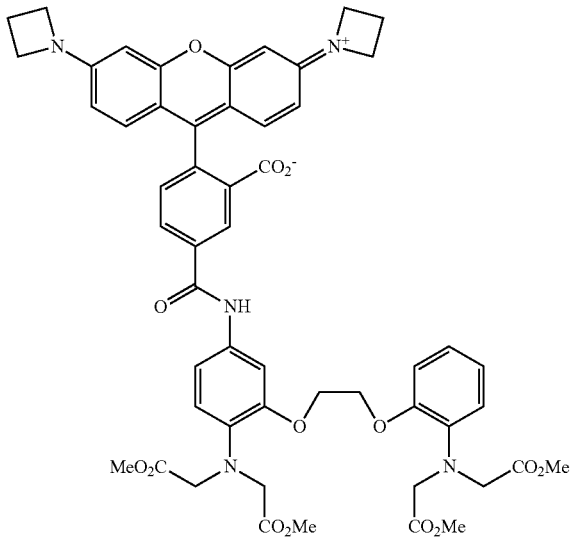

5-BAPTA-JF$_{549}$ tetramethyl ester (S3): To a solution of S2 (25 mg, 0.044 mmol), 5-amino-BAPTA-tetramethyl ester 11$^5$ (26.5 mg, 0.048 mmol, 1.1 eq) and BOP (21.2 mg, 0.048 mmol, 1.1 eq) in DMF (3 mL) was added DIEA (40 μL, 0.22 mmol, 5 eq). The mixture was stirred at room temperature for 3 h and concentrated to dryness. Purification by reverse phase HPLC (20-75% MeCN/H$_2$O, linear gradient, with constant 0.1% v/v TFA additive) afforded S3 as a dark pink solid (17 mg, 37%, TFA salt). $^1$H NMR (CDCl$_3$, 400 MHz) δ 9.64 (s, 1H), 8.59 (s, 1H), 8.23 (d, J=7.9 Hz, 1H), 7.39 (s, 1H), 7.34 (d, J=8.5 Hz, 1H), 7.28 (d, J=7.9 Hz, 1H), 7.00-6.82 (m, 7H), 6.39 (dd, J=9.2, 2.0 Hz, 2H), 6.23 (d, J=2.1 Hz, 2H), 4.23-4.19 (m, 12H), 4.12 (d, J=8.8 Hz, 8H), 3.59-3.57 (m, 12H), 2.52 (p, J=7.4 Hz, 4H); Analytical HPLC: t$_R$=12.5 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{53}$H$_{54}$N$_5$O$_{14}$ [M+H]$^+$ 984.3667, found 984.3668.

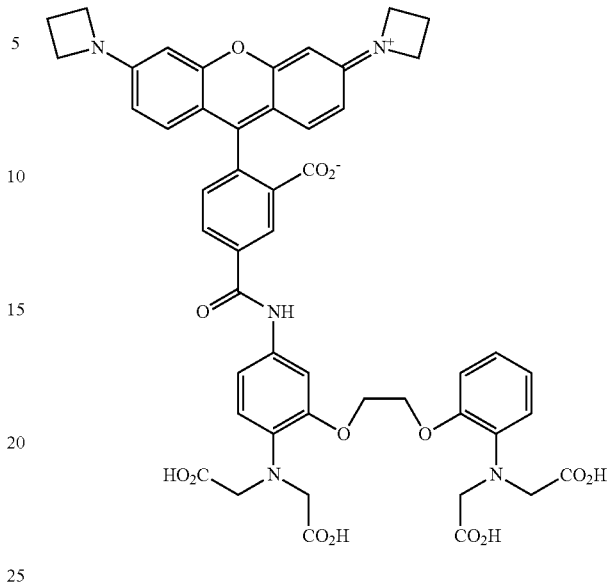

5-BAPTA-JF$_{549}$ (3): To a solution of S3 (15 mg, 0.014 mmol) in THF/MeOH (1/1: 3 mL) was added KOH (1 M in H$_2$O, 245 μL, 0.245 mmol, 18 eq). The mixture was stirred at room temperature for 18 h. It was subsequently neutralized with HCl 1 M, concentrated and diluted with MeOH. Purification by reverse phase HPLC (25-55% MeCN/H$_2$O, linear gradient, with constant 0.1% v/v TFA additive) afforded 3 as a dark pink solid (3.9 mg, 27%, TFA salt). $^1$H NMR (CD$_3$OD 400 MHz) δ 8.83 (d, J=1.7 Hz, 1H), 8.36-8.33 (m, 11H), 7.55 (d, J=7.9 Hz, 1H), 7.48 (d, J=2.2 Hz, 11H), 7.29 (dd, J=8.6, 2.2 Hz, 11H), 7.06-7.04 (m, 3H), 7.00-6.88 (m, 4H), 6.60 (dd, J=9.2, 2.2 Hz, 2H), 6.52 (d, J=2.1 Hz, 2H), 4.38-4.34 (m, 4H), 4.30 (t, J=7.6 Hz, 8H), 4.11 (s, 4H), 4.07 (s, 4H), 2.55 (p, J=7.5 Hz, 4H); Analytical HPLC: t$_R$=14.3 min, 99% purity (20-50% MeCN/H$_2$O, linear gradient, with constant 0.1% v/v TFA additive, 20 min run, 1 mL/min flow, detection at 254 nm); HRMS (ESI) calcd for C$_{49}$H$_{46}$N$_5$O$_4$ [M+H]$^+$ 928.3041, found 928.3047.

Example 6: Synthesis of Exemplary Compounds Including Compound 4

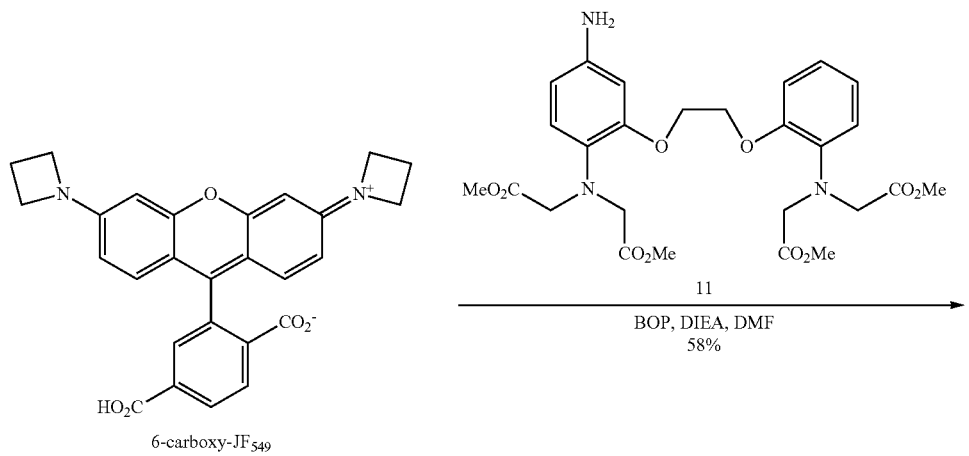

-continued

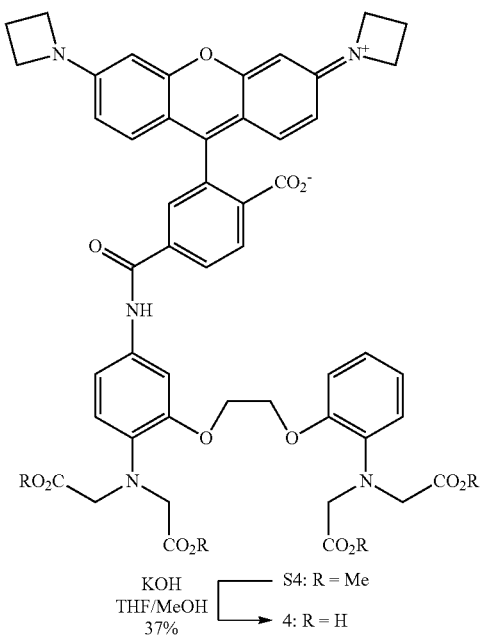

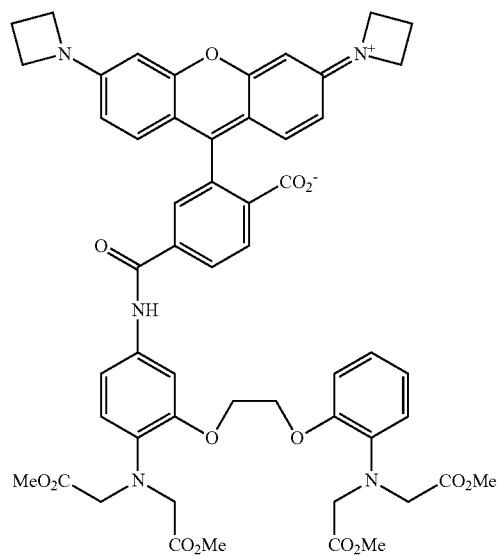

6-BAPTA-JF$_{549}$ tetramethyl ester (S4): To a solution of 6-carboxy-JF$_{549}$[6] (25 mg, 0.044 mmol), 5-amino-BAPTA-tetramethyl ester 11[5] (26.5 mg, 0.048 mmol, 1.1 eq) and BOP (21.2 mg, 0.048 mmol, 1.1 eq) in DMF (3 mL) was added DIEA (40 μL, 0.22 mmol, 5 eq). The mixture was stirred at room temperature for 3 h and evaporated to dryness. Purification by silica gel chromatography (0-10% MeOH (2 M NH3)/CH$_2$Cl2, linear gradient) provided S5 as a dark pink solid (25 mg, 58%). 1H NMR (CDCl3, 400 MHz) δ 8.89 (br s, 1H), 8047-8.03 (m, 2H), 7.57 (s, 1H), 7.28 (s, 1H), 7.18 (s, 1H), 6.91-6.79 (m, 4H), 6.74 (d, J=8.7 Hz, 11H), 6.65 (d, J=8.8 Hz, 2H), 6.16-6.13 (m, 2H), 6.10-6.06 (m, 2H), 4.19-4.16 (m, 4H), 4.10-4.08 (m, 8H), 3.99 (t, J=7.9 Hz, 8H), 3.55-3.54 (m, 12H), 2.44-2.36 (m, 4H); Analytical HPLC: tR=12.7 min, 98% purity (20-80% MeCN/H$_2$O, linear gradient, with constant 0.1% v/v TFA additive, 20 min run, 1 mL/min flow, detection at 254 nm); HRMS (ESI) calcd for C53H54N5O14 [M+H]+ 984.3667, found 984.3675.

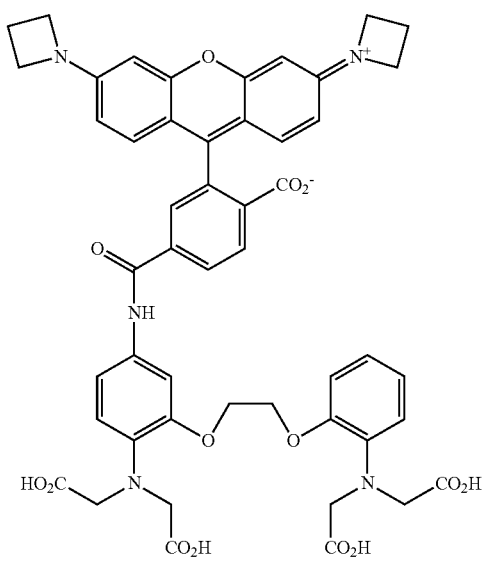

6-BAPTA-JF$_{549}$ (4): To a solution of S4 (25 mg, 0.025 mmol) in THF/MeOH (1/1: 5 mL) was added KOH (1 M in H2O, 460 μL, 0.46 mmol, 18 eq). The mixture was stirred at room temperature for 18 h. It was subsequently neutralized with HCl 1 M, concentrated and diluted with MeOH. Purification by reverse phase HPLC (20-50% MeCN/H$_2$O, linear gradient, with constant 0.1% v/v TFA additive) afforded 4 as a dark pink solid (9.9 mg, 37%, TFA salt). 1H NMR (CD30D, 400 MHz) δ 8.35 (d, J=8.0 Hz, 1H), 8.22 (d, J=8.2 Hz, 1H), 7.86 (s, 1H), 7.40 (s, 1H), 7.18 (d, J=8.4 Hz, 1H), 7.00-6.85 (m, 7H), 6.51-6.49 (m, 4H), 4.30-4.19 (m, 12H), 4.04 (s, 4H), 3.97 (s, 4H), 2.54 (q, J=7.5 Hz, 4H); Analytical HPLC: tR=10.1 min, 99% purity (10-95% MeCN/H$_2$O, linear gradient, with constant 0.1% v/v TFA additive, 20 min run, 1 mL/min flow, detection at 254 nm); HRMS (ES−) calcd for C49H44N5O14 [M−H]+926.2885, found 926.2893.

Example 7: Synthesis of Exemplary Compounds Including Compound 5

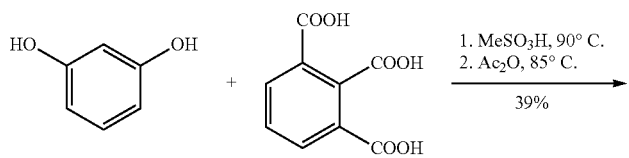

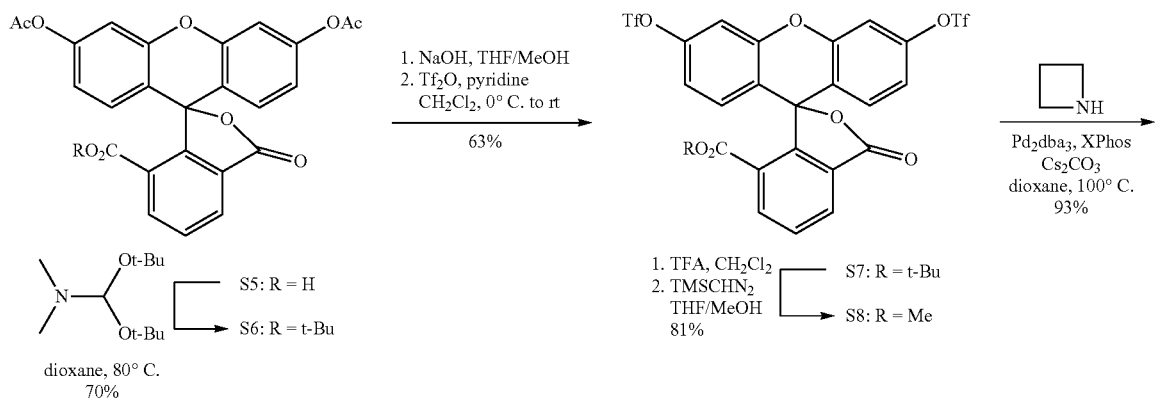

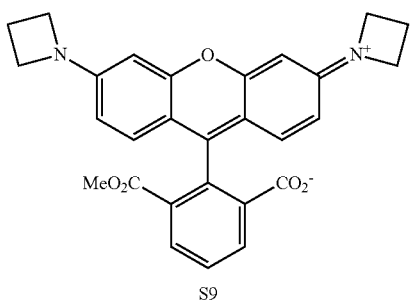

-continued
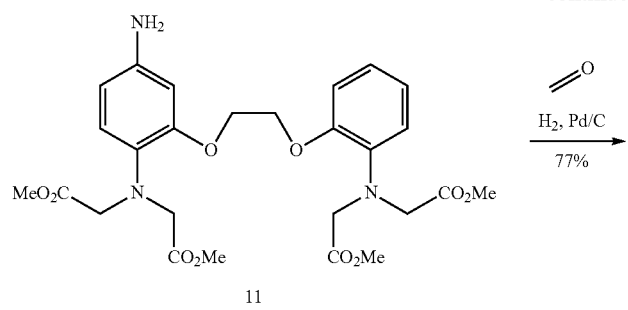
11
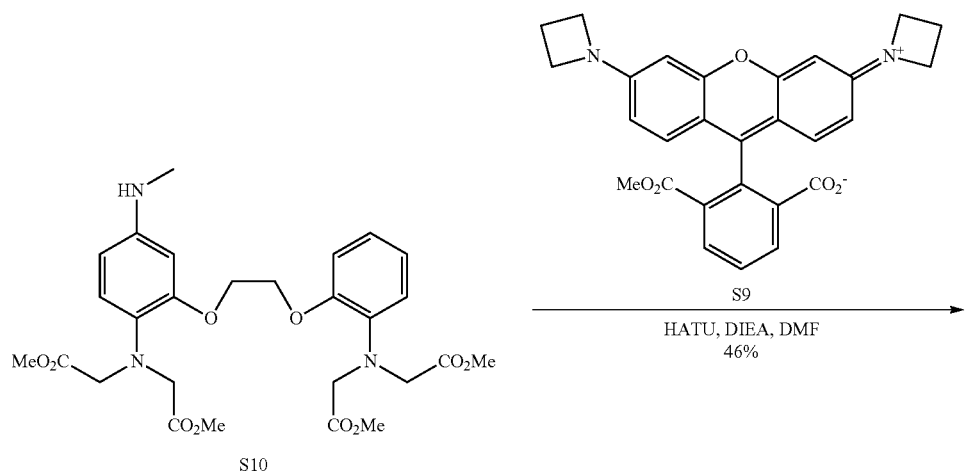
S10
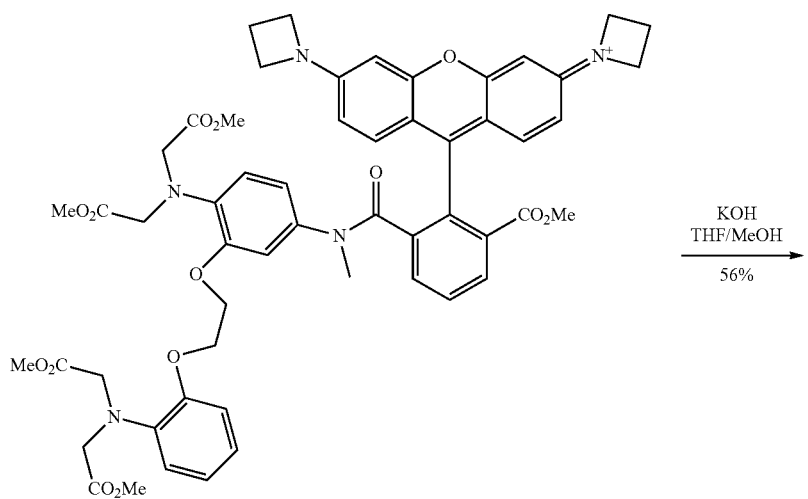
S11

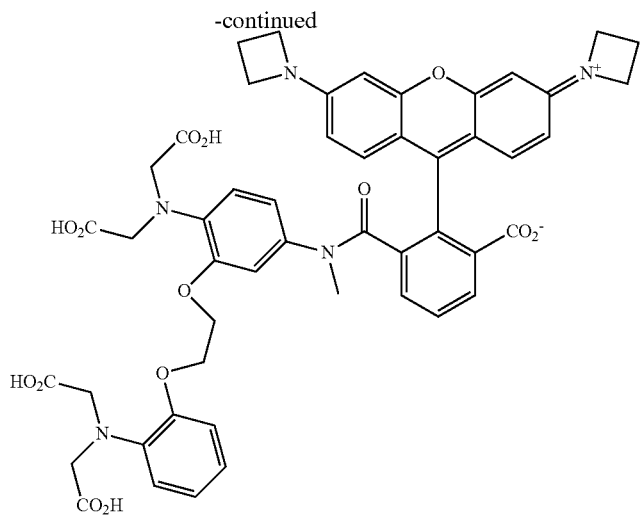

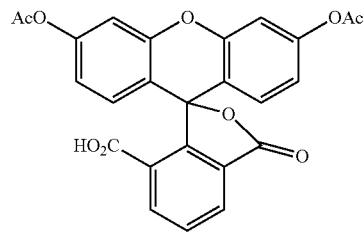 [SMILES: CC(=O)Oc1ccc2c(c1)Oc1cc(OC(C)=O)ccc1C21OC(=O)c2cccc(C(=O)O)c21]

7-carboxyfluorescein diacetate (S5): A vial was charged with benzene-1,2,3-tricarboxylic acid (1.91 g, 9.09 mmol), resorcinol (2.00 g, 18.2 mmol, 2 eq) and $CH_3SO_3H$ (18 mL). The vial was sealed and heated at 90° C. under microwave for 30 min. The mixture was cooled to room temperature and poured into 200 mL of ice-water under stirring. The orange precipitate was filtered and dried under vacuum. The intermediate 7-carboxyfluorescein was suspended in $Ac_2O$ (20 mL) and heated at 85° C. under microwave for 15 min. It was then cooled to room temperature and evaporated to dryness. The residue was partitioned in EtOAc and $H_2O$, the aqueous layer was extracted with EtOAc (3×). The combined organic layers were dried over $MgSO_4$, filtered and evaporated. The resulting solid was washed with iPrOH (2×) to afford S5 as a white solid (1.65 g, 39%). $^1H$ NMR ($CDCl_3$, 400 MHz) δ 8.39 (dd, J=7.8, 1.2 Hz, 1H), 8.27 (dd, J=7.6, 1.2 Hz, 1H), 7.78 (t, J=7.7 Hz, 1H), 7.03 (d, J=2.2 Hz, 2H), 6.73 (dd, J=8.7, 2.2 Hz, 2H), 6.68 (d, J=8.6 Hz, 2H), 2.27 (s, 6H); $^{13}C$ NMR ($CDCl_3$, 101 MHz) δ 169.0 (C), 168.0 (C), 166.1 (C), 152.5 (C), 151.9 (C), 151.6 (C), 138.4 (CH), 131.1 (CH), 130.3 (CH), 128.5 (C), 127.8 (CH), 125.6 (C), 117.1 (CH), 116.3 (C), 110.0 (CH), 83.8 (C), 21.3 ($CH_3$); HRMS (ESI) calcd for $C_{25}H_{17}O_9[M+H]^+$ 461.0873, found 461.0869.

7-tert-butoxycarbonylfluorescein diacetate (S6): A suspension of S5 (250 mg, 0.543 mmol) in dioxane (6 mL) was heated to 80° C., and N,N-di-tert-butyl acetal (782 μL, 3.26 mmol, 6 eq) was added dropwise over 5 min. The reaction was stirred at 80° C. for 1 h. After cooling to room temperature, it was diluted with saturated $NaHCO_3$ and extracted with $CH_2Cl_2$ (2×). The combined organic layers were dried over $MgSO_4$, filtered and evaporated. Purification by silica gel chromatography (0-20% EtOAc/hexanes, linear gradient, with constant 40% v/v $CH_2Cl_2$) provided S6 as a white solid (195 mg, 70%). $^1H$ NMR ($CDCl_3$, 400 MHz) δ 8.28 (dd, J=7.7, 1.2 Hz, 1H), 8.22 (dd, J=7.6, 1.2 Hz, 1H), 7.78 (t, J=7.7 Hz, 1H), 7.09 (d, J=2.3 Hz, 2H), 6.76 (dd, J=8.6, 2.3 Hz, 2H), 6.70 (d, J=8.6 Hz, 2H), 2.30 (s, 6H), 1.05 (s, 9H); $^{13}C$ NMR ($CDCl_3$, 101 MHz) δ 168.8 (C), 167.8 (C), 162.9 (C), 152.1 (C), 152.0 (C), 149.3 (C), 137.3 (CH), 131.0 (CH), 129.3 (C), 129.1 (C), 129.0 (CH), 127.5 (CH), 117.4 (C), 117.3 (CH), 110.4 (CH), 84.2 (C), 83.0 (C), 27.5 ($CH_3$), 21.6 ($CH_3$); HRMS (ESI) calcd for $C_{29}H_{25}O_9$ $[M+H]^+$ 517.1499, found 517.1498.

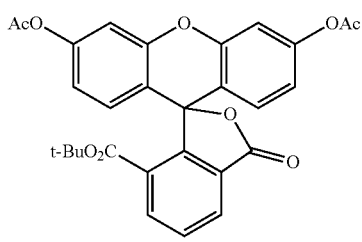

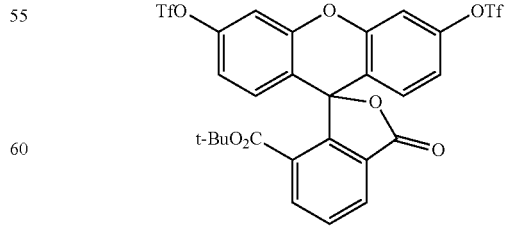

7-tert-butoxycarbonylfluorescein ditriflate (S7): To a solution of S6 (800 mg, 1.55 mmol) in 1:1 THF/MeOH (16 mL) was added 1 M NaOH (3.71 mL, 3.71 mmol, 2.4 eq).

The reaction was stirred at room temperature for 2.5 h. The resulting red-orange solution was acidified with 1 N HCl (4 mL), diluted with water, and extracted with EtOAc (3×). The organics were washed with brine, dried over MgSO₄, filtered, and concentrated. The oily residue was diluted in CH₂Cl₂ (10 mL) and cooled to 0° C. Pyridine (1.00 mL, 12.4 mmol, 8 eq) and trifluoromethanesulfonic anhydride (1.04 mL, 6.20 mmol, 4 eq) were added, and the ice bath was removed. The reaction was stirred at room temperature for 1.5 h. It was subsequently diluted with water and extracted with CH₂Cl₂ (3×). The combined organic layers were dried over MgSO₄, filtered, and evaporated. Purification by silica gel chromatography (0-25% EtOAc/hexanes, linear gradient) provided S7 as a white solid (678 mg, 63%). $^1$H NMR (CDCl₃, 400 MHz) δ 8.28-8.25 (m, 2H), 7.82 (t, J=7.7 Hz, 1H), 7.26 (d, J=3.7 Hz, 2H), 6.95 (dd, J=8.8, 2.5 Hz, 2H), 6.80 (d, J=8.8 Hz, 2H), 1.13 (s, 9H); $^{19}$F NMR (CDCl₃, 376 MHz) δ -73.24 (s); $^{13}$C NMR (CDCl₃, 101 MHz) δ 167.6 (C), 162.2 (C), 151.8 (C), 150.2 (C), 150.1 (C), 137.5 (CH), 131.6 (CH), 129.3 (CH), 128.6 (CH), 128.3 (C), 128.1 (C), 119.8 (C), 118.8 (q, $^1J_{CF}$=322.2 Hz, CF₃), 116.9 (CH), 110.4 (CH), 83.2 (C), 82.4 (C), 27.5 (CH₃); HRMS (ESI) calcd for C₂₇H₁₉O₁₁S₂F₆ [M+H]⁺ 697.0273, found 697.0265.

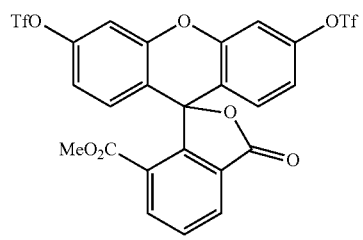 [SMILES: COC(=O)c1cccc2c1C1(OC2=O)c2ccc(OS(=O)(=O)C(F)(F)F)cc2Oc2cc(OS(=O)(=O)C(F)(F)F)ccc21]

7-methoxycarbonylfluorescein ditriflate (S8): S9 (210 mg, 0.301 mmol) was taken up in CH₂Cl₂ (8 mL) and trifluoroacetic acid (1.0 mL) was added. The reaction was stirred at room temperature for 2 h. Toluene (3 mL) was added, the reaction mixture was concentrated to dryness and then azeotroped with MeOH three times. The white solid was dissolved in THF/MeOH (4/1: 10 mL) under argon and trimethylsilyldiazomethane (2.0 M in Et₂O, 226 µL, 0.452 mmol, 1.5 eq) was added. The reaction was stirred 1 h at room temperature after which excess trimethylsilyldiazomethane (2.0 M in Et₂O, 780 µL, 1.50 mmol, 5 eq) were added to complete the reaction. The reaction was stirred 1 h at room temperature and concentrated to dryness. Purification by silica gel chromatography (0-25% EtOAc/hexanes, linear gradient) provided S8 as a white solid (160 mg, 81%). $^1$H NMR (CDCl₃, 400 MHz) δ 8.42 (dd, J=7.8, 1.2 Hz, 11H), 8.33 (dd, J=7.6, 1.2 Hz, 1H), 7.86 (t, J=7.7 Hz, 11H), 7.28 (d, J=2.5 Hz, 2H), 6.96 (dd, J=8.8, 2.5 Hz, 2H), 6.80 (d, J=8.8 Hz, 2H), 3.50 (s, 3H); $^{19}$F NMR (CDCl₃, 376 MHz) δ -73.17 (s); $^{13}$C NMR (CDCl₃, 101 MHz) δ 167.5 (C), 163.2 (C), 151.4 (C), 151.3 (C), 150.1 (C), 138.1 (CH), 131.7 (CH), 130.1 (CH), 128.8 (CH), 128.1 (C), 126.0 (C), 119.3 (C), 118.2 (d, $^1J_{CF}$=322.2 Hz, CF₃), 117.1 (CH), 110.3 (CH), 82.1 (C), 52.40 (CH₃); HRMS (ESI) calcd for C₂₄H₁₃O₁₁S₂F₆ [M+H]⁺ 654.9803, found 654.9797.

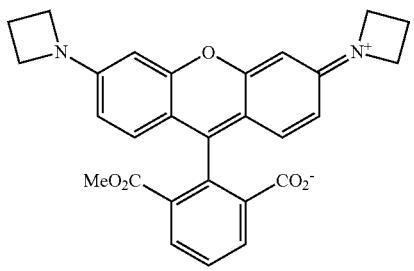

7-methoxycarbonyl-JF₅₄₉ (S9): A vial was charged with S8 (140 mg, 0.214 mmol), Pd₂dba₃ (20 mg, 0.021 mmol, 0.1 eq), XPhos (31 mg, 0.064 mmol, 0.3 eq), and Cs₂CO₃ (195 mg, 0.600 mmol, 2.8 eq). The vial was sealed under argon. Dioxane (3 mL) and then azetidine (35 µL, 0.51 mmol, 2.4 eq) were added. The reaction was stirred at 100° C. for 5 h. It was subsequently cooled to room temperature, diluted with MeOH, deposited onto Celite and concentrated to dryness. Purification by silica gel chromatography (0-10%/hexanes, linear gradient) followed by a second purification by silica gel chromatography (0-10% MeOH (2 M NH₃)/CH₂Cl₂, linear gradient) provided S9 (94 mg, 93%) as a pink solid. $^1$H NMR (CD₂Cl2, 400 MHz) δ 8.29 (dd, J=7.7, 1.2 Hz, 1H), 8.18 (dd, J=7.7, 1.2 Hz, 1H), 7.72 (t, J=7.7 Hz, 1H), 6.49 (d, J=8.5 Hz, 2H), 6.19 (d, J=2.3 Hz, 2H), 6.04 (dd, J=8.5, 2.3 Hz, 2H), 3.89 (t, J=7.3 Hz, 8H), 3.43 (s, 3H), 2.35 (p, J=7.3 Hz, 4H); $^{13}$C NMR (CD₂Cl₂, 101 MHz) δ 168.8 (C), 164.4 (C), 153.9 (C), 152.5 (C), 152.4 (C), 137.6 (CH), 130.5 (CH), 129.5 (C), 129.5 (CH), 127.8 (CH), 126.9 (C), 108.2 (C), 107.4 (CH), 97.6 (CH), 52.5 (CH₂), 52.3 (CH₃), 17.1 (CH₂); HRMS (ESI) calcd for C₂₈H₂₅N₂O₅ [M+H]⁺ 469.1763, found 469.1762.

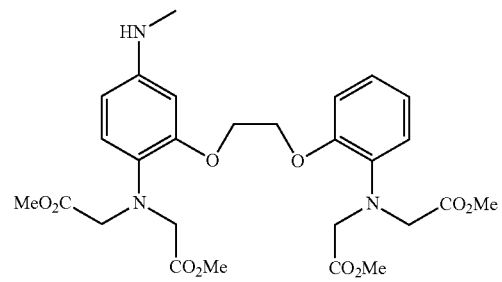 [SMILES: CNc1ccc(N(CC(=O)OC)CC(=O)OC)c(OCCOc2ccccc2N(CC(=O)OC)CC(=O)OC)c1]

N-methyl-5-amino-BAPTA tetramethyl ester (S10): 5-amino-BAPTA tetramethyl ester 11⁵ (100 mg, 0.182 mmol) was suspended in EtOAc (10 mL). The flask was flushed under argon, formaldehyde (37% in H₂O, 17.5 µL, 0.238 mmol, 1.3 eq) and then Pd/C (39 mg, 0.2 eq) were added. The reaction was stirred at room temperature under a hydrogen atmosphere for 24 h, after which formaldehyde (37% in 1120, 2.7 µL, 0.037 mmol, 0.2 eq) was added to complete the reaction. After stirring at room temperature for 15 h, the mixture was filtered through Celite and washed with EtOAc. The filtrate was evaporated to dryness and purification by silica gel chromatography (20-80% EtOAc/hexanes, linear gradient) provided S10 as a beige solid (79 mg, 77%). $^1$H NMR (CDCl₃, 400 MHz) δ 6.95-6.80 (m, 5H), 6.20 (d, J=2.7 Hz, 1H), 6.15 (dd, J=8.4, 2.4 Hz, 1H), 4.28 (s, 4H), 4.16 (d, J=1.3 Hz, 4H), 4.06 (s, 4H), 3.59 (d, J=1.2 Hz, 6H), 3.57 (d, J=1.1 Hz, 611), 2.78 (s, 3H); $^{13}$C NMR (CDCl3, 101 MHz,) δ 172.3 (C), 172.1 (C), 152.6 (C), 150.6 (C), 146.3 (C), 139.4 (C), 130.5 (C), 122.5 (CH), 122.2 (CH), 121.6 (CH), 119.2 (CH), 113.5 (CH), 104.7 (CH), 99.6 (CH), 67.4 (CH$_2$), 67.2 (CH$_2$), 54.1 (CH$_2$), 53.5 (CH$_2$), 51.7 (CH$_3$), 51.6 (CH$_3$), 31.3 (CH$_3$); HRMS (ESI) calcd for C$_{27}$H$_{36}$N$_3$O$_{10}$ [M+H]$^+$ 562.2401, found 562.2402.

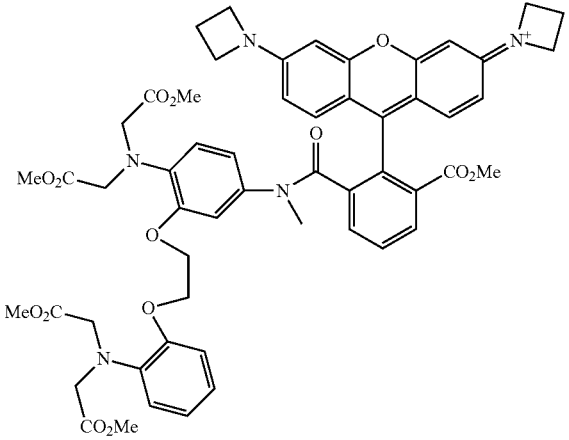 [SMILES: COC(=O)CN(CC(=O)OC)c1ccccc1OCCOc1cc(N(C)C(=O)c2cccc(C(=O)OC)c2-c2c3ccc(=[N+]4CCC4)cc-3oc3cc(N4CCC4)ccc23)ccc1N(CC(=O)OC)CC(=O)OC]

7-MeBAPTA-JF$_{549}$ pentamethyl ester (S11): To a solution of S9 (20 mg, 0.042 mmol), S10 (26 mg, 0.046 mmol, 1.1 eq) and HATU (19.2 mg, 0.050 mmol, 1.2 eq) in DMF (3 mL) was added DIEA (8.8 µL, 0.063 mmol, 1.5 eq). The mixture was stirred at room temperature for 7 h. It was subsequently diluted with water and extracted with CH$_2$Cl$_2$ (3×). The combined organic layers were dried over MgSO$_4$, filtered, and evaporated. Purification by silica gel chromatography (0-10% MeOH (2 M NH$_3$)/CH$_2$Cl$_2$, linear gradient) provided S11 as a dark pink solid (19.8 mg, 46%). $^1$H NMR ((CD$_3$)$_2$SO, 400 MHz) δ 8.16 (d, J=7.7 Hz, 1H), 8.04 (dd, J=7.8, 1.3 Hz, 1H), 7.85-7.80 (m, 1H), 7.03-6.75 (m, 6H), 6.57-6.51 (m, 5H), 6.29-6.22 (m, 2H), 4.36-4.27 (m, 8H), 4.22 (t, J=4.7 Hz, 2H), 4.13 (s, 4H), 4.06 (s, 4H), 3.97 (t, J=4.6 Hz, 2H), 3.54-3.52 (m, 12H), 3.49 (s, 3H), 2.72 (s, 3H), 2.50-2.44 (m, 4H); Analytical HPLC: t$_R$=12.6 min, 96% purity (10-95% MeCN/H$_2$O, linear gradient, with constant 0.1% v/v TFA additive, 20 min run, 1 mL/min flow, detection at 254 nm); HRMS (ESI) calcd for C$_{55}$H$_{58}$N$_5$O$_{14}$ [M]$^+$ 1012.3980, found 1012.3977.

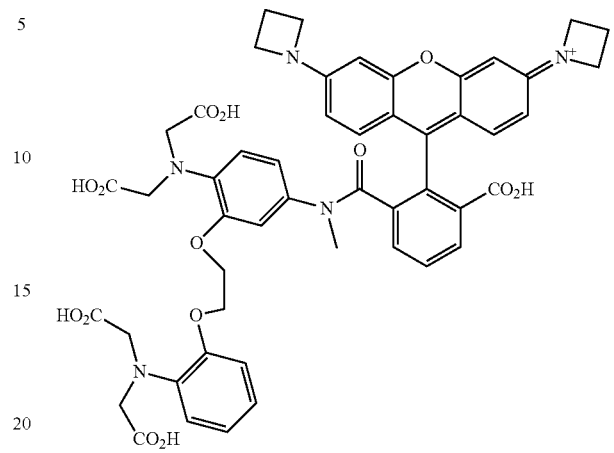

7-MeBAPTA-JF$_{549}$ (5): To a solution of S11 (14 mg, 0.014 mmol) in THF/MeOH (1/1: 2 mL) was added KOH (1 M in H$_2$O, 276 µL, 0.276 mmol, 20 eq). The mixture was stirred at room temperature for 20 h. It was subsequently neutralized with HCl 1 M, concentrated and diluted with MeOH. Purification by reverse phase HPLC (20-50% MeCN/H$_2$O, linear gradient, with constant 0.1% v/v TFA additive) afforded 5 as a dark pink solid (8.3 mg, 56%, TFA salt). $^1$H NMR ((CD$_3$)$_2$SO, 400 MHz) 8.05 (d, J=7.7 Hz, 1H), 7.85 (d, J=7.6 Hz, 1H), 7.74-7.69 (m, 1H), 7.02-6.98 (m, 1H), 6.89 (dd, J=4.8, 3.1 Hz, 3H), 6.70 (br s, 2H), 6.53 (br s, 1H), 6.42-6.38 (m, 5H), 6.15 (br s, 1H), 4.27 (t, J=5.4 Hz, 2H), 4.18-4.06 (m, 14H), 4.00 (s, 4H), 2.85 (s, 3H), 2.40 (p, J=7.4 Hz, 4H); Analytical HPLC: t$_R$=9.3 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{50}$H$_{48}$N$_5$O$_{14}$ [M+H]$^+$ 942.3198, found 942.3199.

Example 8: Synthesis of Exemplary Compounds Including Compounds 6, 7, and 7$_{Am}$

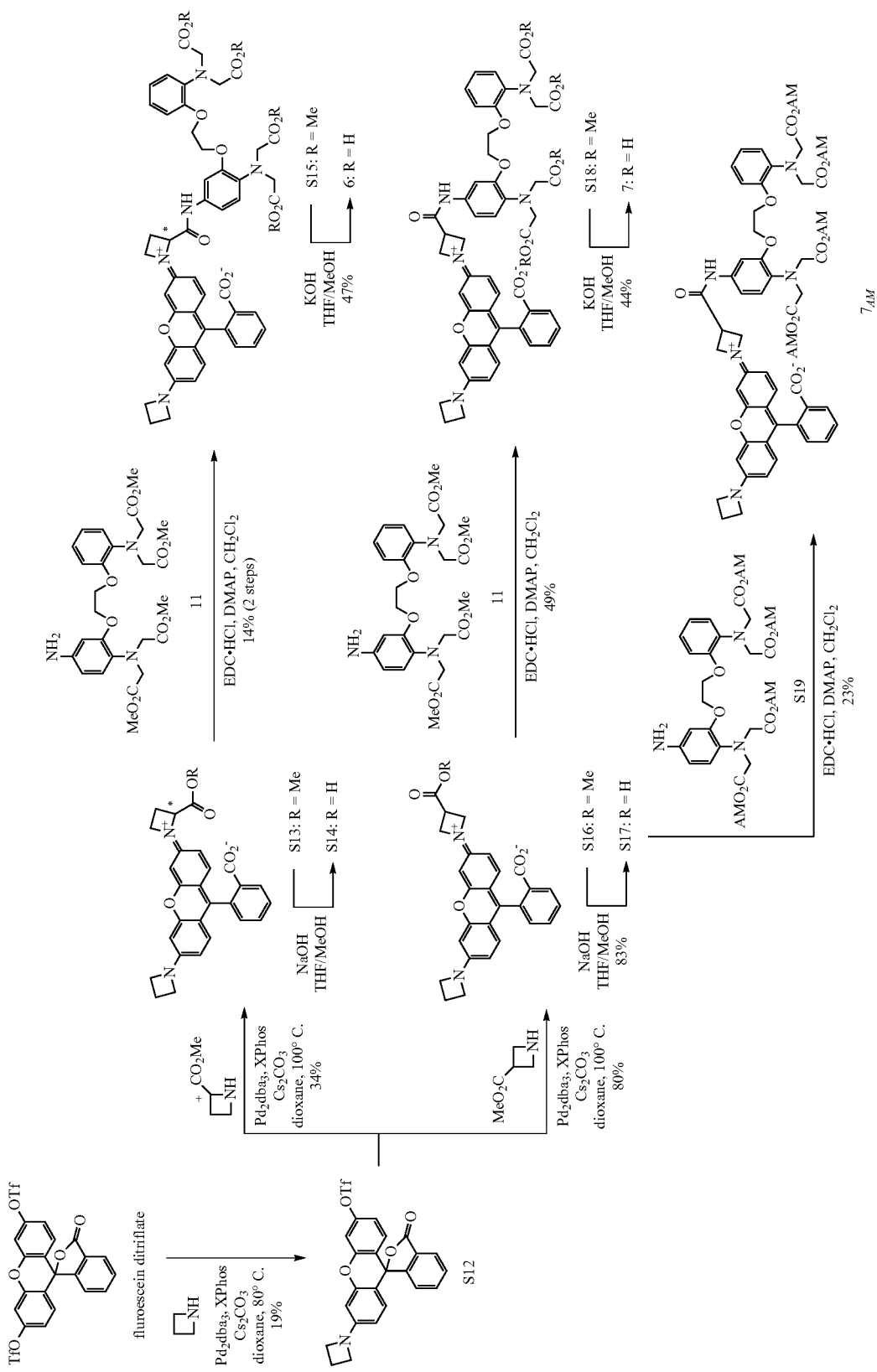

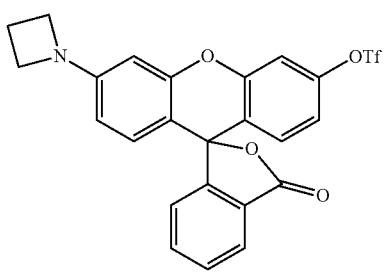 [SMILES: O=C1OC2(c3ccc(OS(=O)(=O)C(F)(F)F)cc3Oc3cc(N4CCC4)ccc32)c2ccccc21]

JF$_{549}$ triflate (S12): A vial was charged with fluorescein ditriflate[4] (1.50 g, 2.52 mmol), Pd$_2$dba$_3$ (115 mg, 0.126 mmol, 0.05 eq), XPhos (180 mg, 0.378 mmol, 0.15 eq), and Cs$_2$CO$_3$ (1.14 mg, 3.50 mmol, 1.4 eq). The vial was sealed under argon. Dioxane (13 mL) and then azetidine (170 µL, 2.52 mmol, 1 eq) were added. The reaction was stirred at 80° C. for 2 h. It was subsequently cooled to room temperature, diluted with MeOH, deposited onto Celite and concentrated to dryness. Purification by silica gel chromatography (0-35% EtOAc/hexanes, linear gradient) provided S12 as an off-white solid (238 mg, 19%). $^1$H NMR (CDCl$_3$, 400 MHz) δ 8.03 (dt, J=7.5, 1.0 Hz, 1H), 7.72-7.61 (m, 2H), 7.21 (d, J=2.4 Hz, 1H), 7.18 (dt, J=7.6, 1.0 Hz, 1H), 6.92 (dd, J=8.8, 2.5 Hz, 1H), 6.86 (d, J=8.8 Hz, 1H), 6.59 (d, J=8.6 Hz, 1H), 6.23 (d, J=2.3 Hz, 1H), 6.14 (dd, J=8.6, 2.3 Hz, 1H), 3.93 (t, J=7.3 Hz, 4H), 2.40 (p, J=7.3 Hz, 2H); $^{19}$F NMR (CDCl$_3$, 376 MHz) δ -73.21; $^{13}$C NMR (CDCl$_3$, 101 MHz) δ 169.3 (C), 153.9 (C), 152.8 (C), 152.5 (C), 152.1 (C), 150.0 (C), 135.3 (CH), 130.2 (CH), 130.1 (CH), 128.8 (CH), 126.9 (C), 125.3 (CH), 124.1 (CH), 120.3 (C), 118.8 (q, $^1J_{CF}$=322.2 Hz, CF$_3$), 116.4 (CH), 110.5 (CH), 108.6 (CH), 106.3 (C), 97.6 (CH), 82.7 (C), 52.1 (CH$_2$), 16.8 (CH$_2$); HRMS (ESI) calcd for C$_{24}$H$_{17}$NO$_6$SF$_3$ [M+H]$^+$ 504.0729, found 504.0735.

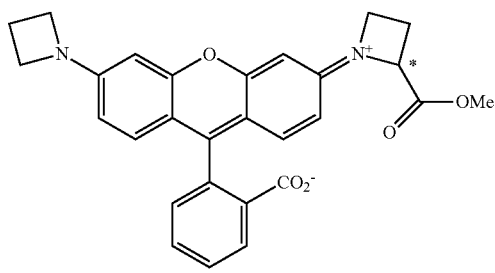

2"-methoxycarbonyl-JF$_{549}$ (S13): A vial was charged with S12 (250 mg, 0.50 mmol), Pd$_2$dba$_3$ (45.8 mg, 0.050 mmol, 0.1 eq), XPhos (72 mg, 0.15 mmol, 0.3 eq), Cs$_2$CO$_3$ (490 mg, 1.50 mmol, 3.0 eq), and methyl 2-azetidinecarboxylate hydrochloride (152 mg, 1.0 mmol, 2.0 eq). The vial was sealed under argon. Dioxane (10 mL) was added. The reaction was stirred at 100° C. for 6 h. It was subsequently cooled to room temperature, diluted with MeOH, deposited onto Celite and concentrated to dryness. Purification by silica gel chromatography (0-10% MeOH (2 M NH$_3$)/CH$_2$Cl$_2$, linear gradient) provided S13 as a pink solid (80 mg, 34%). The compound was obtained as a mixture of diastereomers. $^1$H NMR (CD$_3$OD, 400 MHz) δ 8.10-8.01 (m, 1H), 7.69-7.59 (m, 2H), 7.24-7.15 (m, 1H), 7.08-7.00 (m, 2H), 6.56-6.44 (m, 3H), 6.41-6.37 (m, 1H), 4.97-4.89 (m, 1H), 4.20-4.13 (m, 5H), 4.06-3.98 (m, 1H), 3.81-3.77 (m, 3H), 2.85-2.73 (m, 1H), 2.61-2.43 (m, 3H); $^{13}$C NMR (CDCl$_3$, 101 MHz) δ 172.55 (C), 172.54 (C), 169.82 (C), 169.79 (C), 153.6 (C), 153.4 (C), 152.70 (C), 152.68 (C), 152.66 (C), 152.65 (C), 152.20 (C), 152.18 (C), 134.75 (CH), 134.73 (CH), 129.4 (CH), 129.0 (CH), 128.8 (CH), 127.40 (CH), 127.38 (CH), 124.8 (CH), 124.12 (CH), 124.10 (CH), 109.4 (C), 108.4 (CH), 108.2 (CH), 107.7 (CH), 107.5 (C), 98.9 (CH), 98.8 (CH), 97.6 (CH), 85.0 (C), 63.30 (CH$_3$), 63.28 (CH$_3$), 52.44 (CH), 52.42 (CH), 52.1 (CH$_2$), 50.00 (CH$_2$), 49.98 (CH$_2$), 21.5 (CH$_2$), 16.8 (CH$_2$); HRMS (ESI) calcd for C$_{28}$H$_{25}$N$_2$O$_5$ [M+H]$^+$ 469.1763, found 469.1762.

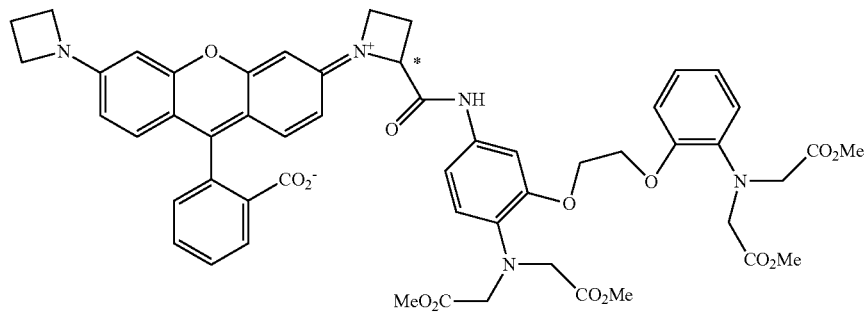

2"-BAPTA-JF$_{549}$ tetramethyl ester (S15): S13 (32 mg, 68 µmol) was taken up in THF/MeOH (1/1: 5 mL) and NaOH (1 M in H$_2$O, 274 µL, 0.27 mmol, 4.0 eq) was added. The reaction was stirred at room temperature for 2 h. It was subsequently neutralized with HCl 1 M (300 µL). The residue was diluted with H$_2$O and the organics were evaporated. The aqueous layer was extracted with CH$_2$Cl$_2$ (3×). The combined organic layers were dried over MgSO$_4$, filtered, and evaporated. The dark pink solid was charged in a vial with 11[5] (43 mg, 0.079 mmol, 1.2 eq), EDC·HCl (19 mg, 0.100 mmol, 1.5 eq) and DMAP (1.6 mg, 0.0132 mmol, 0.2 eq) DMF (3 mL) was added. The mixture was stirred at room temperature for 5 h and concentrated to dryness. Purification by reverse phase HPLC (30-60% MeCN/H$_2$O, linear gradient, with constant 0.1% v/v TFA additive) afforded S15 as a dark pink solid (10 mg, 14%, TFA salt). The compound was obtained as a mixture of diastereomers. $^1$H NMR (CDCl$_3$, 400 MHz) δ 8.55-8.50 (m, 1H), 8.01-7.97 (m, 1H), 7.67-7.56 (m, 2H), 7.35-7.33 (m, 1H), 7.18-7.15 (m, 11H), 7.01-6.95 (m, 1H), 6.94-6.78 (m, 4H), 6.66-6.62 (m, 1H), 6.57-6.54 (m, 1H), 6.41-6.39 (m, 11H), 6.26-6.22 (m, 11H), 6.20-6.19 (m, 11H), 6.11-6.08 (m, 1H), 4.48-4.41 (m, 1H), 4.32-4.26 (m, 4H), 4.15-4.04 (m, 9H), 3.93-3.88 (m, 5H), 3.59-3.54 (m, 12H), 2.77-2.68 (m, 1H), 2.59-2.50 (m, 1H), 2.41-2.32 (m, 2H); Analytical HPLC:

$t_R$=13.7 min, 98% purity (20-70% MeCN/H$_2$O, linear gradient, with constant 0.1% v/v TFA additive, 20 min run, 1 mL/min flow, detection at 254 nm); HRMS (ESI) calcd for C$_{53}$H$_{54}$N$_5$O$_{14}$ [M+H]$^+$ 984.3667, found 984.3674.

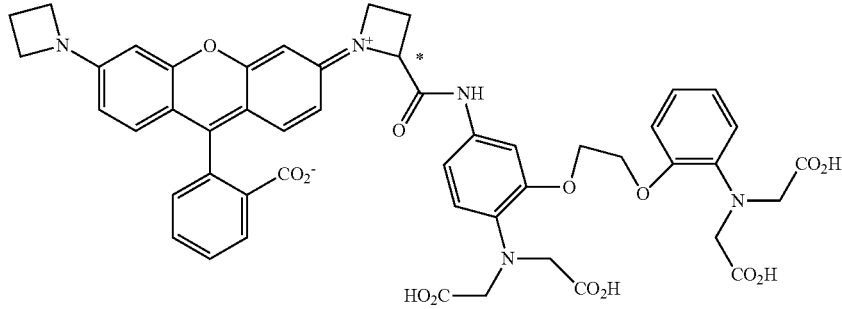

2"-BAPTA-JF$_{549}$ (6): To a solution of S15 (6 mg, 0.0061 mmol) in THF/MeOH (1/1: 2 mL) was added KOH (1 M in H$_2$O, 110 μL, 0.11 mmol, 18 eq). The mixture was stirred at room temperature for 7 h. It was subsequently neutralized with HCl 1 M, concentrated and diluted with MeOH. Purification by reverse phase HPLC (30-60% MeCN/H$_2$O, linear gradient, with constant 0.1% v/v TFA additive) afforded 6 as a dark pink solid (3.0 mg, 47%, TFA salt). The compound was obtained as a mixture of diastereomers. $^1$H NMR (CD$_3$OD, 400 MHz) δ 8.33-8.30 (m, 1H), 7.85-7.75 (m, 2H), 7.46-7.43 (m, 1H), 7.40-7.36 (m, 1H), 7.15-7.05 (m, 3H), 7.03-6.93 (m, 4H), 6.91-6.85 (m, 1H), 6.68-6.60 (m, 3H), 6.57-6.54 (m, 1H), 5.11 (s, 1H), 4.41-4.17 (m, 9H), 4.06-3.94 (m, 6H), 2.99-2.81 (m, 1H), 2.61-2.44 (m, 2H); Analytical HPLC: $t_R$=10.1 min, 99% purity (20-70% MeCN/H$_2$O, linear gradient, with constant 0.1% v/v TFA additive, 20 mm run, 1 mL/min flow, detection at 254 nm); HRMS (ESI) calcd for C$_{49}$H$_{46}$N$_5$O$_{14}$ [M+H]$^+$ 928.3041, found 928.3038.

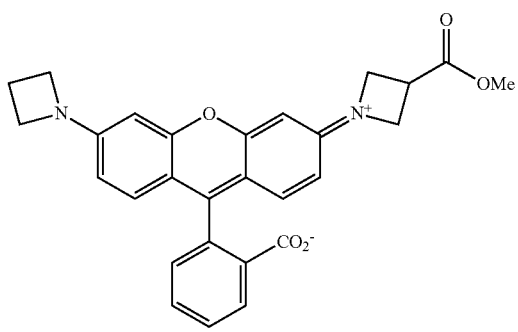

3"-methoxycarbonyl-JF$_{549}$ (S16): A vial was charged with S12 (150 mg, 0.30 mmol), Pd$_2$dba$_3$ (27.3 mg, 0.030 mmol, 0.1 eq), XPhos (43 mg, 0.090 mmol, 0.3 eq), Cs$_2$CO$_3$ (372 mg, 1.14 mmol, 3.8 eq), and methyl 3-azetidinecarboxylate hydrochloride (114 mg, 0.75 mmol, 2.5 eq). The vial was sealed under argon. Dioxane (6 mL) was added. The reaction was stirred at 100° C. for 20 h. It was subsequently cooled to room temperature, diluted with MeOH, deposited onto Celite and concentrated to dryness. Purification by silica gel chromatography (0-10% MeOH (2 M NH$_3$)/CH$_2$Cl$_2$, linear gradient) provided S16 as a pink solid (112 mg, 80%). $^1$H NMR (CD$_3$OD, 400 MHz) δ 8.09-8.07 (m, 1H), 7.67-7.60 (m, 2H), 7.22-7.19 (m, 1H), 7.14 (dd, J=9.1, 3.3 Hz, 2H), 6.54-6.50 (m, 2H), 6.49 (d, J=2.2 Hz, 1H), 6.41-6.40 (m, 1H), 4.39 (t, J=9.1 Hz, 2H), 4.30 (dd, J=9.4, 5.8 Hz, 2H), 4.23 (t, J=7.6 Hz, 4H), 3.79 (s, 3H), 3.78-3.70 (m, 1H), 2.53 (dq, J=11.4, 7.5 Hz, 2H); $^{13}$C NMR (CD$_3$OD, 101 MHz) δ 174.2 (C), 172.9 (C), 158.0 (C), 157.7 (C), 157.5 (C), 156.9 (C), 149.9 (C), 139.2 (C), 137.7 (C), 132.6 (CH), 132.4 (CH), 131.6 (CH), 130.8 (CH), 130.0 (CH), 129.4 (CH), 114.24 (C), 114.19 (C), 112.5 (CH), 112.1 (CH), 96.3 (CH), 95.7 (CH), 55.1 (CH$_2$), 52.89 (CH), 52.85 (CH$_2$), 33.9 (CH$_3$), 17.0 (CH$_2$); HRMS (ESI) calcd for C$_{28}$H$_{25}$N$_2$O$_5$ [M+H]$^+$ 469.1763, found 469.1759.

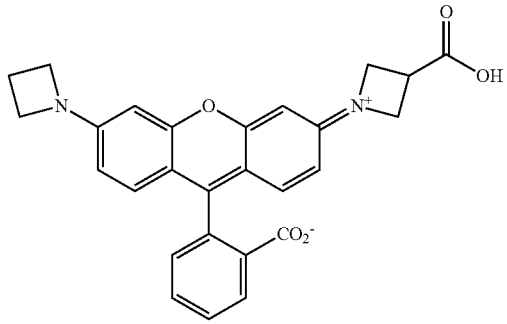

3"-carbonyl-JF$_{549}$ (S17): S16 (94 mg, 0.20 mmol) was taken up in THF/MeOH (1/1: 6 mL) and NaOH (1 M in H$_2$O, 800 μL, 0.80 mmol, 4.0 eq) was added. The reaction was stirred at room temperature for 5 h. It was subsequently neutralized with HCl 1 M (850 μL). The residue was diluted with H$_2$O and the organics were evaporated. The aqueous layer was extracted with CHCl$_3$/iPrOH (85/15). The combined organic layers were dried over MgSO$_4$, filtered and evaporated to afford S17 as a dark pink solid (76 mg, 83%). The material was used without further purification. $^1$H NMR (CD$_3$OD, 400 MHz) δ 8.19 (dd, J=6.0, 3.2 Hz, 1H), 7.74-7.69 (m, 2H), 7.29 (dd, J=5.9, 3.0 Hz, 1H), 7.12 (dd, J=9.1, 2.5 Hz, 2H), 6.57 (td, J=9.0, 2.2 Hz, 2H), 6.50 (dd, J=17.5, 2.2 Hz, 2H), 4.42-4.24 (m, 8H), 3.64-3.57 (m, 1H), 2.54 (p, J=7.6 Hz, 2H); $^{13}$C NMR (CD$_3$OD, 101 MHz) δ 177.1 (C), 170.6 (C), 158.9 (C), 158.6 (C), 158.4 (C), 157.8 (C), 157.5 (C), 136.4 (C), 135.7 (C), 132.6 (CH), 132.5 (CH), 132.4 (CH), 131.5 (CH), 131.1 (CH), 130.7 (CH), 114.9 (C), 114.8 (C), 113.2 (CH), 113.0 (CH), 95.6 (CH), 95.3 (CH), 55.7 (CH$_2$), 52.8 (CH$_2$), 35.0 (CH), 16.9 (CH$_2$); HRMS (ESI) calcd for C$_{27}$H$_{23}$N$_2$O$_5$ [M+H]$^+$ 455.1607, found 455.1606.

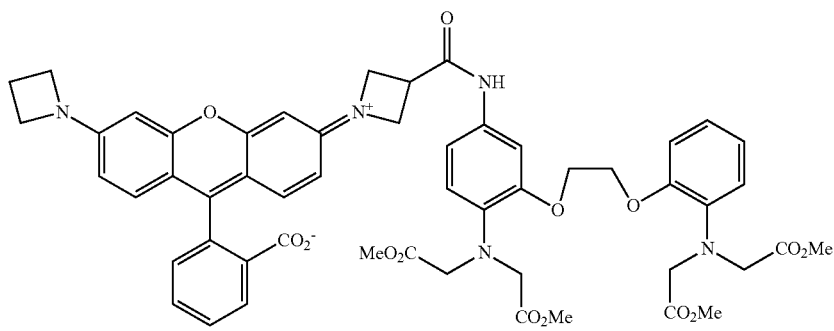

3″-BAPTA-JF$_{549}$ tetramethyl ester (S18): A vial was charged with S17 (15 mg, 0.033 mmol), 11[5] (22 mg, 0.040 mmol, 1.2 eq), EDC·HCl (9.5 mg, 0.050 mmol, 1.5 eq) and DMAP (0.8 mg, 0.0066 mmol, 0.2 eq) CH$_2$Cl$_2$ (3 mL) was added. The mixture was stirred at room temperature for 1 h and concentrated to dryness. Purification by silica gel chromatography (0-10% MeOH (2 M NH$_3$)/CH$_2$Cl$_2$, linear gradient) provided S18 as a dark pink solid (16 mg, 49%). $^1$H NMR (CD$_3$OD, 400 MHz) δ 8.09 (dd, J=7.1, 1.8 Hz, 1H), 7.65-7.57 (m, 2H), 7.35 (d, J=2.3 Hz, 1H), 7.20-7.16 (m, 1H), 7.11-7.06 (m, 2H), 7.03 (dd, J=8.6, 2.3 Hz, 1H), 6.95-6.79 (m, 5H), 6.51-6.42 (m, 3H), 6.36 (d, J=2.2 Hz, 1H), 4.31-4.23 (m, 8H), 4.17 (t, J=7.5 Hz, 4H), 4.10 (d, J=4.8 Hz, 8H), 3.68 (p, J=7.1 Hz, 1H), 3.58-3.55 (m, 12H), 2.48 (p, J=7.5 Hz, 2H); Analytical HPLC: t$_R$=12.3 min, 98% purity (10-95% MeCN/H$_2$O, linear gradient, with constant 0.1% v/v TFA additive, 20 min run, 1 mL/min flow, detection at 254 nm); HRMS (ESI) calcd for C$_{53}$H$_{54}$N$_5$O$_{14}$ [M+H]$^+$ 984.3667, found 984.3653.

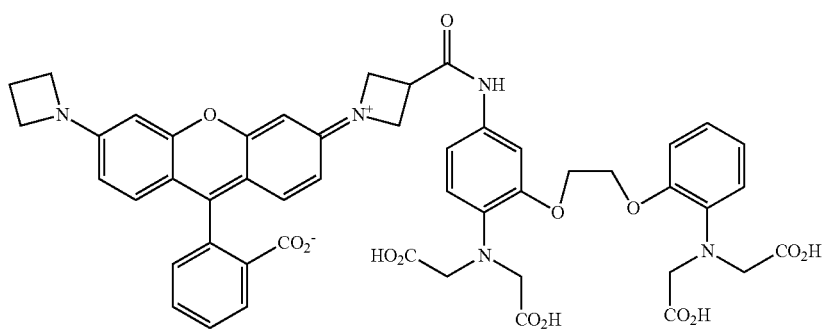

3″-BAPTA-JF$_{549}$ (7): To a solution of S18 (23 mg, 0.023 mmol) in THF/MeOH (1/1: 3 mL) was added KOH (1 M in H$_2$O, 380 μL, 0.38 mmol, 16 eq). The mixture was stirred at room temperature for 7 h. It was subsequently neutralized with HCl 1 M, concentrated and diluted with MeOH. Purification by reverse phase HPLC (35-45% MeCN/H$_2$O, linear gradient, with constant 0.1% v/v TFA additive) afforded 7 as a dark pink solid (10.7 mg, 44%, TFA salt). $^1$H NMR (CD$_3$OD, 400 MHz) δ 8.33 (dd, J=7.7, 1.4 Hz, 1H), 7.87-7.77 (m, 2H), 7.45 (br s, 1H), 7.39 (d, J=7.3 Hz, 1H), 7.12-6.87 (m, 8H), 6.67-6.60 (m, 3H), 6.53-6.51 (m, 1H), 4.49-4.28 (m, 12H), 4.03-4.01 (s, 8H), 3.81 (br s, 1H), 2.56 (p, J=7.5 Hz, 2H); Analytical HPLC: t$_R$=8.8 min, 99% purity (30-60% MeCN/H$_2$O, linear gradient, with constant 0.1% v/v TFA additive, 20 min run, 1 mL/min flow, detection at 254 nm); HRMS (ESI) calcd for C$_{49}$H$_{46}$N$_5$O$_{14}$ [M+H]$^+$ 928.3041, found 928.3045.

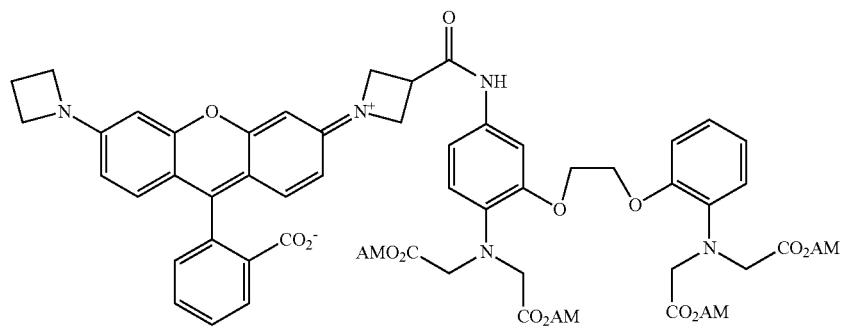

15

3''-BAPTA-JF$_{549}$ tetra-acetoxymethyl ester ($7_{AM}$): A vial was charged with S17 (12 mg, 0.027 mmol), S197 (25 mg, 0.032 mmol, 1.2 eq), EDC·HCl (7.8 mg, 0.041 mmol, 1.5 eq) and DMAP (0.7 mg, 0.0054 mmol, 0.2 eq). CH$_2$Cl$_2$ (4 mL) was added. The mixture was stirred at room temperature for 24 h after which additional S19 (8 mg, 0.010 mmol, 0.4 eq) was added to complete the reaction. The mixture was stirred for an additional 24 h. It was subsequently concentrated to dryness. Purification by reverse phase HPLC (30-70% MeCN/H$_2$O, linear gradient, with constant 0.1% v/v TFA additive) afforded 7AM as a dark pink solid (8.2 mg, 23%, TFA salt). $^1$H NMR (CDC$_3$, 400 MHz) δ 8.33 (d, J=7.7 Hz, 1H), 7.86-7.77 (m, 2H), 7.44 (d, J=2.2 Hz, 1H), 7.39 (d, J=7.4 Hz, 1H), 7.11-7.08 (m, 2H), 7.03-6.91 (m, 3H), 6.90-6.83 (m, 3H), 6.68-6.60 (m, 3H), 6.54 (d, J=2.2 Hz, 1H), 5.62-5.58 (m, 8H), 4.50-4.40 (m, 4H), 4.35-4.29 (m, 8H), 4.19-4.15 (m, 8H), 3.79 (s, 1H), 2.61-2.53 (m, 2H), 2.04-1.99 (m, 12H); Analytical HPLC: $t_R$=13.2 min, 99% purity (30-70% MeCN/H$_2$O, linear gradient, with constant 0.1% v/v TFA additive, 20 min run, 1 mL/min flow, detection at 254 nm); HRMS (ESI) calcd for C$_{61}$H$_{62}$N$_5$O$_{22}$ [M+H]$^+$ 1216.3886, found 1216.3890.

Example 9: Synthesis of Exemplary Compounds Including Compound 8

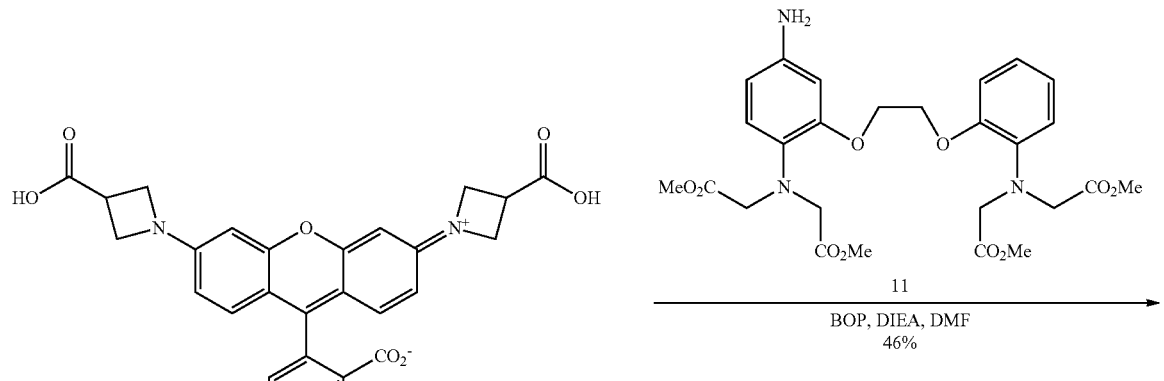

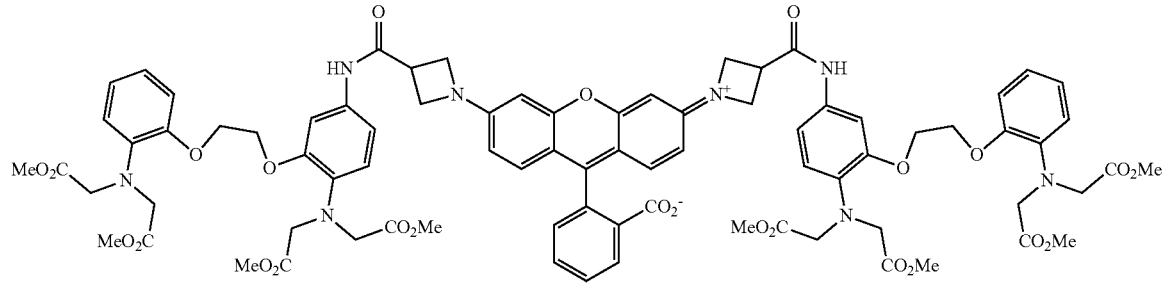

3",3'"-bisBAPTA-JF$_{549}$ octamethyl ester (S21): To a solution of S20[8] (11 mg, 0.022 mmol), 115 (25 mg, 0.046 mmol, 1.1 eq) and BOP (29.2 mg, 0.066 mmol, 1.1 eq) in DMF (3 mL) was added DIEA (38 μL, 0.22 mmol, 10 eq). The mixture was stirred at room temperature for 3 h and concentrated to dryness. The residue was purified by reverse phase HPLC (30-70% MeCN/H$_2$O, linear gradient, with constant 0.1% v/v TFA additive). The fractions were washed with NaHCO$_3$(sat), extracted with CH$_2$Cl$_2$ (3×). The combined organic extracts were dried over MgSO$_4$, filtered, and evaporated to afford S21 as a dark pink solid (15.8 mg, 46%). The material was used without further purification. $^1$H NMR (CDCl$_3$, 400 MHz) δ 9.09 (br s, 2H), 8.09 (d, J=7.3 Hz, 1H), 7.66-7.58 (m, 2H), 7.41 (s, 2H), 7.15 (dd, J=17.9, 7.8 Hz, 3H), 6.92-6.80 (m, 8H), 6.76-6.72 (m, 4H), 6.17-6.09 (m, 4H), 4.23-4.18 (m, 8H), 4.13-4.04 (m, 24H), 3.93-3.84 (m, 2H), 3.56 (s, 12H), 3.53 (s, 12H); Analytical HPLC: t$_R$ 13.4 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{80}$H$_{85}$N$_8$O$_{25}$ [M+H]$^+$ 1557.5626, found 1557.5620.

3",3'"-bisBAPTA-JF$_{549}$(8): To a solution of S21 (14 mg, 0.0090 mmol) in THF/MeOH (1/1: 2.5 mL) was added KOH (1 M in H$_2$O, 324 μL, 0.324 mmol, 36 eq). The mixture was stirred at room temperature for 3 h. It was subsequently neutralized with HCl 1 M, concentrated and diluted with MeOH. Purification by reverse phase HPLC (30-55% MeCN/H$_2$O, linear gradient, with constant 0.1% v/v TFA additive) afforded 8 as a dark pink solid (8.5 mg, 60%, TFA salt). $^1$H NMR (CD$_3$OD, 400 MHz) δ 8.34 (d, J=7.7 Hz, 1H), 7.87-7.77 (m, 2H), 7.43-7.39 (m, 3H), 7.13 (d, J=9.2 Hz, 2H), 7.06-6.99 (m, 4H), 6.97-6.85 (m, 8H), 6.69 (d, J=9.3 Hz, 2H), 6.63 (s, 2H), 4.54-4.43 (m, 8H), 4.34 (br s, 8H), 4.05 (br s, 16H), 3.84-3.78 (m, 2H); Analytical HPLC: t$_R$=10.1 min, 97% purity (10-95% MeCN/H$_2$O, linear gradient, with constant 0.1% v/v TFA additive, 20 min run, 1 mL/min flow, detection at 254 nm); HRMS (ESI) calcd for C$_{72}$H$_{69}$N$_8$O$_{25}$ [M+H]$^+$ 1445.4374, found 1445.4376.

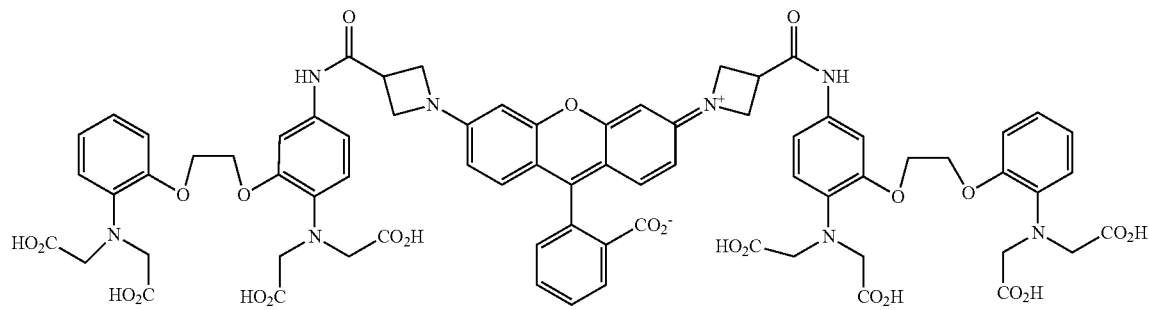

Example 10: Synthesis of Exemplary Compounds Including Compound 9

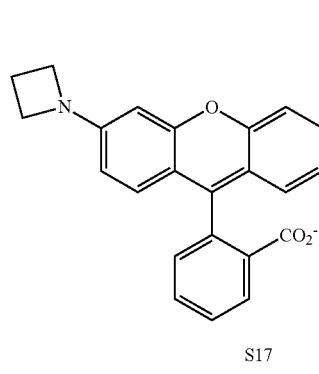

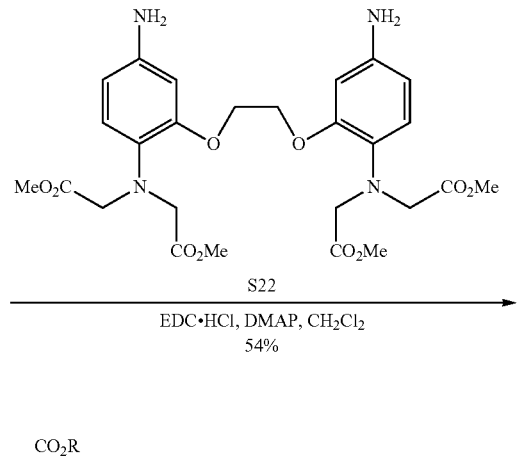

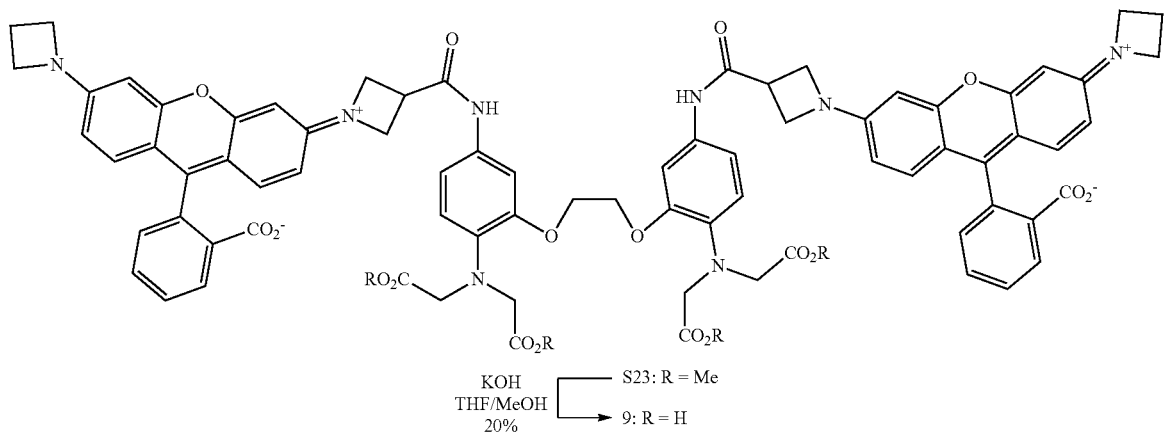

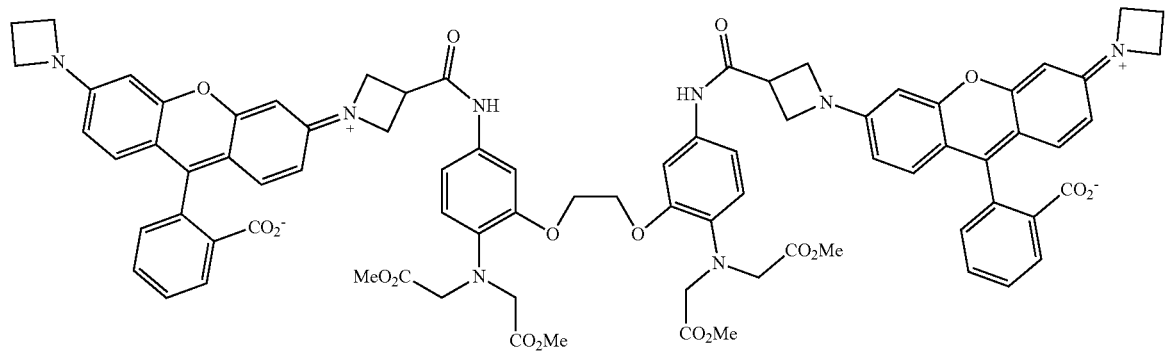

δ 9.95 (s, 2H), 7.97 (dd, J=7.6, 1.2 Hz, 2H), 7.77 (td, J=7.5, 1.3 Hz, 2H), 7.70 (td, J=7.4, 1.1 Hz, 2H), 7.32 (d, J=2.3 Hz, 2H), 7.23 (d, J=7.8 Hz, 2H), 7.05-7.01 (m, 2H), 6.70-6.64

3''-BAPTA-bisJF$_{549}$ tetramethyl ester (S23): A vial was charged with S17 (14 mg, 0.031 mmol, 2.0 eq), S22[9] (9.5 mg, 0.017 mmol, 1.1 eq), EDC·HCl (8.9 mg, 0.046 mmol, 3.0 eq) and DMAP (0.8 mg, 0.0065 mmol, 0.4 eq). CH$_2$Cl$_2$ (2 mL) was added. The mixture was stirred at room temperature for 4 h and concentrated to dryness. The residue was triturated and washed with MeOH (2×) to afford S23 as a dark pink solid (12 mg, 54%). The material was used without further purification. $^1$H NMR ((CD$_3$)$_2$SO, 400 MHz) (m, 2H), 6.48 (t, J=8.5 Hz, 4H), 6.30-6.28 (m, 2H), 6.24-6.19 (m, 4H), 6.16 (dd, J=8.6, 2.3 Hz, 2H), 4.15 (br s, 4H), 4.10-4.05 (m, 12H), 3.97-3.93 (m, 4H), 3.85 (t, J=7.3 Hz, 8H), 3.65 (p, J=7.3 Hz, 2H), 3.47 (s, 12H), 2.31 (p, J=7.0 Hz, 4H); Analytical HPLC: t$_R$=11.8 min, 80% purity (10-95% MeCN/H$_2$O, linear gradient, with constant 0.1% v/v TFA additive, 20 min run, 1 mL/min flow, detection at 254 nm); HRMS(ESI) calcd for C$_{80}$H$_{75}$N$_8$O is [M+H]$^+$ 1435.5199, found 1435.5200.

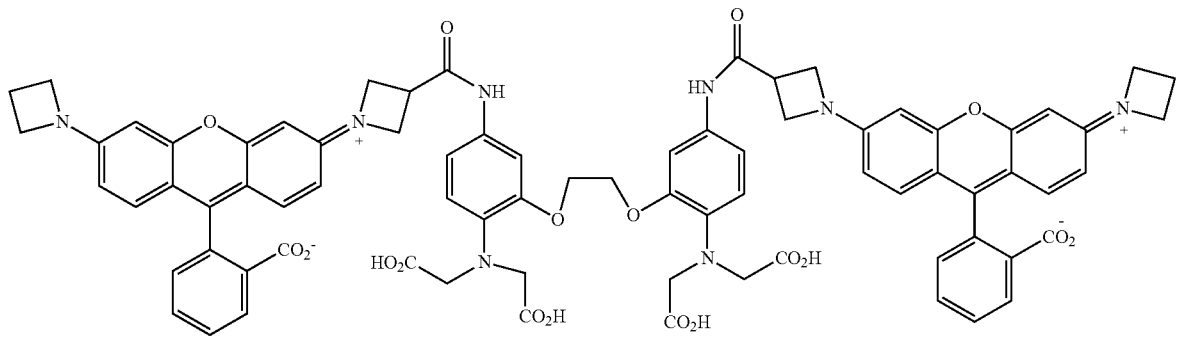

3''-BAPTA-bisJF$_{549}$ (9): To a solution of S23 (12 mg, 0.0084 mmol) in THF/MeOH (1/1: 2 mL) was added KOH (1 M in H$_2$O, 150 μL, 0.15 mmol, 18 eq). The mixture was stirred at room temperature for 2 h. It was subsequently neutralized with HCl 1 M, concentrated and diluted with MeOH. Purification by reverse phase HPLC (20-70% MeCN/H$_2$O, linear gradient, with constant 0.1% v/v TFA additive) afforded 9 as a dark pink solid (2.5 mg, 20%, TFA salt). $^1$H NMR (CD$_3$OD, 400 MHz) δ 8.33 (d, J=7.7 Hz, 2H), 7.86-7.76 (m, 4H), 7.40-7.32 (m, 4H), 7.12-7.06 (m, 6H), 6.88 (d, J=8.5 Hz, 2H), 6.67-6.55 (m, 6H), 6.50 (d, J=7.6 Hz, 2H), 4.49-4.27 (m, 20H), 4.07 (br s, 8H), 3.72 (q, J=6.6 Hz, 2H), 2.59-2.53 (m, 4H); Analytical HPLC: $t_R$=10.6 min, 96% purity (10-95% MeCN/H$_2$O, linear gradient, with constant 0.1% v/v TFA additive, 20 min run, 1 mL/min flow, detection at 254 nm); HRMS(ESI) calcd for C$_{76}$H$_{67}$N$_8$O$_{18}$ [M+H]$^+$ 1379.4573, found 1379.4559.

Example 11: Synthesis of Exemplary Compounds Including Compounds 12 and 12$_{AM}$

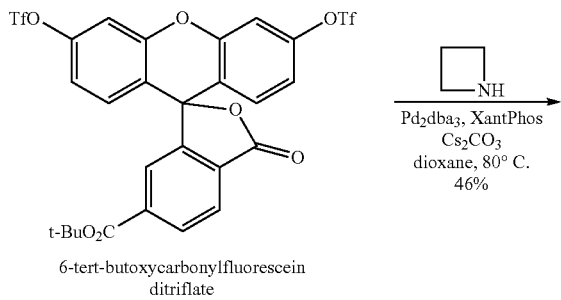

6-tert-butoxycarbonylfluorescein ditriflate

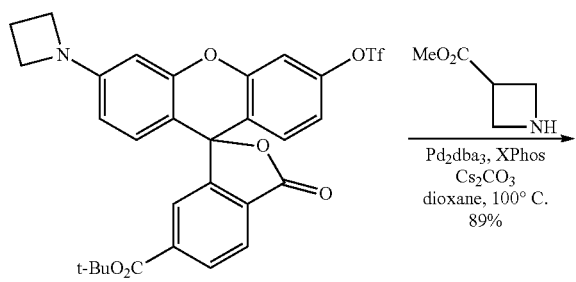

S24

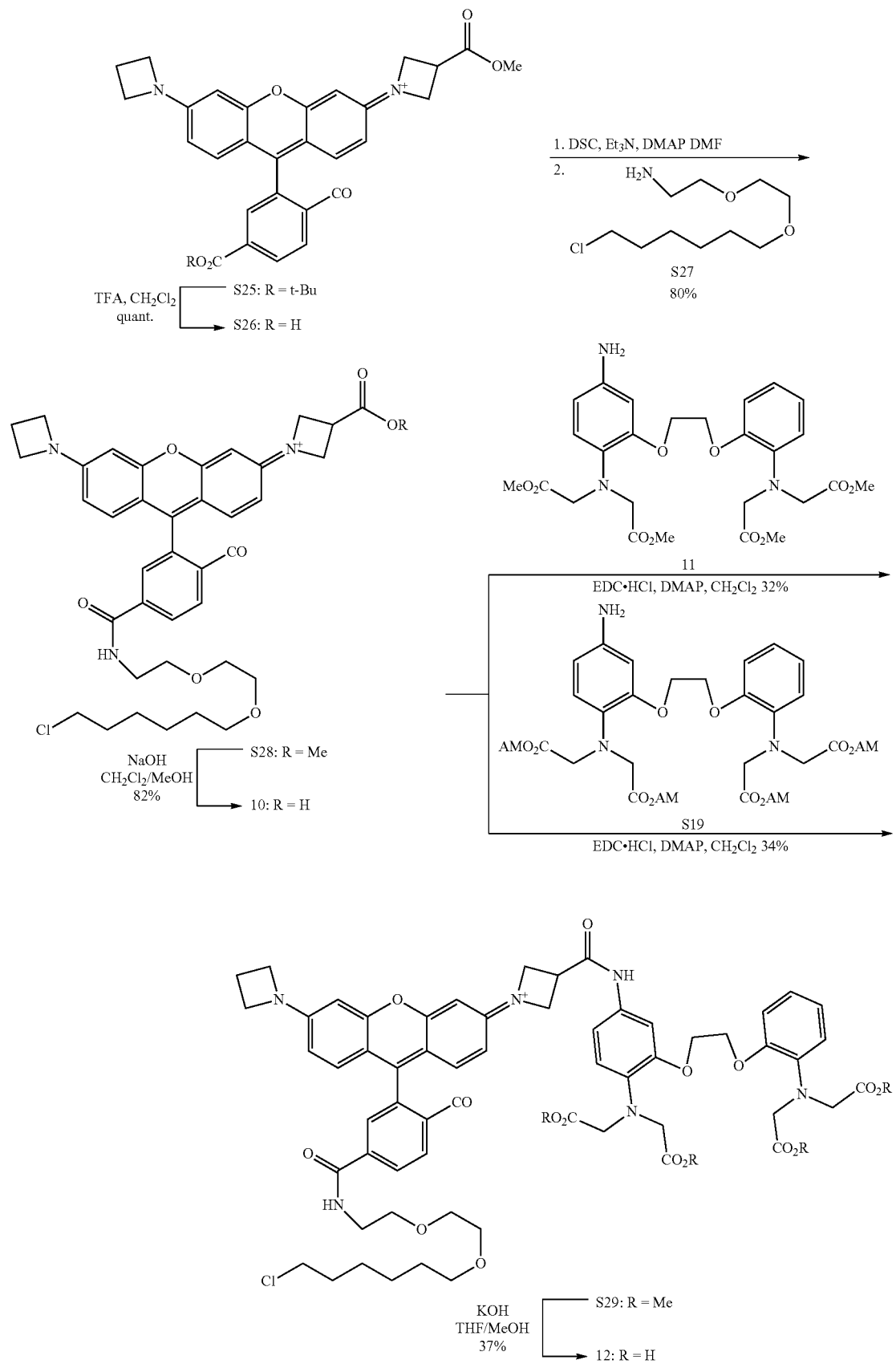

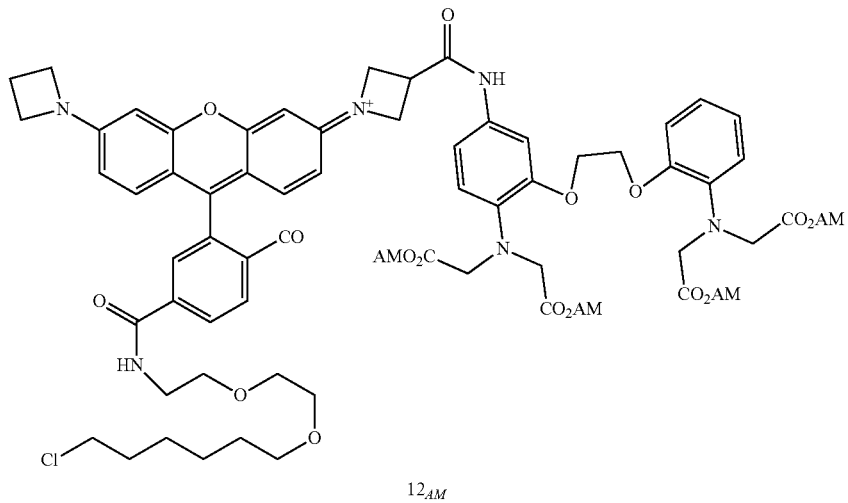

12<sub>AM</sub>

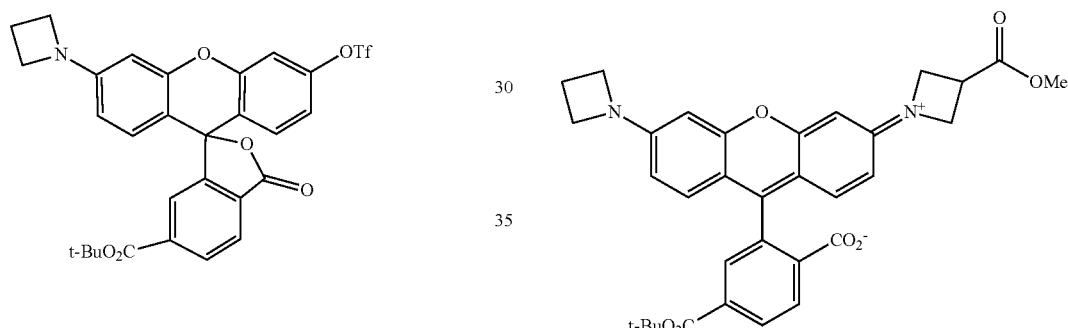

30

35

6-tert-butoxycarbonyl-JF$_{549}$ triflate (S24): A vial was charged with 6-tert-butoxycarbonylfluorescein ditriflate[6] (500 mg, 0.717 mmol), Pd$_2$dba$_3$ (33 mg, 0.036 mmol, 0.05 eq), XantPhos (62.3 mg, 0.108 mmol, 0.15 eq), and Cs$_2$CO$_3$ (327 mg, 1.00 mmol, 1.4 eq). The vial was sealed under argon. Dioxane (10 mL) and then azetidine (49 µL, 0.72 mmol, 1.0 eq) were added. The reaction was stirred at 80° C. for 2 h. It was subsequently cooled to room temperature, diluted with CH$_2$Cl$_2$, filtered through Celite and concentrated to dryness. Purification by silica gel chromatography (0-25% EtOAc/hexanes, linear gradient) provided S24 as an off-white solid (202 mg, 46%). 1H NMR (CDCl$_3$, 400 MHz) δ 8.23 (dd, J=8.0, 1.3 Hz, 1H), 8.06 (dd, J=8.0, 0.7 Hz, 1H), 7.74 (t, J=1.0 Hz, 1H), 7.22 (d, J=2.4 Hz, 1H), 6.93 (dd, J=8.8, 2.5 Hz, 1H), 6.84 (d, J=8.8 Hz, 1H), 6.56 (d, J=8.6 Hz, 1H), 6.24 (d, J=2.2 Hz, 1H), 6.14 (dd, J=8.6, 2.3 Hz, 1H), 3.94 (t, J=7.3 Hz, 4H), 2.41 (p, J=7.3 Hz, 2H), 1.56 (s, 9H); $^{19}$F NMR (CDCl$_3$, 376 MHz) δ -73.20; $^{13}$C NMR (CDCl$_3$, 101 MHz) δ 168.3 (C), 164.1(C), 153.8 (C), 152.7 (C), 152.4 (C), 152.0 (C), 150.1 (C), 138.6 (C), 131.2 (CH), 130.1 (CH), 129.8 (C), 128.7 (CH), 125.1 (CH), 125.0 (CH), 119.6 (C), 118.8 (q, $^1J_{CF}$=322.2 Hz, CF$_3$), 116.5 (CH), 110.5 (CH), 108.6 (CH), 105.6 (C), 97.5 (CH), 83.0 (C), 82.8 (C), 52.0 (CH$_2$), 28.1 (CH$_3$), 16.7 (CH$_2$); HRMS (ESI) calcd for C$_{29}$H$_{25}$NO$_8$SF$_3$ [M+H]$^+$ 604.1253, found 604.1255.

3''-methoxycarbonyl-6-tert-butoxycarbonyl-JF$_{49}$ (S25): A vial was charged with S24 (208 mg, 0.344 mmol), Pd$_2$dba$_3$ (32 mg, 0.034 mmol, 0.1 eq), XPhos (50 mg, 0.103 mmol, 0.3 eq), Cs$_2$CO$_3$ (426 mg, 1.31 mmol, 3.8 eq), and methyl 3-azetidinecarboxylate hydrochloride (131 mg, 0.86 mmol, 2.5 eq). The vial was sealed under argon. Dioxane (8 mL) was added. The reaction was stirred at 100° C. for 14 h. It was subsequently cooled to room temperature, diluted with MeOH, deposited onto Celite and concentrated to dryness. Purification by silica gel chromatography (0-10% MeOH (2 M NH$_3$)/CH$_2$Cl$_2$, linear gradient) provided S25 as a pink solid (175 mg, 89%). $^1$H NMR (CD$_3$OD, 400 MHz) δ 8.20 (dd, J=8.1, 1.7 Hz, 1H), 8.11 (d, J=8.1 Hz, 1H), 7.75 (d, J=1.6 Hz, 1H), 7.18-7.14 (m, 2H), 6.61-6.57 (m, 2H), 6.55 (d, J=2.2 Hz, 1H), 6.48 (d, J=2.2 Hz, 1H), 4.43 (t, J=9.3 Hz, 2H), 4.38-4.32 (m, 2H), 4.28 (t, J=7.6 Hz, 4H), 3.78 (s, 3H), 3.77-3.68 (m, 1H), 2.55 (p, J=7.7 Hz, 2H), 1.58 (s, 9H); $^{13}$C NMR (CD$_3$OD, 101 MHz) δ 174.1 (C), 171.9 (C), 165.9 (C), 158.3 (C), 157.9 (C), 157.6 (C), 157.1 (C), 155.8 (C), 144.6 (C), 135.4 (C), 134.2 (C), 132.7 (CH), 132.5 (CH), 131.6 (CH), 130.7 (CH), 130.6 (CH), 114.65 (C), 114.57 (C), 113.1 (CH), 112.6 (CH), 96.1 (CH), 95.4 (CH), 83.1 (C), 56.3 (C), 55.1 (CH$_2$), 52.95 (CH$_3$), 52.88 (CH$_2$), 33.8 (CH), 28.4 (CH$_3$), 16.9 (CH$_2$); HRMS (ESI) calcd for C$_{33}$H$_{33}$N$_2$O$_7$ [M+H]$^+$ 569.2288, found 569.2289.

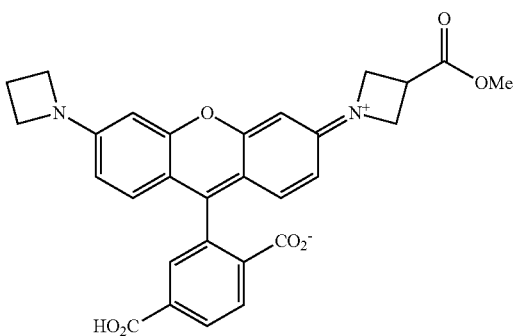

3"-methoxycarbonyl-6-carboxy-JF$_{549}$ (S26): S25 (80 mg, 0.14 mmol) was taken up in CH$_2$Cl$_2$ (5 mL) and trifluoroacetic acid (0.6 mL) was added. The reaction was stirred at room temperature for 8 h. Toluene (3 mL) was added, the reaction mixture was concentrated to dryness and then azeotroped with MeOH three times to provide S27 as a dark pink solid (90 mg, quantitative, TFA salt). The material was used without further purification. $^1$H NMR (CD$_3$OD, 400 MHz) δ 8.42-8.37 (m, 2H), 7.95 (d, J=1.5 Hz, 1H), 7.09-7.07 (m, 2H), 6.64-6.61 (m, 3H), 6.52 (d, J=2.2 Hz, 1H), 4.46 (t, J=9.7 Hz, 2H), 4.39-4.35 (m, 2H), 4.31 (t, J=7.7 Hz, 4H), 3.81-3.74 (m, 4H), 2.56 (p, J=7.7 Hz, 2H); $^{13}$C NMR (CD$_3$OD, 101 MHz) δ 174.1 (C), 167.7 (C), 167.3 (C), 160.6 (C), 159.0 (C), 158.6 (C), 158.3 (C), 157.7 (C), 136.0 (C), 135.9 (C), 135.4 (C), 132.9 (CH), 132.37 (CH), 132.34 (CH), 132.26 (CH), 132.2 (CH), 115.3 (C), 115.0 (C), 114.1 (CH), 113.5 (CH), 95.7 (CH), 95.1 (CH), 55.2 (CH$_2$), 52.99 (CH$_3$), 52.97 (CH$_2$), 33.8 (CH), 16.8 (CH$_2$); HRMS (ESI) calcd for C$_{29}$H$_{25}$N$_2$O$_7$ [M+H]$^+$ 513.1662, found 513.1661.

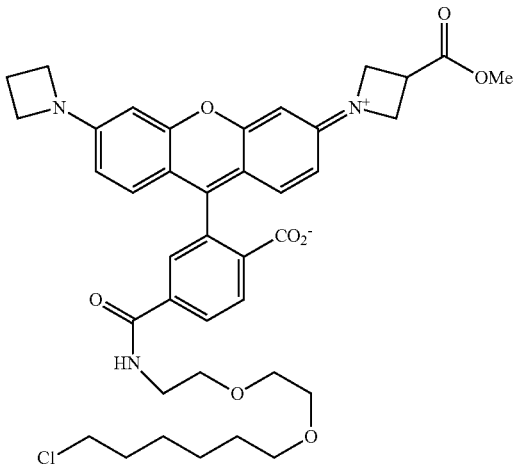

3"-methoxycarbonyl-JF$_{549}$-HaloTag ligand (S28): S26 (30 mg, 47.8 μmol) was combined with DSC (27 mg, 105 μmol, 2.2 eq) in DMF (2.5 mL). After adding Et$_3$N (40 μL, 287 mol, 6 eq) and DMAP (0.6 mg, 4.8 μmol, 0.1 eq), the reaction was stirred at room temperature for 1 h while shielded from light. HaloTag(O$_2$)amine S27 (TFA salt, 40 mg, 120 μmol, 2.5 eq) was then added. The reaction was stirred an additional 2 h at room temperature, after which excess HTL-NH$_2$ (1 eq) in 200 μL DMF was added to complete the reaction. After stirring for an additional 1 h at room temperature, NaHCO$_3$(sat) was added and the mixture was extracted with CH$_2$Cl$_2$ (3×). The combined organic layers were dried over MgSO$_4$, filtered and evaporated. Purification by silica gel chromatography (0-10% MeOH (2 M NH$_3$)/CH$_2$Cl$_2$, linear gradient) provided S28 as a pink solid (27 mg, 80%). The compound showed low stability and was immediately used in the next step. $^1$H NMR (CD$_3$OD, 400 MHz) δ 8.15 (d, J=8.1 Hz, 1H), 8.10 (dd, J=8.1, 1.8 Hz, 1H), 7.70 (d, J=1.7 Hz, 1H), 7.21 (d, J=3.1 Hz, 1H), 7.19 (d, J=3.2 Hz, 1H), 6.63-6.58 (m, 3H), 6.52 (d, J=2.2 Hz, 1H), 4.46 (t, J=9.4 Hz, 2H), 4.37 (dd, J=9.9, 5.7 Hz, 2H), 4.31 (t, J=7.6 Hz, 4H), 3.80 (s, 3H), 3.78-3.73 (m, 1H), 3.69-3.62 (m, 4H), 3.61-3.52 (m, 6H), 3.45 (t, J=6.5 Hz, 2H), 2.57 (p, J=7.6 Hz, 2H), 1.78-1.71 (m, 2H), 1.56-1.50 (m, 2H), 1.47-1.32 (m, 4H); Analytical HPLC: t$_R$=11.6 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{39}$H$_{45}$N$_3$O$_8$Cl [M+H]$^+$ 718.2895, found 718.2898.

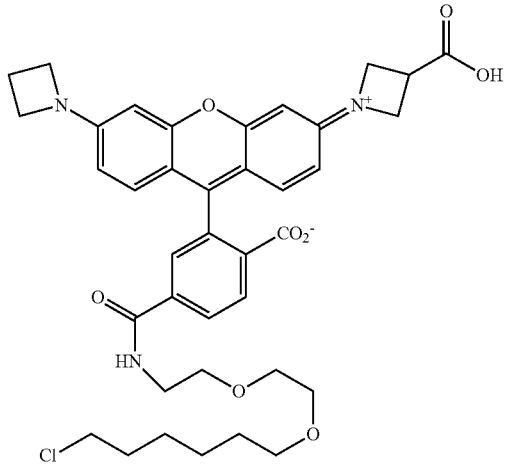

3"-carboxy-JF$_{549}$-HaloTag ligand (10): S28 (25 mg, 35 μmol) was taken up in CH$_2$Cl$_2$/MeOH (1/1: 6 mL) and NaOH (1 M in H$_2$O, 140 μL, 0.14 mmol, 4.0 eq) was added. The reaction was stirred at room temperature for 12 h. It was subsequently neutralized with HCl 1 M (160 sL). The residue was diluted with H$_2$O and the organics were evaporated. The aqueous layer was extracted with CH$_2$Cl$_2$/iPrOH (85/15). The combined organic extracts were dried over MgSO$_4$, filtered, and evaporated to afford 10 as a dark pink solid (20 mg, 82%). The material was used without further purification. $^1$H NMR (CD$_3$OD, 400 MHz) δ 8.24 (d, J=8.2 Hz, 1H), 8.13 (dd, J=8.1, 1.8 Hz, 1H), 7.73 (d, J=1.8 Hz, 1H), 7.15 (d, J=1.9 Hz, 1H), 7.13 (d, J=2.1 Hz, 1H), 6.62-6.56 (m, 3H), 6.51 (d, J=2.1 Hz, 1H), 4.42 (t, J=9.5 Hz, 2H), 4.38-4.32 (m, 2H), 4.29 (t, J=7.6 Hz, 4H), 3.68-3.60 (m, 5H), 3.59-3.50 (m, 6H), 3.43 (t, J=6.5 Hz, 2H), 2.55 (p, J=7.6 Hz, 2H), 1.72 (p, J=7.1 Hz, 2H), 1.50 (p, J=7.0 Hz, 2H), 1.45-1.37 (m, 2H), 1.36-1.30 (m, 2H); $^{13}$C NMR (CD$_3$OD, 101 MHz) δ 176.5 (C), 170.2 (C), 168.3 (C), 160.2 (C), 158.8 (C), 158.5 (C), 158.0 (C), 157.6 (C), 140.1 (C), 137.7 (C), 135.1 (C), 132.8 (CH), 132.7 (CH), 131.8 (CH), 129.8 (CH), 129.7 (CH), 115.1 (C), 114.9 (C), 113.5 (CH), 113.2 (CH), 95.6 (CH), 95.2 (CH), 72.1 (CH$_2$), 71.3 (CH$_2$), 71.2 (CH$_2$), 70.4 (CH$_2$), 55.6 (CH$_2$), 52.9 (CH$_2$), 45.7 (CH$_2$), 41.2 (CH$_2$), 34.6 (CH), 33.7 (CH$_2$), 30.5 (CH$_2$), 27.7 (CH$_2$), 26.4 (CH$_2$), 16.9 (CH$_2$); HRMS (ESI) calcd for C$_{38}$H$_{43}$N$_3$O$_8$Cl [M+H]$^+$ 704.2739, found 704.2735.

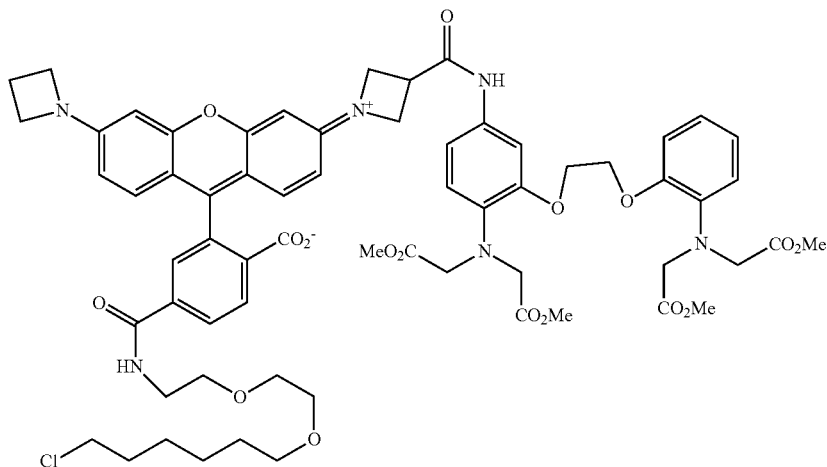

3"-BAPTA-JF$_{549}$-HaloTag ligand tetramethyl ester (S29): A vial was charged with 10 (12 mg, 0.017 mmol), 11[5] (11.2 mg, 0.020 mmol, 1.2 eq), and DMAP (0.4 mg, 0.0034 mmol, 0.2 eq) under argon. DMF (3 mL) was added followed by EDC·HCl (4.9 mg, 0.026 mmol, 1.5 eq). The mixture was stirred at room temperature for 11 h. It was subsequently concentrated to dryness. The residue was purified by reverse phase HPLC (20-80% MeCN/H$_2$O, linear gradient, with constant 0.1% v/v TFA additive). The fractions were washed with NaHCO$_3$(sat), extracted with CH$_2$Cl$_2$ (3×). The combined organic extracts were dried over MgSO$_4$, filtered, and evaporated to afford S29 as a dark pink solid (6.8 mg, 32%). $^1$H NMR (CD$_3$OD, 400 MHz) δ 8.05 (d, J=8.1 Hz, 1H), 7.98 (dd, J=8.1, 1.8 Hz, 1H), 7.60 (d, J=1.8 Hz, 1H), 7.25 (d, J=2.3 Hz, 1H), 7.11-7.06 (m, 2H), 6.94 (dd, J=8.6, 2.3 Hz, 1H), 6.85-6.65 (m, 5H), 6.51-6.42 (m, 3H), 6.35 (d, J=2.2 Hz, 1H), 4.27 (d, J=7.7 Hz, 4H), 4.18-4.10 (m, 8H), 4.02-4.00 (m, 8H), 3.67-3.60 (m, 1H), 3.56-3.49 (m, 4H), 3.49-3.39 (m, 18H), 3.32 (t, J=6.5 Hz, 2H), 2.43 (p, J=7.5 Hz, 2H), 1.64-1.57 (m, 2H), 1.43-1.35 (m, 2H), 1.33-1.21 (m, 4H); Analytical HPLC: t$_R$=13.0 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{64}$H$_{73}$N$_6$O$_{17}$ClNa [M+Na]$^+$ 1255.4618, found 1255.4615.

3"-BAPTA-JF$_{549}$-HaloTag ligand (12): To a solution of S29 (6.5 mg, 0.0053 mmol) in THF/MeOH (1/1: 2 mL) was added KOH (1 M in H$_2$O, 95 μL, 0.095 mmol, 18 eq). The mixture was stirred at room temperature for 5 h. It was subsequently neutralized with HCl 1 M and diluted with MeOH. Purification by reverse phase HPLC (30-70% MeCN/H$_2$O, linear gradient, with constant 0.1% v/v TFA additive) afforded 12 as a pink solid (2.5 mg, 37%, TFA salt). $^1$H NMR (CD$_3$OD, 400 MHz) δ 8.65 (s, 1H), 8.30 (d, J=8.3 Hz, 1H), 8.14-8.07 (m, 1H), 7.71 (d, J=1.7 Hz, 1H), 7.34 (s, 1H), 7.04-6.74 (m, 7H), 6.60-6.50 (m, 3H), 6.47 (d, J=2.1 Hz, 1H), 4.44-4.30 (m, 4H), 4.24 (d, J=8.3 Hz, 8H), 3.94 (s, 8H), 3.71 (s, 1H), 3.58-3.36 (m, 10H), 3.33 (t, J=6.5 Hz, 2H), 2.53-2.41 (m, 2H), 1.62 (p, J=6.8 Hz, 2H), 1.41 (p, J=7.1 Hz, 2H), 1.35-1.17 (m, 4H); Analytical HPLC: t$_R$=11.2 min, 97% purity (10-95% MeCN/H$_2$O, linear gradient, with constant 0.1% v/v TFA additive, 20 min run, 1 mL/min flow, detection at 254 nm); HRMS (ESI) calcd for C$_{60}$H$_{66}$N$_6$O$_{17}$Cl [M+H]$^+$ 1177.4173, found 1177.4179.

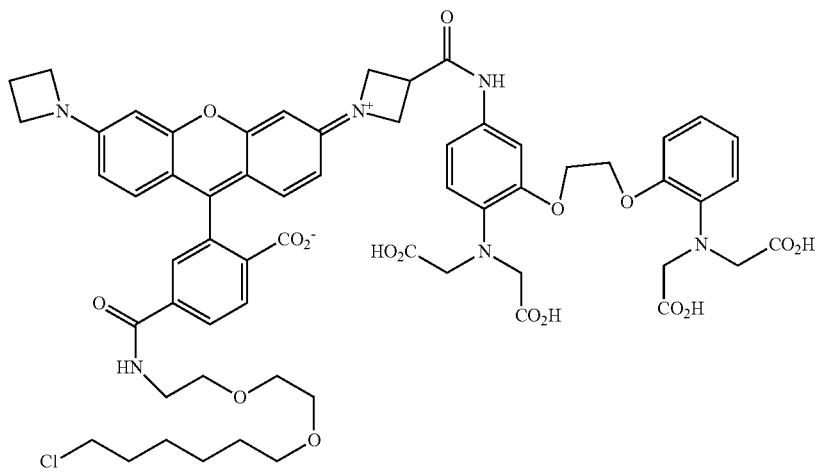

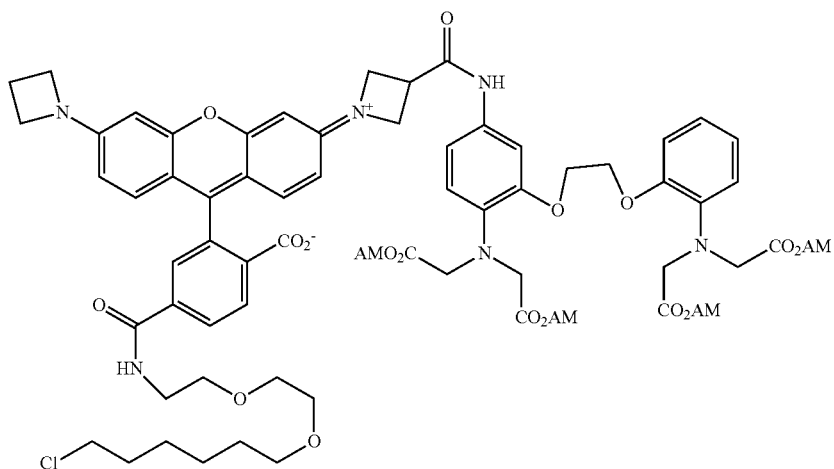

3"-BAPTA-JF$_{549}$-HaloTag ligand tetra acetoxymethyl ester (12AM): A vial was charged with 10 (7.5 mg, 0.011 mmol), S197 (9.8 mg, 0.013 mmol, 1.2 eq), and DMAP (0.3 mg, 0.0022 mmol, 0.2 eq) under argon. DMF (2 mL) was added and then EDC·HCl (3.0 mg, 0.041 mmol, 1.5 eq) were added. The mixture was stirred at room temperature for 8 h. It was subsequently concentrated to dryness. Purification by reverse phase HPLC (20-80% MeCN/H$_2$O, linear gradient, with constant 0.1% v/v TFA additive) afforded 12AM as a dark pink solid (5.9 mg, 34%, TFA salt). $^1$H NMR (CD$_3$OD, 400 MHz) δ 8.64 (t, J=5.5 Hz, 1H), 8.30 (d, J=8.2 Hz, 1H), 8.10 (dd, J=8.2, 1.8 Hz, 1H), 7.71 (d, J=1.8 Hz, 1H), 7.34 (d, J=2.3 Hz, 1H), 7.01-6.97 (m, 2H), 6.93-6.80 (m, 3H), 6.78-6.72 (m, 3H), 6.57-6.50 (m, 3H), 6.45 (d, J=2.1 Hz, 1H), 5.52-5.48 (m, 8H), 4.41-4.29 (m, 4H), 4.24-4.17 (m, 8H), 4.09-4.04 (m, 8H), 3.74-3.66 (m, 1H), 3.58-3.39 (m, 10H), 3.33 (t, J=6.5 Hz, 2H), 2.46 (p, J=7.6 Hz, 2H), 1.94-1.88 (m, 12H), 1.65-1.58 (m, 2H), 1.40 (p, J=6.7 Hz, 2H), 1.32-1.18 (m, 4H); Analytical HPLC: t$_R$=13.2 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{72}$H$_{82}$N$_6$O$_{25}$Cl [M+H]$^+$ 1465.5018, found 1465.4996.

Example 12: Synthesis of Exemplary Compounds Including Compounds 13 and 13$_{AM}$

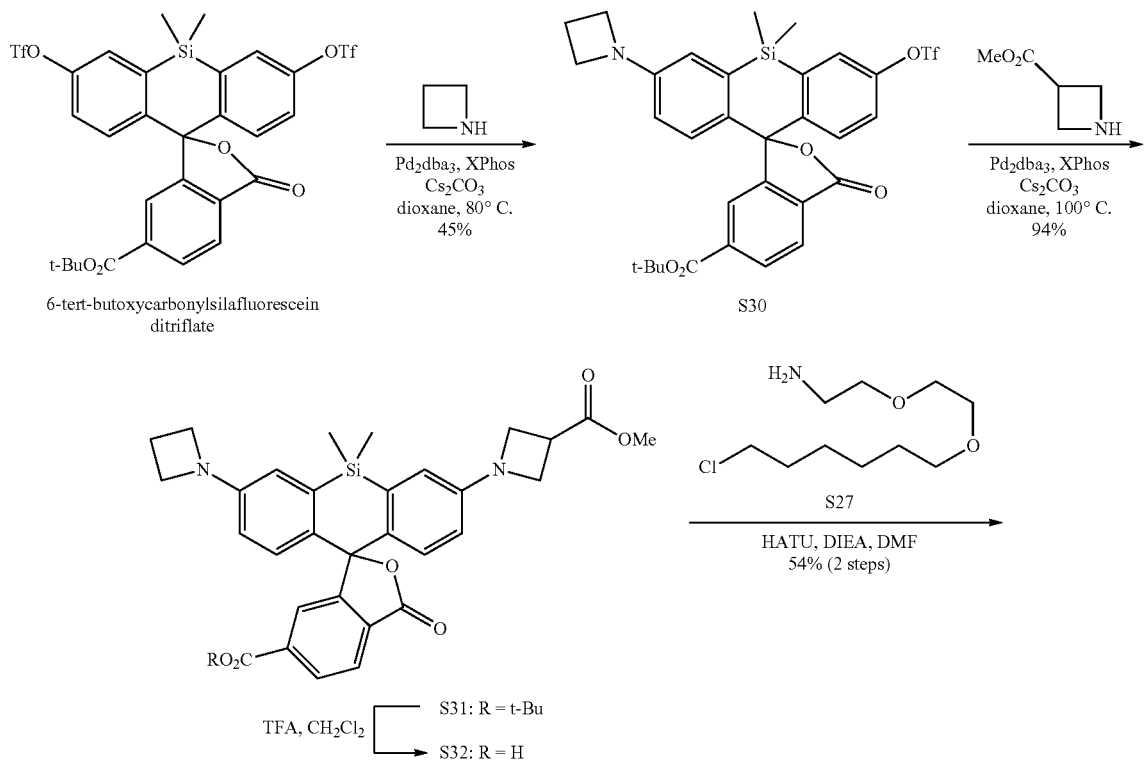

-continued
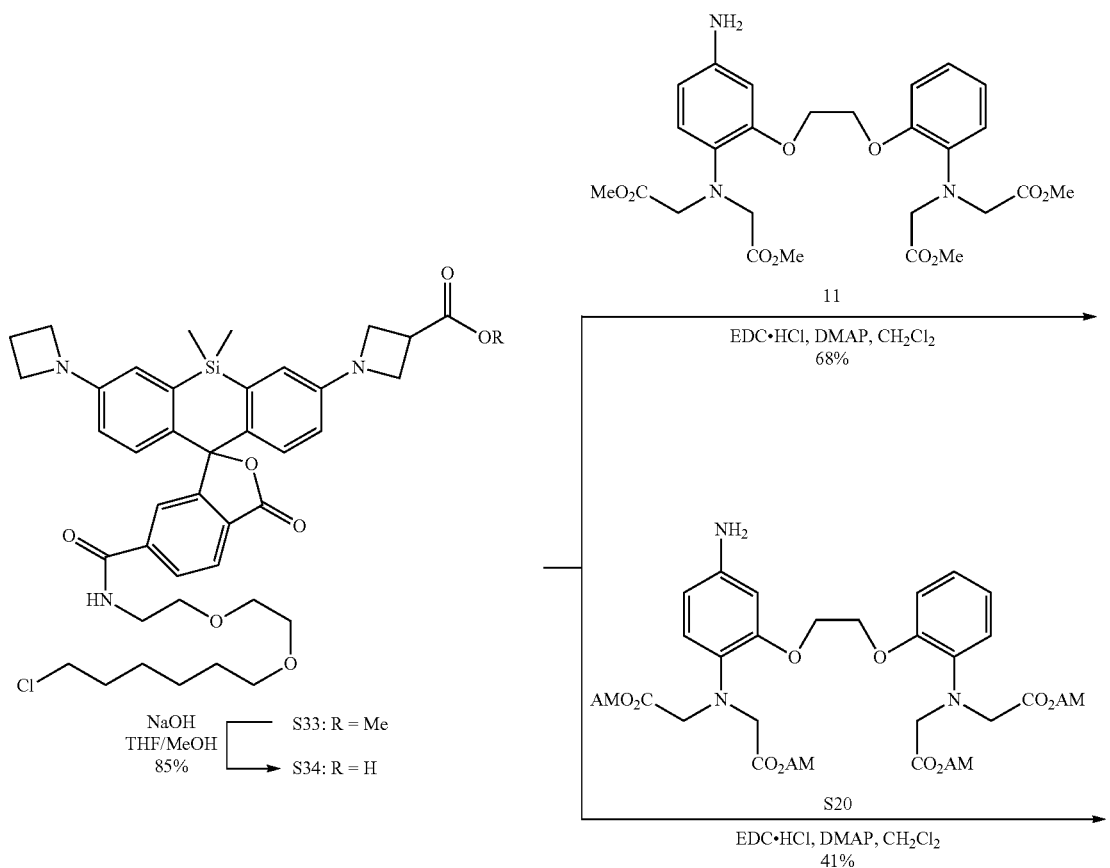
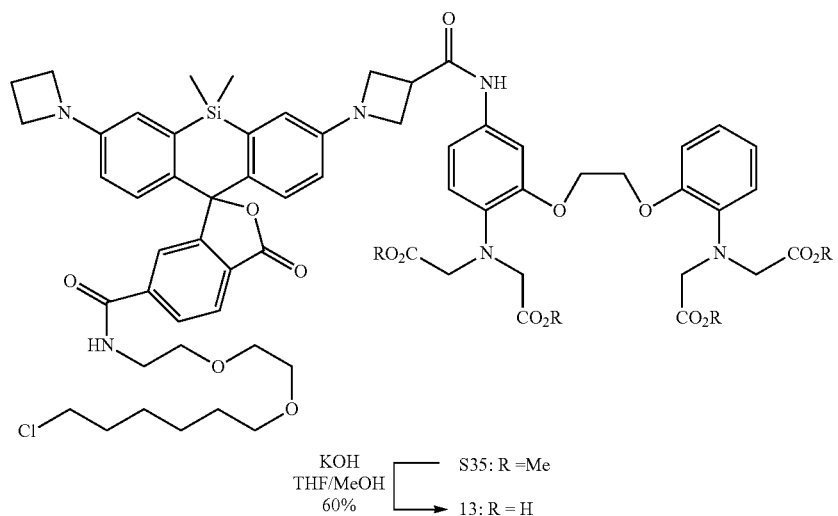

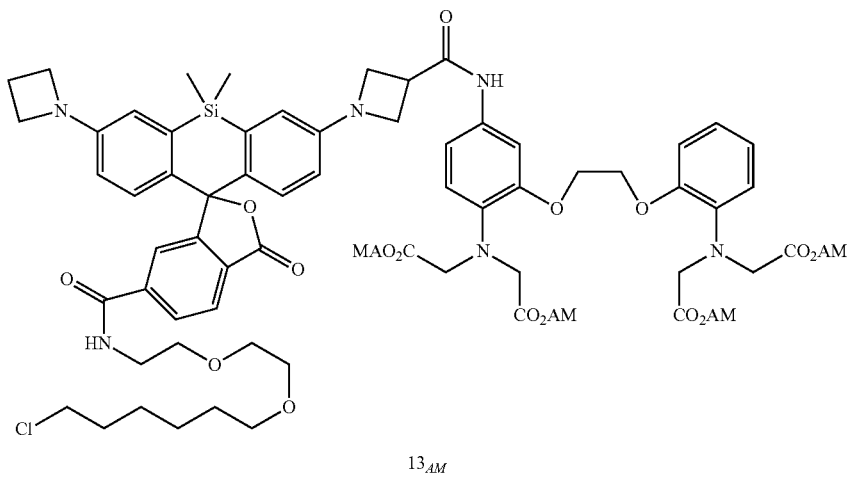

13_AM

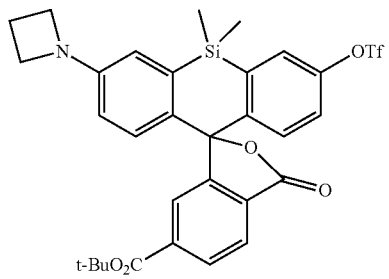

6-tert-butoxycarbonyl-JF$_{646}$ triflate (S30): A vial was charged with 6-tert-butoxycarbonylsilafluorescein ditriflate[6] (500 mg, 0.677 mmol), Pd$_2$dba$_3$ (62 mg, 0.068 mmol, 0.1 eq), XantPhos (118 mg, 0.203 mmol, 0.3eq), and Cs$_2$CO$_3$ (441 mg, 1.35 mmol, 2.0 eq). The vial was sealed under argon. Dioxane (10 mL) and then azetidine (46 µL, 0.68 mmol, 1.0 eq) were added. The reaction was stirred at 80° C. for 2 h. It was subsequently cooled to room temperature, diluted with CH$_2$Cl$_2$, filtered through Celite and concentrated to dryness. Purification by silica gel chromatography (0-20% EtOAc/hexanes, linear gradient) provided S30 as an off-white solid (198 mg, 45%). $^1$H NMR (CDCl$_3$, 400 MHz) δ 8.17 (dd, J=8.1, 1.3 Hz, 1H), 8.00 (dd, J=8.0, 0.7 Hz, 1H), 7.88 (d, J=1.0 Hz, 1H), 7.54 (d, J=2.4 Hz, 1H), 7.18-7.13 (m, 2H), 6.91 (d, J=8.7 Hz, 1H), 6.66 (d, J=2.6 Hz, 1H), 6.33 (dd, J=8.8, 2.6 Hz, 1H), 3.92 (t, J=7.2 Hz, 4H), 2.39 (p, J=7.2 Hz, 2H), 1.57 (s, 9H), 0.73 (s, 3H), 0.65 (s, 3H); $^{19}$F NMR (CDCl$_3$, 376 MHz) δ -73.41; $^{13}$C NMR (CDCl$_3$, 101 MHz) δ 169.6 (C), 164.2 (C), 154.0 (C), 151.2 (C), 149.3 (C), 145.1 (C), 140.0 (C), 137.7 (C), 134.8 (C), 131.0 (C), 130.6 (CH), 128.74 (CH), 128.72 (C), 127.7 (CH), 126.3 (CH), 126.2 (CH), 125.1 (CH), 122.4 (CH), 118.9 (q, $^1J_{CF}$=322.2 Hz, CF$_3$), 115.7 (CH), 112.9 (CH), 90.3 (C), 82.7 (C), 52.3 (CH$_2$), 28.2 (CH$_3$), 17.0 (CH$_2$), 0.0 (CH$_3$), -0.9 (CH$_3$); HRMS (ESI) calcd for C$_{31}$H$_{31}$NO$_7$SF$_3$Si [M+H]$^+$ 646.1543, found 646.1549.

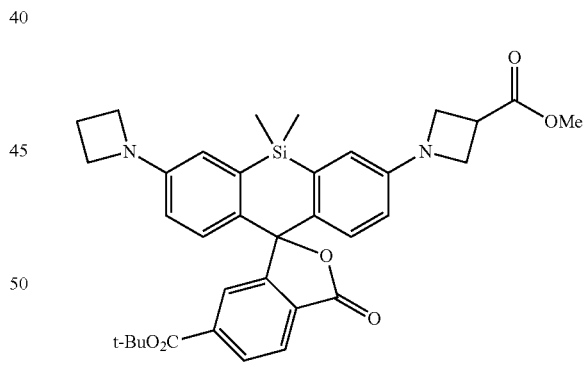

3″-methoxycarbonyl-6-tert-butoxycarbonyl-JF$_{646}$ (S31): A vial was charged with S30 (180 mg, 0.279 mmol), Pd$_2$dba$_3$ (26 mg, 0.028 mmol, 0.1 eq), XPhos (40 mg, 0.084 mmol, 0.3 eq), Cs$_2$CO$_3$ (437 mg, 1.33 mmol, 4.8 eq), and methyl 3-azetidinecarboxylate hydrochloride (128 mg, 0.84 mmol, 3.0 eq). The vial was sealed under argon. Dioxane (8 mL) was added. The reaction was stirred at 100° C. for 4 h. It was subsequently cooled to room temperature, diluted with MeOH, deposited onto Celite and concentrated to dryness. Purification by silica gel chromatography (0-40% EtOAc/hexanes, linear gradient) followed by a second purification (0-10% EtOAc/CH$_2$Cl$_2$, linear gradient) provided S31 as an off-white solid (160 mg, 94%). $^1$H NMR (CDCl3, 400 MHz)

δ 8.11 (dd, J=8.0, 1.3 Hz, 1H), 7.96 (dd, J=8.0, 0.7 Hz, 1H), 7.81 (s, 1H), 6.88-6.83 (m, 2H), 6.70-6.68 (m, 2H), 6.35-6.31 (m, 2H), 4.15-4.09 (m, 2H), 4.08-4.02 (m, 2H), 3.91 (t, J=7.3 Hz, 4H), 3.74 (s, 3H), 3.61-3.52 (m, 1H), 2.37 (p, J=7.3 Hz, 2H), 1.55 (s, 9H), 0.65 (s, 3H), 0.58 (s, 3H); $^{13}$C NMR (CDCl3, 101 MHz) δ 173.2 (C), 170.3 (C), 164.4 (C), 155.3 (C), 150.9 (C), 150.2 (C), 137.3 (C), 136.4 (C), 136.0 (C), 133.4 (C), 132.4 (C), 130.0 (CH), 129.1 (C), 127.68 (CH), 127.66 (CH), 125.7 (CH), 125.1 (CH), 116.0 (CH), 115.7 (CH), 112.9 (CH), 112.8 (CH), 91.6 (C), 82.4 (C), 54.54 (CH$_2$), 54.52 (CH$_2$), 52.4 (CH$_2$), 52.3 (CH$_3$), 33.6 (CH), 28.2 (CH$_3$), 17.0 (CH$_2$), 0.2 (CH$_3$), −0.7 (CH$_3$); HRMS (ESI) calcd for $C_{35}H_{39}N_2O_6Si$ [M+H]$^+$ 611.2577, found 611.2583

136.5 (C), 133.2 (C), 132.1 (C), 128.9 (C), 127.92 (CH), 127.90 (CH), 127.6 (CH), 126.0 (CH), 123.5 (CH), 116.0 (CH), 115.7 (CH), 112.8 (CH), 112.5 (CH), 92.0 (C), 71.3 (CH$_2$), 70.3 (CH$_2$), 70.1 (CH$_2$), 69.6 (CH$_2$), 54.53 (CH$_2$), 54.51 (CH$_2$), 52.3 (CH$_2$), 45.1 (CH$_2$), 40.1 (CH$_2$), 33.6 (CH), 32.6 (CH$_2$), 29.43 (CH$_2$), 29.37 (CH$_3$), 26.7 (CH$_2$), 25.4 (CH$_2$), 17.00 (CH$_2$), 0.3 (CH$_3$), −1.2 (CH$_3$); HRMS (ESI) calcd for $C_{41}H_{51}N_3O_7ClSi$ [M+H]$^+$ 760.3185, found 760.3189.

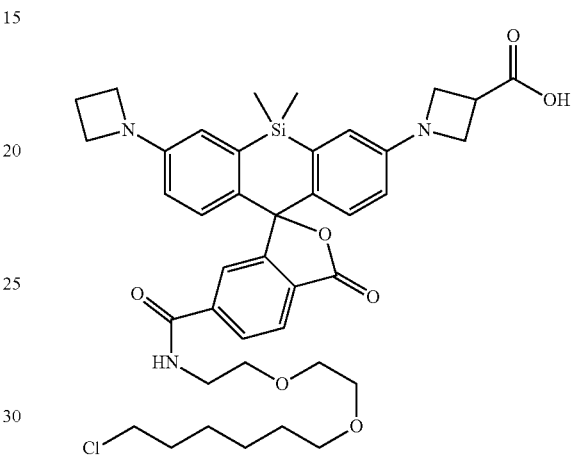

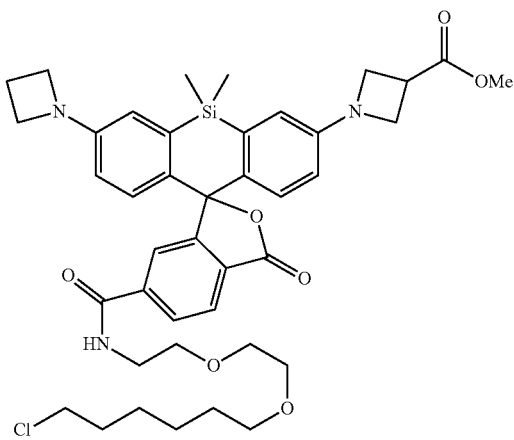 [SMILES: COC(=O)C1CN(c2ccc3c(c2)[Si](C)(C)c2cc(N4CCC4)ccc2C32OC(=O)c3ccc(C(=O)NCCOCCOCCCCCCCl)cc32)C1]

3″-methoxycarbonyl-JF$_{646}$-HaloTag ligand (S33): S31 (110 mg, 0.18 mmol) was taken up in CH$_2$Cl$_2$ (3 mL) and trifluoroacetic acid (0.6 mL) was added. The reaction was stirred at room temperature for 3 h. Toluene (3 mL) was added, the reaction mixture was concentrated to dryness and then azeotroped with MeOH three times. The residue was combined with HaloTag(O2)amine S27 (TFA salt, 182 mg, 0.54 mmol, 3.0 eq), HATU (205 mg, 0.54 mmol, 3.0 eq) in DMF (4 mL). DIEA (156 μL, 0.90 mmol, 5.0 eq) was added and the mixture was stirred at room temperature for 2 h. It was subsequently evaporated to dryness. Purification by silica gel chromatography (50-100% EtOAc/hexanes, linear gradient) provided S33 as an off-white solid (74 mg, 54%). $^1$H NMR (CDCl$_3$, 400 MHz) δ 7.98 (d, J=7.9 Hz, 1H), 7.90 (dd, J=8.0, 1.4 Hz, 1H), 7.70-7.68 (m, 1H), 6.83 (br s, 1H), 6.79-6.75 (m, 2H), 6.70-6.65 (m, 2H), 6.31-6.25 (m, 2H), 4.12-4.08 (m, 2H), 4.07-4.02 (m, 2H), 3.89 (t, J=7.3 Hz, 4H), 3.74 (s, 3H), 3.66-3.61 (m, 6H), 3.57-3.53 (m, 3H), 3.50 (t, J=6.7 Hz, 2H), 3.39 (t, J=6.7 Hz, 2H), 2.36 (p, J=5.5 Hz, 2H), 1.76-1.67 (m, 2H), 1.51 (p, J=6.9 Hz, 2H), 1.43-1.35 (m, 2H), 1.34-1.26 (m, 2H), 0.63 (s, 3H), 0.57 (s, 3H); $^{13}$C NMR (CDCl$_3$, 101 MHz) δ 173.2 (C), 170.0 (C), 166.3 (C), 155.1 (C), 151.1 (C), 150.3 (C), 139.0 (C), 136.9 (C), 3″-carboxy-JFR$_{46}$-HaloTag ligand (S34): S33 (50 mg, 66 μmol) was taken up in THF/MeOH (1/1: 4 mL) and NaOH (1 M in H$_2$O, 260 μL, 0.26 mmol, 4.0 eq) was added. The reaction was stirred at room temperature for 1 h. It was subsequently neutralized with HCl 1 M (300 μL). The residue was diluted with H$_2$O and the organics were evaporated. The aqueous layer was extracted with CH$_2$Cl$_2$ (3×). The combined organic layers were dried over MgSO$_4$, filtered, and evaporated to afford S34 as a blue solid (42 mg, 85%). The material was used without further purification. $^1$H NMR (CDCl$_3$, 400 MHz) δ 7.98 (dd, J=7.9, 0.7 Hz, 1H), 7.91 (dd, J=8.0, 1.4 Hz, 1H), 7.70 (t, J=1.1 Hz, 1H), 6.91 (br s, 1H), 6.79-6.74 (m, 2H), 6.69-6.65 (m, 2H), 6.30-6.24 (m, 2H), 4.11-4.01 (m, 4H), 3.89 (t, J=7.3 Hz, 4H), 3.63 (dt, J=8.7, 2.3 Hz, 6H), 3.57-3.53 (m, 3H), 3.49 (t, J=6.6 Hz, 2H), 3.39 (t, J=6.7 Hz, 2H), 2.42-2.32 (m, 2H), 1.77-1.69 (m, 2H), 1.55-1.47 (m, 2H), 1.44-1.35 (m, 2H), 1.33-1.25 (m, 2H), 0.63 (s, 3H), 0.57 (s, 3H); $^{13}$C NMR (CDCl$_3$, 101 MHz) δ 176.6 (C), 170.0 (C), 166.5 (C), 154.9 (C), 151.1 (C), 150.2 (C), 139.8 (C), 137.1 (C), 136.7 (C), 133.3 (C), 132.2 (C), 129.1 (C), 127.94 (CH), 127.91 (CH), 127.7 (CH), 126.0 (CH), 123.7 (CH), 116.1 (CH), 115.9 (CH), 112.8 (CH), 112.6 (CH), 92.2 (C), 71.3 (CH$_2$), 70.3 (CH$_2$), 70.0 (CH$_2$), 69.6 (CH$_2$), 54.45 (CH$_2$), 54.44 (CH$_2$), 52.4 (CH$_2$), 45.1 (CH$_2$), 40.1 (CH$_2$), 33.5 (CH), 32.57 (CH$_2$), 29.4 (CH$_2$), 26.7 (CH$_2$), 25.4 (CH$_2$), 17.0 (CH$_2$), 0.4 (CH$_3$), −1.2 (CH$_3$); HRMS (ESI) calcd for $C_{40}H_{49}N_3O_7ClSi$ [M+H]$^+$ 746.3028, found 746.3036.

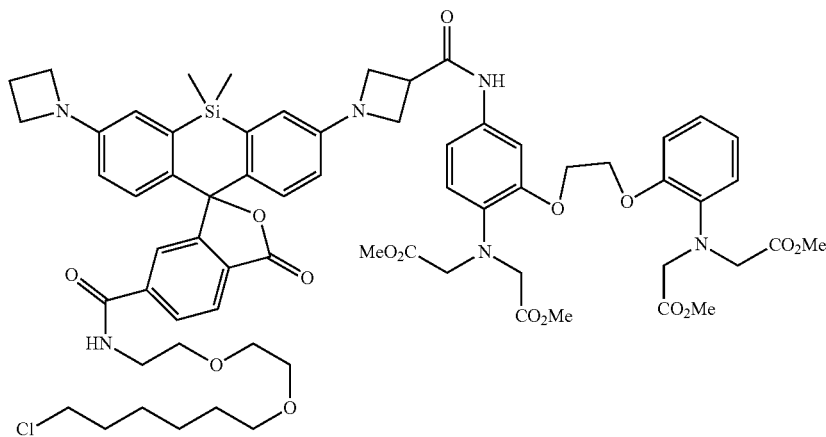 [SMILES: COC(=O)CN(CC(=O)OC)c1ccccc1OCCOc1cc(NC(=O)C2CN(c3ccc4c(c3)[Si](C)(C)c3cc(N5CCC5)ccc3C43OC(=O)c4ccc(C(=O)NCCOCCOCCCCCCCl)cc43)C2)ccc1N(CC(=O)OC)CC(=O)OC]

3″-BAPTA-JF$_{646}$-HaloTag ligand tetramethyl ester (S35): A vial was charged with S34 (25 mg, 0.034 mmol), 11[5] (22 mg, 0.040 mmol, 1.2 eq), EDC·HCl (10 mg, 0.050 mmol, 1.5 eq) and DMAP (0.9 mg, 0.007 mmol, 0.2 eq) CH$_2$Cl$_2$ (4 mL) was added. The mixture was stirred at room temperature for 1 h and concentrated to dryness. Purification by silica gel chromatography (50-100% EtOAC/hexanes, linear gradient) provided S35 as an off-white solid (29 mg, 68%).1H NMR (CDCl$_3$, 400 MHz) δ 8.03 (s, 11H), 7.98 (d, J=7.9 Hz, 11H), 7.92 (dd, J=7.9, 1.3 Hz, 1H), 7.68 (s, 1H), 7.30 (s, 1H), 7.06 (dd, J=8.7, 2.3 Hz, 1H), 6.93-6.82 (m, 5H), 6.79-6.72 (m, 3H), 6.69-6.64 (m, 2H), 6.28-6.23 (m, 2H), 4.28-4.21 (m, 4H), 4.14 (s, 4H), 4.10 (s, 4H), 4.06-3.92 (m, 4H), 3.89 (t, J=7.2 Hz, 4H), 3.65-3.52 (m, 211H), 3.49 (t, J=6.6 Hz, 2H), 3.38 (t, J=6.6 Hz, 2H), 2.39-2.32 (m, 2H), 1.71 (p, J=7.0 Hz, 2H), 1.49 (p, J=7.2 Hz, 2H), 1.38 (p, J=7.5, 6.9 Hz, 2H), 1.32-1.26 (m, 2H), 0.62 (s, 3H), 0.55 (s, 3H); Analytical HPLC: $t_R$=13.9 min, 98% purity (10-95% MeCN/H$_2$O, linear gradient, with constant 0.1% v/v TFA additive, 20 min run, 1 mL/min flow, detection at 254 nm); HRMS (ESI) calcd for C$_{66}$H$_{79}$N$_6$O$_{16}$ClSiNa [M+Na]$^+$ 1297.4908, found 1297.4889.

3″-BAPTA-JF$_{646}$-HaloTag ligand (13): To a solution of S35 (20 mg, 0.016 mmol) in THF/MeOH (1/1: 3 mL) was added KOH (1 M in H$_2$O, 280 µL, 0.28 mmol, 18 eq). The mixture was stirred at room temperature for 8 h. It was subsequently neutralized with HCl 1 M, concentrated and diluted with MeOH. Purification by reverse phase HPLC (40-60% MeCN/H$_2$O, linear gradient, with constant 0.1% v/v TFA additive) afforded 13 as a blue solid (12.7 mg, 60%, TFA salt). $^1$H NMR (CD$_3$OD, 400 MHz) δ 8.72 (s, 1H), 8.25 (d, J=8.2 Hz, 1H), 8.10 (dd, J=8.2, 1.8 Hz, 1H), 7.70-7.68 (m, 1H), 7.43-7.41 (m, 1H), 7.05-6.85 (m, 10H), 6.39-6.34 (m, 2H), 4.50-4.26 (m, 12H), 4.05-4.02 (m, 8H), 3.82-3.73 (m, 1H), 3.66-3.50 (m, 8H), 3.51 (t, J=6.6 Hz, 2H), 3.42 (t, J=6.5 Hz, 2H), 2.50 (p, J=7.6 Hz, 2H), 1.74-1.66 (m, 2H), 1.50 (p, J=6.8 Hz, 2H), 1.44-1.34 (m, 2H), 1.33-1.26 (m, 2H), 0.60 (s, 3H), 0.55 (s, 3H); Analytical HPLC: $t_R$=11.9 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{62}$H$_{72}$N$_6$O$_6$ClSi [M+H]$^+$ 1219.4463, found 1219.4462.

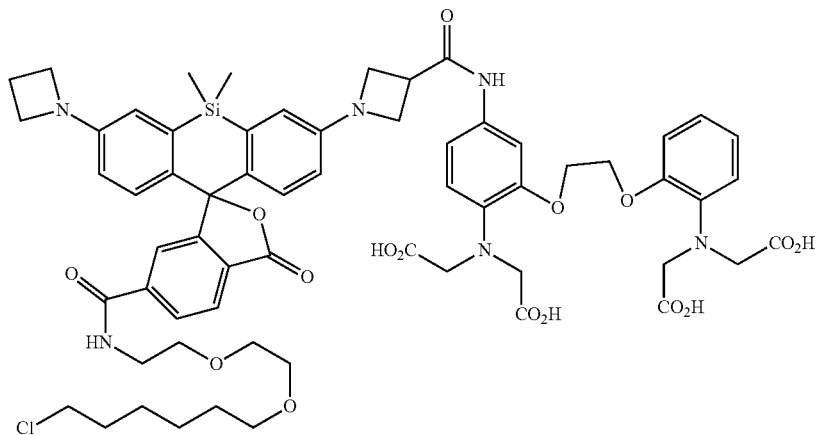 [SMILES: C[Si]1(C)c2cc(N3CCC3)ccc2C2(OC(=O)c3ccc(C(=O)NCCOCCOCCCCCCCl)cc32)c2ccc(N3CC(C(=O)Nc4ccc(N(CC(=O)O)CC(=O)O)c(OCCOc5ccccc5N(CC(=O)O)CC(=O)O)c4)C3)cc21]

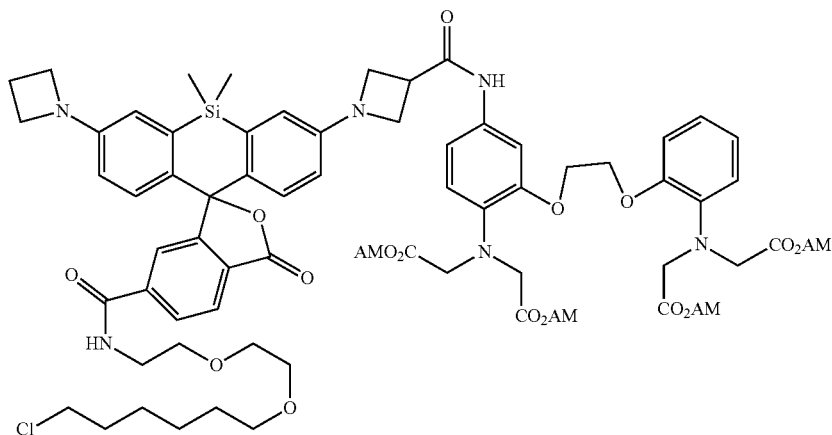

3″-BAPTA-JF$_{646}$-HaloTag ligand tetra acetoxymethyl ester (13$_{AM}$): A vial was charged with S34 (15 mg, 0.020 mmol), S19[7] (19 mg, 0.024 mmol, 1.2 eq), EDC·HCl (5.8 mg, 0.030 mmol, 1.5 eq) and DMAP (0.5 mg, 0.004 mmol, 0.2 eq). CH$_2$Cl$_2$ (2.5 mL) was added. The mixture was stirred at room temperature for 1 h and concentrated to dryness. Purification by reverse phase HPLC (30-70% MeCN/H$_2$O, linear gradient, with constant 0.1% v/v TFA additive) afforded 13$_{AM}$ as a blue solid (13.2 mg, 41%, TFA salt).$_1$H NMR (CDCl$_3$, 400 MHz) δ 8.54 (s, 1H), 8.02 (d, J=7.8 Hz, 1H), 7.91 (d, J=8.0 Hz, 1H), 7.68 (s, 1H), 7.31 (s, 1H), 7.16 (d, J=8.5 Hz, 1H), 7.07-7.01 (m, 1H), 7.00-6.95 (m, 1H), 6.93-6.76 (m, 7H), 6.37-6.30 (m, 2H), 5.67-5.59 (m, 8H), 4.34-4.27 (m, 4H), 4.24-4.02 (m, 16H), 3.68-3.60 (m, 7H), 3.58-3.54 (m, 2H), 3.50 (t, J=6.6 Hz, 2H), 3.40 (t, J=6.6 Hz, 2H), 2.48-2.40 (m, 2H), 2.07-2.01 (m, 12H), 1.73 (p, J=6.8 Hz, 2H), 1.52 (p, J=6.9 Hz, 2H), 1.43-1.35 (m, 2H), 1.33-1.25 (m, 2H), 0.62 (s, 3H), 0.55 (s, 3H); Analytical HPLC: $t_R$=13.8 min, 99% purity (10-95% MeCN/H$_2$O, linear gradient, with constant 0.1% v/v TFA additive, 20 min run, 1 mL/min flow, detection at 254 nm); HRMS (ESI) calcd for C$_{74}$H$_{87}$N$_6$O$_{24}$ClSiNa [M+Na]$^+$ 1529.5127, found 1529.5130.

Example 13: Plasmids and viruses generation. Generally, cloning was done by restriction enzyme digest of plasmid backbones, PCR amplification of inserted fragments, and isothermal assembly to combine them, followed by Sanger sequencing to verify DNA sequences. For the preparation of viruses, plasmid DNA was purified by the Janelia Molecular Biology Facility and AAV were prepared by the Janelia Virus Services.

Molecular cloning for HaloTag and GECIs for expression in primary neuron cultures. Plasmids for HaloTag, jRGECO1a and jRCaMP1b (gift from the GENIE Project Team, Janelia) were cloned with a nuclear export signal and as C-terminal EGFP fusion into the pAAV-hsyn plasmid backbone.

Molecular cloning for Tet-on 5HT$_6$-HaloTag. Human 5HT$_6$ was amplified by PCR from Kpnl to Spel site (Addgene 35624). HaloTag was amplified by PCR from AsiSL to Spel from HaloTag7 plasmid (gift from Ariana Tkachuk, Janelia). These two constructs were cloned into corresponding sites on XLone-GFP (Addgene 96930).

Example 14: Spectroscopy and Microscopy

All measurements were taken at ambient temperature (23±2° C.). Fluorescent molecules were prepared as stock solutions in DMSO and diluted such that the DMSO concentration did not exceed 1% v/v. Spectroscopy was performed using 1-cm path length quartz cuvettes (Starna). Absorption measurements were recorded on a Cary Model 100 spectrometer (Varian). Fluorescence measurements spectra were recorded on a Cary Eclipse fluorometer (Varian). Images were processed in ImageJ/Fiji. Data was analyzed and graphs were plotted using Prism (GraphPad). Movie renderings were done using Imaris (Bitplane)

Example 15: UV-Vis and Fluorescence Spectroscopy, K$_d$ Determination. UV-Vis and fluorescence spectra were measured in a commercial EGTA buffer system (Invitrogen) following the associated protocol. Briefly, different proportions of EGTA buffer (30 mM MOPS pH 7.2, 10 mM EGTA, 100 mM KCl) or Ca-EGTA buffer (30 mM MOPS pH 7.2, 10 mM Ca-EGTA, 100 mM KCl) were mixed to give solutions with different free [Ca$^{2+}$] based on a K$_d$ of Ca·EGTA=141.5 nM (value from maxchelator.stanford.edu at 25° C., 0.1 M ionic strength, pH 7.2). For calcium titrations of the HaloTag ligands in the presence of HaloTag protein, the dye was incubated with 1.5 eq of purified HaloTag protein (100 M solution in 75 mM NaCl, 50 mM Tris-HCl, pH 7.4) for 1 h at room temperature. Calcium titrations were then performed using the commercial EGTA buffer system to which 0.1 mg·mL$^{-1}$ CHAPS was added. All the calcium titrations were performed in duplicate.

Example 16: Quantum Yield Determination. Absolute quantum yields (Φ) were measured using a Quantaurus-QY spectrometer (model C11374) from Hamamatsu. This instrument uses an integrating sphere to determine photons absorbed and emitted by a sample. Measurements were carried out using dilute samples (A<0.1) and self-absorption corrections were performed using the instrument software.[27]

Example 17: Calcium Indicators Characterization in Primary Neuron Culture. Primary rat hippocampal neurons were prepared as described previously and infected with AAV viruses.[1] Stock solutions of the different calcium indicators were prepared at C=1 mM in DMSO containing 20% Pluronic F-127. Cultured neurons were incubated with the cell-permeant sensors at 37° C. for 30 min (7$_{AM}$ and Calcium Orange-AM) or 2 h (12$_{AM}$ and 13$_{AM}$) before washing twice with imaging buffer containing the following: 145 mM NaCl, 2.5 mM KCl, 10 mM glucose, 10 mM HEPES, pH 7.4, 2 mM CaCl$_2$), 1 mM MgCl$_2$. Synaptic blockers (10 μM CNQX, 10 μM CPP, 10 μM GABAZINE, and 1 mM MCPG) were added to block ionotropic glutamate, GABA, and metabotropic glutamate receptors.[21] Each measurement was performed on 3 to 5 wells replicates.

Wide-field imaging was performed on an inverted Nikon Eclipse Ti2 microscope equipped with a SPECTRA X light engine (Lumencore), 20× objective (NA=0.75, Nikon), and imaged onto a scientific CMOS camera (Hamamatsu ORCA-Flash 4.0). A FITC filter set (475/50 nm (excitation), 540/50 nm (emission), and a 506LP dichroic mirror (FITC-5050A-000; Semrock)) was used to image GFP. A Cy3 filter set (531/40 nm (excitation), 593/40 nm (emission), and a 562LP dichroic mirror (Cy3-4040C-000; Semrock)) was used to image all $JF_{549}$-based indicators, Calcium Orange-AM, as well as jRGECO1a and jRCaMP1b. A quad bandpass filter (set number: 89000, Chroma) was used along with the appropriate color band from the SPECTRA X light source to image $13_{AM}$. Action potentials (AP) were evoked by field stimulation with a custom-built electrode, controlled by a high current isolator ($A^{385}$, World Precision Instruments) set at 90 mA inserted into the medium.

Brightness comparison: The brightness of $12_{AM}$, jRGECO1a and jRCaMP1b in neurons were compared under the same illumination conditions. The fluorescence emission in each field of view was background subtracted and normalized by the emission of the fused EGFP to account for differences in expression levels among neurons.

Photobleaching correction: The average normalized fluorescence traces for $JF_{549}$-BAPTA-HaloTag protein conjugate, jRGECO1a and jRCaMP1b in neurons were linearly corrected for bleaching. The apparent faster photobleaching rate of $12_{AM}$ compared to the red GECIs can be explained by the different nature of the fluorophore and sensing mechanism. The fitting parameters used for the correction are given in the table below and correspond to the equation $y=a*x+b$:

| Indicator | a ($s^{-1}$) | b |
|---|---|---|
| $12_{AM}$ | −0.0009167 | 1.004 |
| jRCaMP1b | 0.0004504 | 0.2815 |
| jRGECO1a | 0.00006458 | 0.1215 |

Example 18: Fluorescence Microscopy in Primary Cilia. Stable cell line creation: hTERT-RPE cells (ATCC CRL-4000) were transfected with a piggyBac transposase vector (gift from Dr. James Liu, Janelia) and a 5HT6-HaloTag vector concurrently with Fugene HD (Promega) and grown in DMEM:F12 media (ATCC-30-2006) with 10% Tet-free FBS (Gemini). The cells were then selected by blasticidin to create Tet-on 5HT6-HaloTag stable cells.

Tet-on 5HT6-HaloTag RPE cells were plated in 8-well Labtek II chambers (Invitrogen) in 10% FBS DMEM:F12 media. The next day, the cells were serum deprived with 0% FBS DMEM:F12 medium with 100 ng/ml doxycycline to induce 5HT6-HaloTag expression. After 24 h of serum deprivation and doxycycline induction, cells were labeled with 1 μM $13_{AM}$ overnight. After rinsing in DMEM:F12, the cells were loaded with 4 μM NP-EGTA, AM (ThermoFisher N6803) for 1 h. The medium was then replaced by DMEM Fluorobrite (ThermoFisher) for imaging in a 37° C., 5% $CO_2$ chamber on an inverted Zeiss 880 with Airyscan. For each single cilium, 405 nm laser light (100%, 15 mW, 3s) uncaged free $Ca^{2+}$ from NP-EGTA in a 50-70 μm² area. Airyscan images were acquired at 0.5-0.8 s/stack for a total of 100 stacks (50-80 s) with 633 laser lines (13AM). Calcium uncaging was performed at the $50^{th}$ stack. Change in intensity values were calculated in ImageJ using a maximum intensity projection series.

As described herein, the established strategy of BAPTA-based $Ca^{2+}$ indicators has been refined and extended in three ways. First, a brighter dye, $JF_{549}$, has been used and the relative position of the BAPTA chelator and the fluorophore has been diligently studied. This resulted in a novel configuration where the BAPTA is attached through the aniline nitrogen on the rhodamine rather than the traditional position on the pendant phenyl ring. Second, this molecule could be appended with the HaloTag ligand in the optimal position, allowing facile and selective labeling inside live neurons with superior brightness to extant red-shifted GECIs. Finally, this strategy was applied to the Si-rhodamine $JF_{646}$, generating the first fluorogenic far-red targetable $Ca^{2+}$ indicator and used it to measure calcium fluxes in the primary cilium. The red-shifted spectral properties of these bright and sensitive indicators make them compatible with GFP-based reporters and optogenetic tools. Importantly, this general design can be extended to create $Ca^{2+}$ indicators with different affinities and sensors for other cellular analytes, all of which can be used with established labeling strategies to enable subcellular functional imaging experiments.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Clapham, D. E., Calcium signaling. *Cell* 2007, 131, 1047-1058.
2. Grienberger, C.; Konnerth, A., Imaging calcium in neurons. *Neuron* 2012, 73, 862-885.
3. Paredes, R. M.; Etzler, J. C.; Watts, L. T.; Zheng, W.; Lechleiter, J. D., Chemical calcium indicators. *Methods* 2008, 46, 143-151.
4. Perez Koldenkova, V.; Nagai, T., Genetically encoded $Ca^{2+}$ indicators: Properties and evaluation. Biochim. Biophys. Acta 2013, 1833, 1787-1797.
5. Chen, T. W.; Wardill, T. J.; Sun, Y.; Pulver, S. R.; Renninger, S. L.; Baohan, A.; Schreiter, E. R.; Kerr, R. A.; Orger, M. B.; Jayaraman, V.; Looger, L. L.; Svoboda, K.; Kim, D. S., Ultrasensitive fluorescent proteins for imaging neuronal activity. *Nature* 2013, 499, 295-300.
6. Dana, H.; Mohar, B.; Sun, Y.; Narayan, S.; Gordus, A.; Hasseman, J. P.; Tsegaye, G.; Holt, G. T.; Hu, A.; Walpita, D.; Patel, R.; Macklin, J. J.; Bargmann, C. I.; Ahrens, M. B.; Schreiter, E. R.; Jayaraman, V.; Looger, L. L.; Svoboda, K.; Kim, D. S., Sensitive red protein calcium indicators for imaging neural activity. *eLife* 2016, 5, e12727.
7. Qian, Y.; Piatkevich, K. D.; Mc Larney, B.; Abdelfattah, A. S.; Mehta, S.; Murdock, M. H.; Gottschalk, S.; Molina, R. S.; Zhang, W.; Chen, Y.; Wu, J.; Drobizhev, M.; Hughes, T. E.; Zhang, J.; Schreiter, E. R.; Shoham, S.; Razansky, D.; Boyden, E. S.; Campbell, R. E., A genetically encoded near-infrared fluorescent calcium ion indicator. *Nat. Methods* 2019, 16, 171-174.
8. Tour, O.; Adams, S. R.; Kerr, R. A.; Meijer, R. M.; Sejnowski, T. J.; Tsien, R. W.; Tsien, R. Y., Calcium Green FlAsH as a genetically targeted small-molecule calcium indicator. *Nat. Chem. Biol.* 2007, 3, 423-431.

9. Kamiya, M.; Johnsson, K., Localizable and highly sensitive calcium indicator based on a BODIPY fluorophore. *Anal. Chem.* 2010, 82, 6472-6479.
10. Bannwarth, M.; Corr8a, I. R.; Sztretye, M.; Pouvreau, S.; Fellay, C.; Aebischer, A.; Royer, L.; Rios, E.; Johnsson, K., Indo-1 derivatives for local calcium sensing. *ACS Chem. Biol.* 2009, 4, 179-190.
11. Best, M.; Porth, I.; Hauke, S.; Braun, F.; Herten, D. P.; Wombacher, R., Protein-specific localization of a rhodamine-based calcium-sensor in living cells. *Org. Biomol. Chem.* 2016, 14, 5606-5611.
12. Tsien, R. Y., New calcium indicators and buffers with high selectivity against magnesium and protons: design, synthesis, and properties of prototype structures. *Biochemistry* 1980, 19, 2396-2404.
13. Minta, A.; Kao, J. P. Y.; Tsien, R. Y., Fluorescent indicators for cytosolic calcium based on rhdamine and fluorescein chromophores. *J. Biol. Chem.* 1989, 264, 8171-8178.
14. Gee, K. R.; Brown, K. A.; Chen, W. N.; Bishop-Stewart, J.; Gray, D.; Johnson, I., Chemical and physiological characterization of fluo-4 Ca(2+)-indicator dyes. *Cell Calcium* 2000, 27, 97-106.
15. Johnson, I.; Spence, M. T. Z., The Molecular Probes Handbook: A guide to fluorescent probes an labeling technologies. 2010.
16. Sawinski, J.; Wallace, D. J.; Greenberg, D. S.; Grossmann, S.; Denk, W.; Kerr, J. N., Visually evoked activity in cortical cells imaged in freely moving animals. *Proc. Natl. Acad. Sci. U.S.A* 2009, 106 (46), 19557-19562.
17. Marcus, R. A., Electron transfer reactions in chemistry: theory and experiment (Nobel lecture). *Angew. Chem. Int. Ed.* 1993, 32, 1111-1222.
18. Turro, N. J.; Ramamurthy, V.; Scaiano, J. C., *Modern molecular photochemistry of organic molecules*. University Science Books, Sausalito, CA: 2010.
19. Grimm, J. B.; English, B. P.; Chen, J.; Slaughter, J. P.; Zhang, Z.; Revyakin, A.; Patel, R.; Macklin, J. J.; Normanno, D.; Singer, R. H.; Lionnet, T.; Lavis, L. D., A general method to improve fluorophores for live-cell and single-molecule microscopy. *Nat. Methods* 2015, 12, 244-250.
20. Greene, L. E.; Lincoln, R.; Cosa, G., Tuning photoinduced electron transfer efficiency of fluorogenic BODIPY-alpha-Tocopherol analogues. *Photochem. Photobiol.* 2019, 95, 192-201.
21. Wardill, T. J.; Chen, T. W.; Schreiter, E. R.; Hasseman, J. P.; Tsegaye, G.; Fosque, B. F.; Behnam, R.; Shields, B. C.; Ramirez, M.; Kimmel, B. E.; Kerr, R. A.; Jayaraman, V.; Looger, L. L.; Svoboda, K.; Kim, D. S., A neuron-based screening platform for optimizing genetically-encoded calcium indicators. *PLoS One* 2013, 8, e77728.
22. Los, G. V.; Encell, L. P.; McDougall, M. G.; Hartzell, D. D.; Karassina, N.; Zimprich, C.; Wood, M. G.; Learish, R. D.; Friedman Ohana, R.; Urh, M.; Simpson, D.; Mendez, J.; Zimmerman, K.; Otto, P.; Vidugiris, G.; Zhu, J.; Darzins, A.; Klaubert, D. H.; Bulleit, R. F.; Wood, K. V., HaloTag: a novel protein labeling technology for cell imaging and protein analysis. *ACS Chem. Biol.* 2008, 3, 373-382.
23. Encell, L. P.; Friedman Ohana, R.; Zimmerman, K.; Otto, P.; Vidugiris, G.; Wood, M. G.; Los, G. V.; McDougall, M. G.; Zimprich, C.; Karassina, N.; Learish, R. D.; Hurst, R.; Hartnett, J.; Wheeler, S.; Stecha, P.; English, J.; Zhao, K.; Mendez, J.; Benink, H. A.; Murphy, N.; Daniels, D. L.; Slater, M. R.; Urh, M.; Darzins, A.; Klaubert, D. H.; Bulleit, R. F.; Wood, K. V., Development of a dehalogenase-based protein fusion tag capable of rapid, selective and covalent attachment to customizable ligands. *Curr Chem. Genomics* 2012, 6, 55-71.
24. Collins, T. J.; Lipp, P.; Berridge, M. J.; Bootman, M. D., Mitochondrial Ca(2+) uptake depends on the spatial and temporal profile of cytosolic Ca(2+) signals. *J. Biol. Chem.* 2001, 276 (28), 26411-26420.
25. Satir, P.; Pedersen, L. B.; Christensen, S. T., The primary cilium at a glance. *J. Cell. Sci.* 2010, 123, 499-503.
26. Delling, M.; DeCaen, P. G.; Doerner, J. F.; Febvay, S.; Clapham, D. E., Primary cilia are specialized calcium signalling organelles. *Nature* 2013, 504, 311-314.
27. Suzuki, K.; Kobayashi, A.; Kaneko, S.; Takehira, K.; Yoshihara, T.; Ishida, H.; Shiina, Y.; Oishi, S.; Tobita, S., Reevaluation of absolute luminescence quantum yields of standard solutions using a spectrometer with an integrating sphere and a back-thinned CCD detector. *Phys. Chem. Chem. Phys.* 2009, 11, 9850-9860.
28. Grimm, J. B.; Lavis, L. D., Synthesis of rhodamines from fluoresceins using Pd-catalysed C—N cross-coupling. *Org. Lett.* 2011, 13, 6354-6357.
29. Kim, H. M.; Kim, B. R.; Hong, J. H.; Park, J. S.; Lee, K. J.; Cho, B. R., A two-photon fluorescent probe for calcium waves in living tissue. *Angew. Chem. Int. Ed.* 2007, 46, 7445-7448.
30. Egawa, T.; Hirabayashi, K.; Koide, Y.; Kobayashi, C.; Takahashi, N.; Mineno, T.; Terai, T.; Ueno, T.; Komatsu, T.; Ikegaya, Y.; Matsuki, N.; Nagano, T.; Hanaoka, K., Red fluorescent probe for monitoring the dynamics of cytoplasmic calcium ions. *Angew. Chem. Int. Ed.* 2013, 52, 3874-3877.
31. Grimm, J. B.; Muthusamy, A. K.; Liang, Y.; Brown, T. A.; Lemon, W. C.; Patel, R.; Lu, R.; Macklin, J. J.; Keller, P. J.; Ji, N.; Lavis, L. D., A general method to fine-tune fluorophores for live-cell and in vivo imaging. *Nat. Methods* 2017, 14, 987-994.
32. Lloyd, Q. P.; Kuhn, M. A.; Gay, C. V., Characterization of calcium translocation across the plasma membrane of primary osteoblasts using a lipophilic calcium-sensitive fluorescent dye, calcium green C18. *J. Biol. Chem.* 1995, 270, 22445-22451.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A compound of the formula:

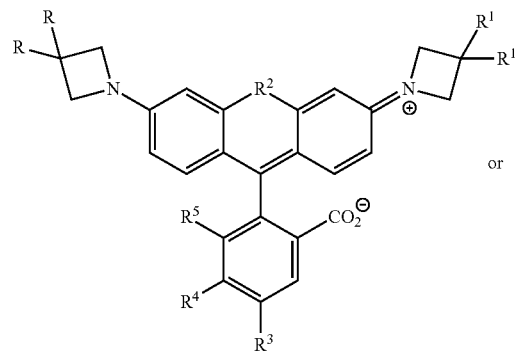

or

95
-continued

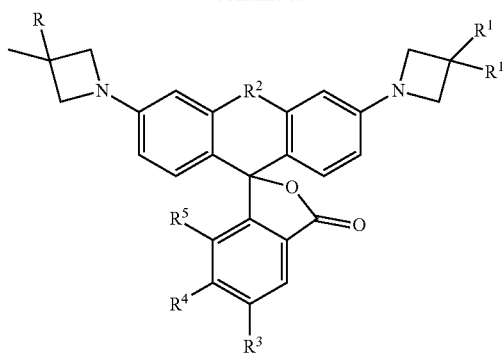

each R is independently selected from the group consisting of halogen, H, OH, CN, O(alkyl), N(alkyl), amine, $NO_2$, CHO, COOH, COO(alkyl), $O(SO_2CF_3)$, and

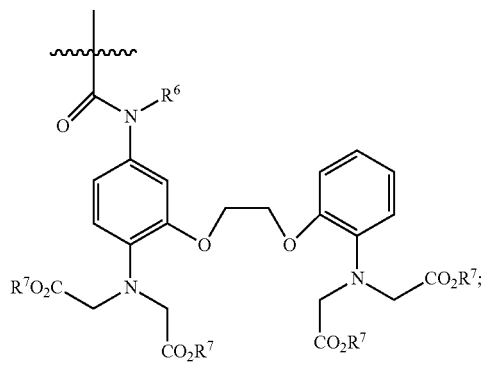

each $R^1$ is independently selected from the group consisting of halogen, H, OH, CN, O(alkyl), N(alkyl), amine, $NO_2$, CHO, COOH, COO(alkyl), $O(SO_2CF_3)$,

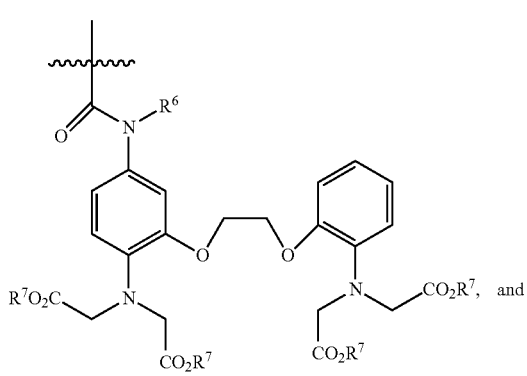

96
-continued

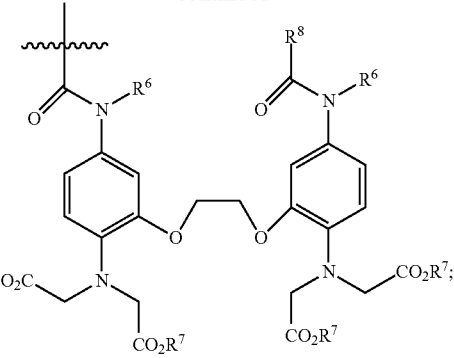

$R^2$ is selected from O, $Si(CH_3)_2$, and $C(CH_3)_2$;

$R^3$ is selected from the group consisting of H, $CO_2$t-Bu, and $CO_2H$;

$R^4$ is selected from the group consisting of H, $CO_2$t-Bu, $CO_2H$, and a self-labeling protein tag ligand;

$R^5$ is selected from the group consisting of H and $CO_2CH_3$;

$R^6$ is H or $CH_3$; and $R^7$ is H, acetoxymethyl (AM), or

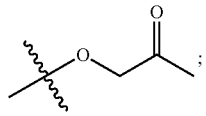 [SMILES: *OCC(C)=O]

and $R^8$ is

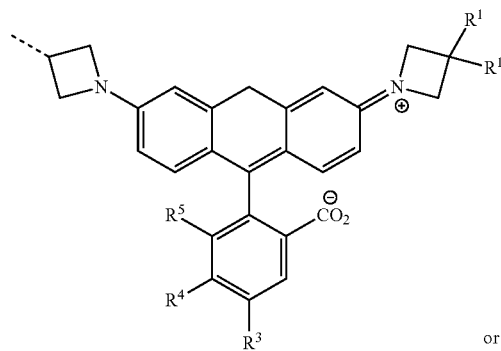

or

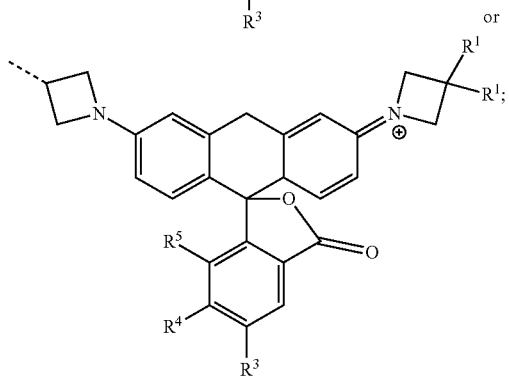

provided that at least one of
R is
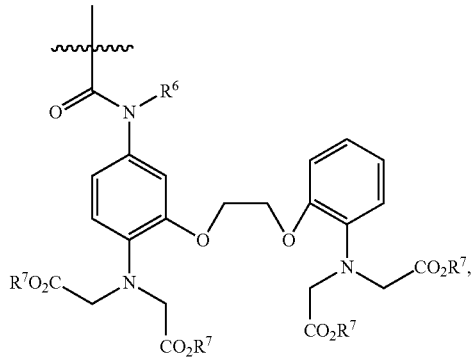
or
R¹ is
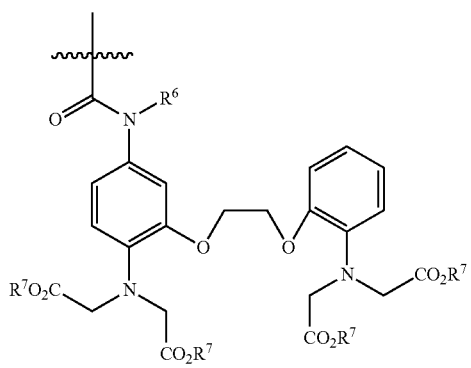
or
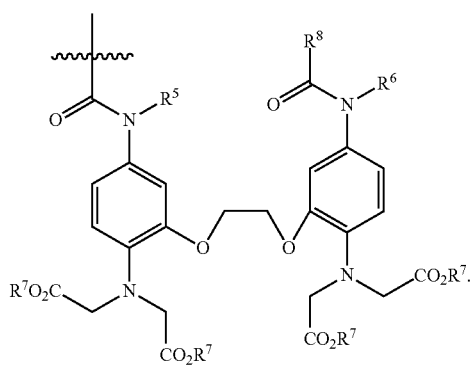
and
provided that no more than one R is
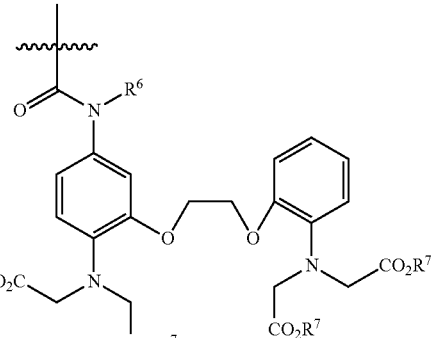
and no more than one R¹ is
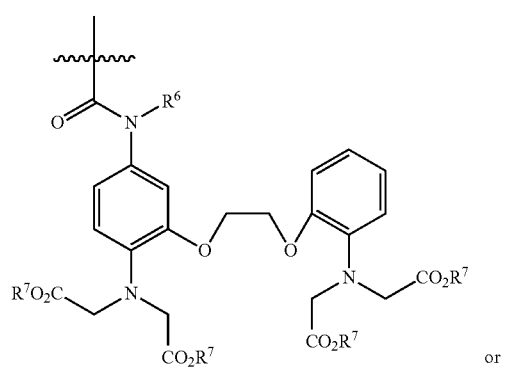
or
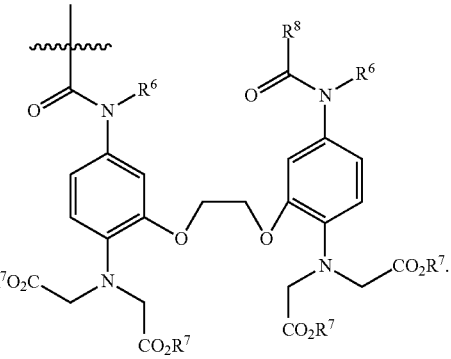
2. The compound of claim 1, wherein R is
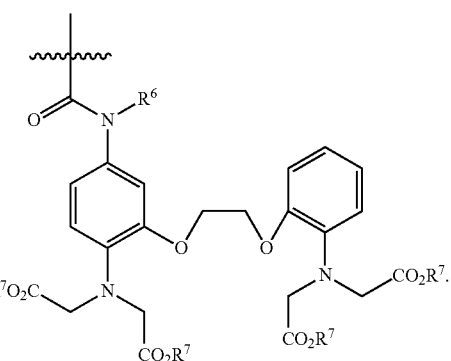

3. The compound of claim 1, having the formula:

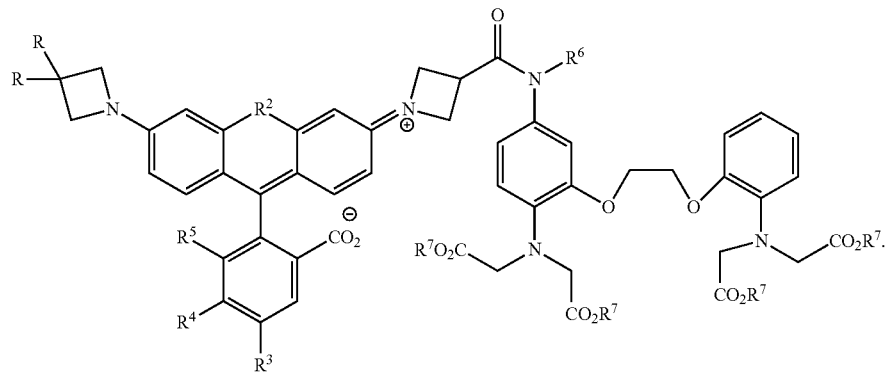

4. The compound of claim 1, wherein R is H.
5. The compound of claim 1, wherein $R^1$ is H.
6. The compound of claim 1, wherein $R^1$ is

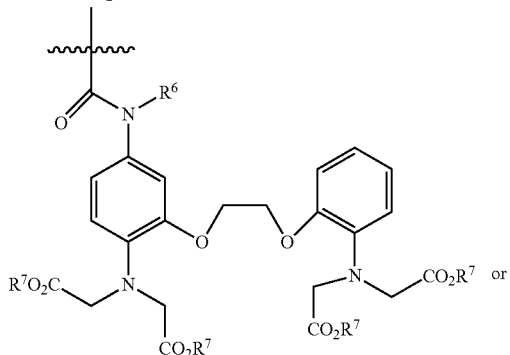 or

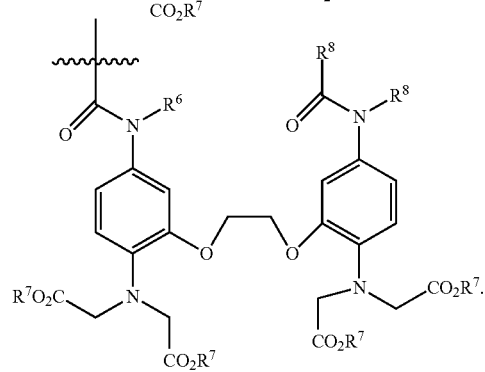

7. The compound of claim 1, wherein $R^1$ is selected from the group consisting of COOH, $COOCH_3$, and $O(SO_2CF_3)$.

8. The compound of claim 1, wherein $R^2$ is $Si(CH_3)_2$.

9. The compound of claim 1, wherein $R^2$ is O.

10. The compound of claim 1, wherein $R^3$ is H.

11. The compound of claim 1, wherein $R^4$ is H.

12. The compound of claim 1, wherein $R^4$ is a self-labeling protein tag ligand.

13. The compound of claim 12, wherein the self-labeling protein tag ligand is

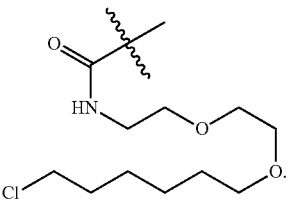 [SMILES: *C(=O)NCCOCCOCCCCCCCl]

14. The compound of claim 1, wherein $R^5$ is H.

15. A compound having a formula selected from the group consisting of:

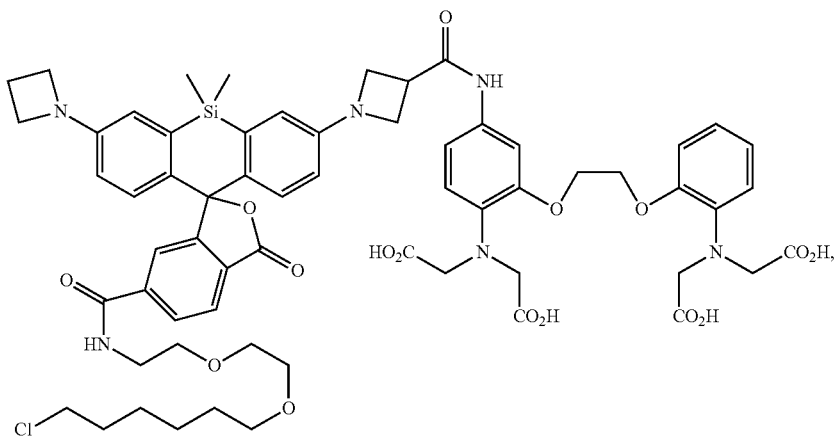

-continued
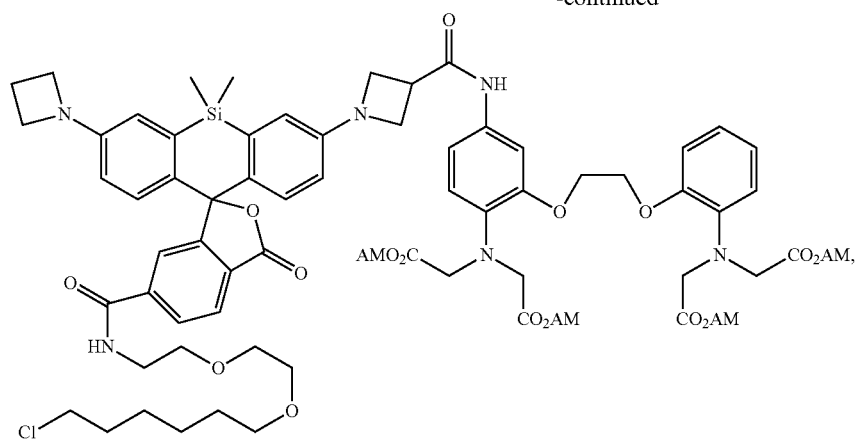
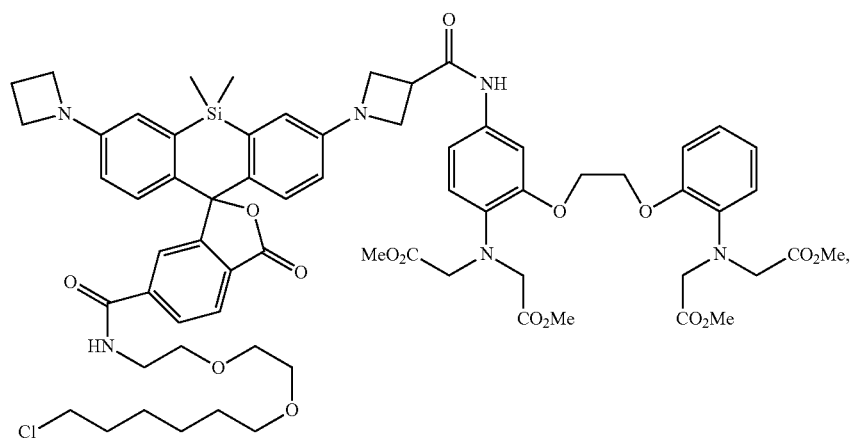
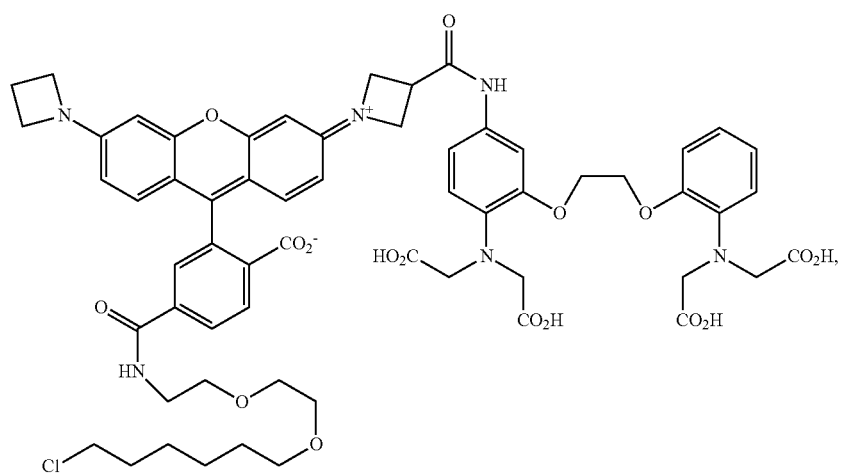

-continued
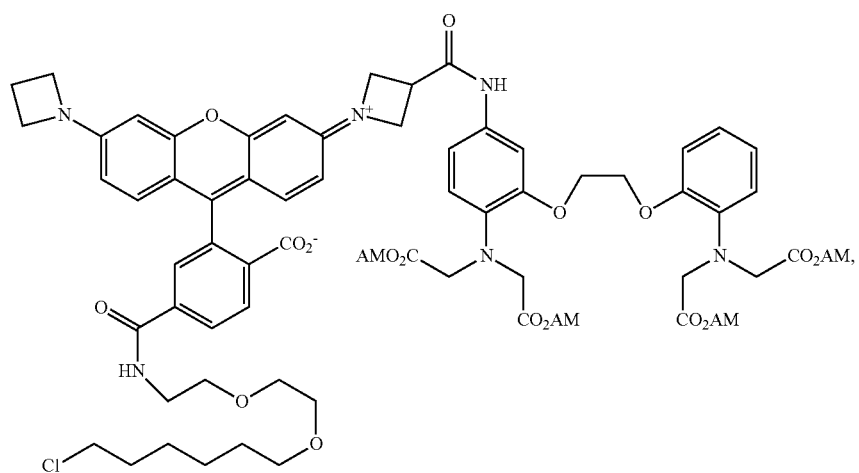
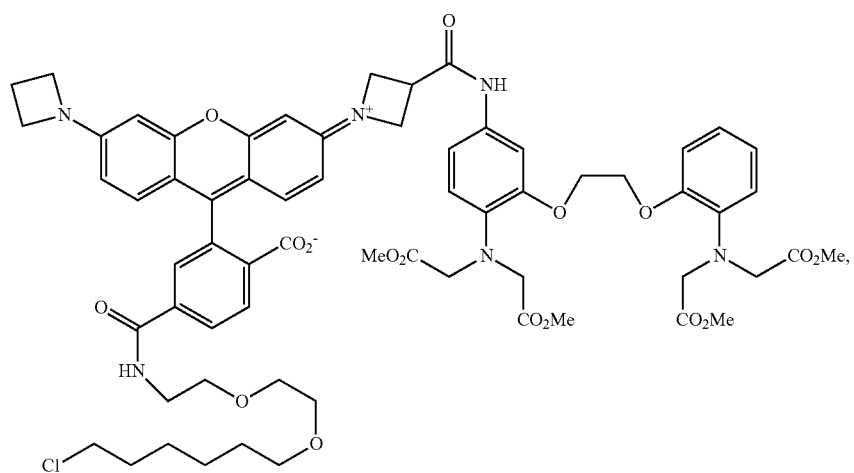
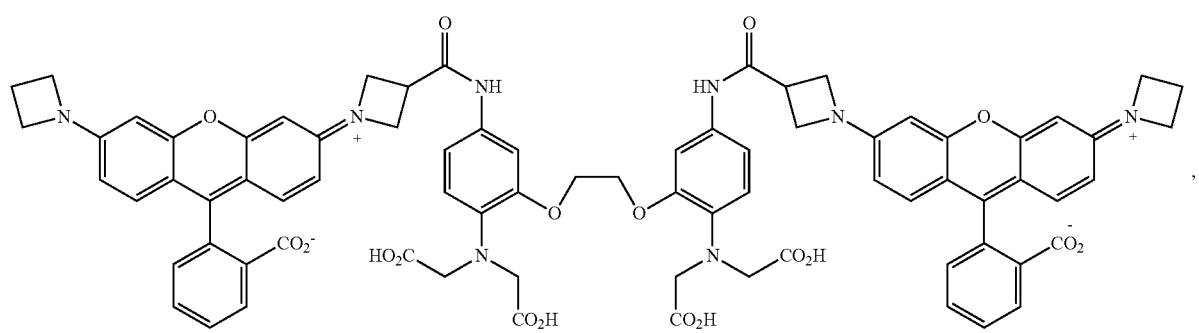
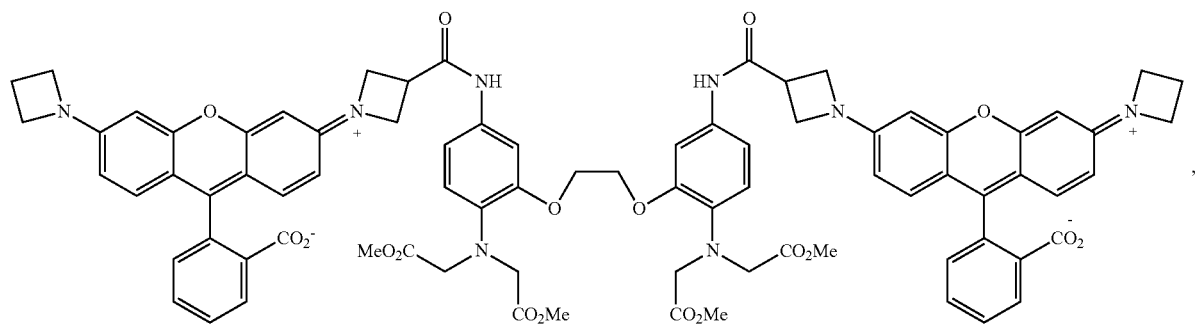

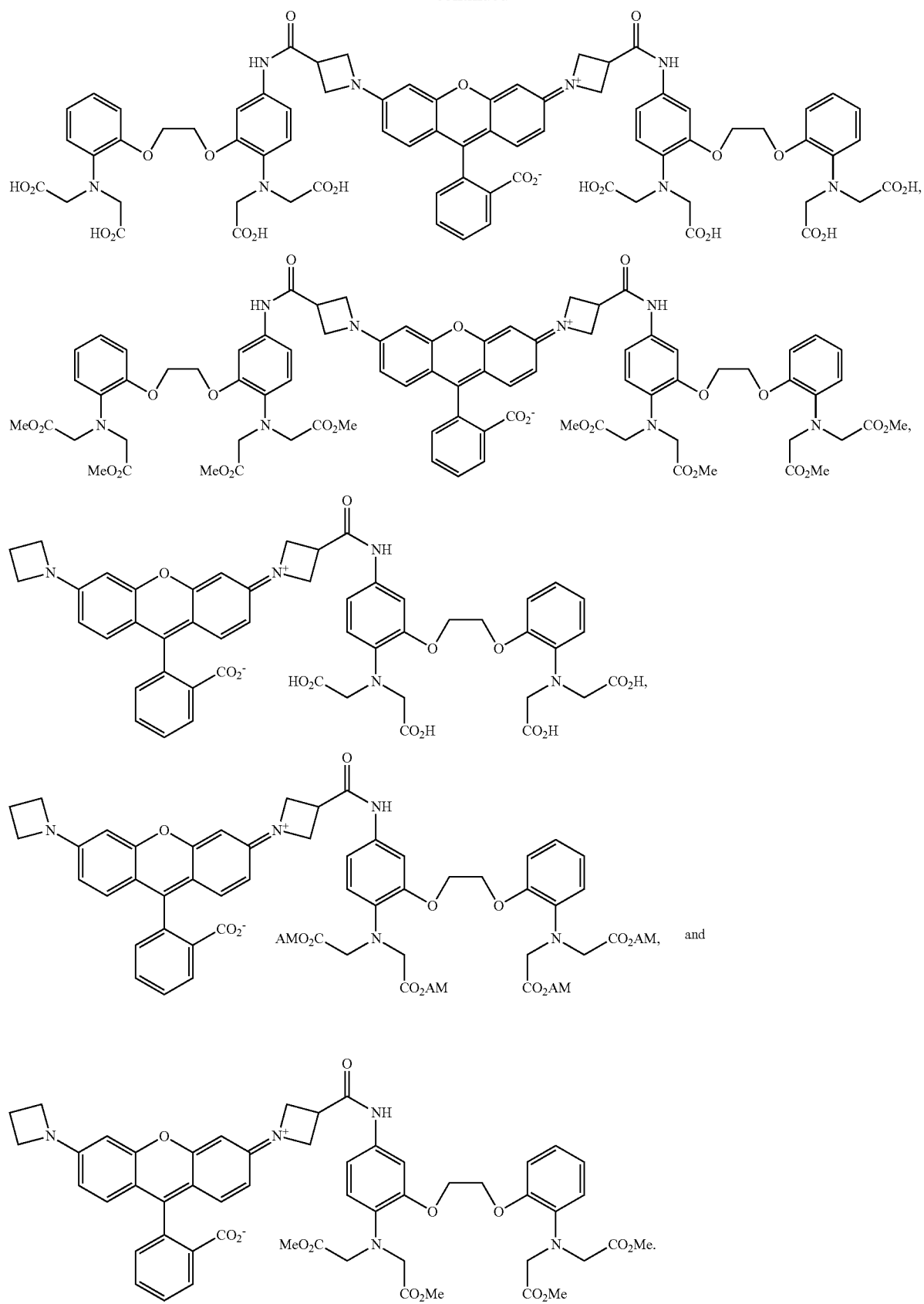

16. A method for detecting calcium in a sample, comprising: contacting the sample with a compound according to claim 1;
  exposing the sample to light; and
  detecting an emission, the emission light indicating the presence of calcium.

* * * * *